US011382848B2

United States Patent
Chatelain et al.

(10) Patent No.: US 11,382,848 B2
(45) Date of Patent: Jul. 12, 2022

(54) COMPOUNDS REDUCING MALODOUR PERCEPTION AND THE USE THEREOF

(71) Applicants: CHEMCOM S.A., Brussels (BE); GIVAUDAN S.A., Vernier (CH)

(72) Inventors: Pierre Chatelain, Brussels (BE); Markus Gautschi, Fällanden (CH); Thierry Granier, Dübendorf (CH); Yannick Quesnel, Wavre (BE); Charles Stanley Sell, Kent (GB); Alex Veithen, Genappe (BE)

(73) Assignees: CHEMCOM S.A., Brussels (BE); GIVAUDAN S.A., Vernier (CH)

( * ) Notice: Subject to any disclaimer, the term of this patent is extended or adjusted under 35 U.S.C. 154(b) by 3 days.

(21) Appl. No.: 16/480,331

(22) PCT Filed: Jan. 30, 2018

(86) PCT No.: PCT/EP2018/052191
§ 371 (c)(1),
(2) Date: Jul. 24, 2019

(87) PCT Pub. No.: WO2018/138369
PCT Pub. Date: Aug. 2, 2018

(65) Prior Publication Data
US 2019/0374451 A1 Dec. 12, 2019

(30) Foreign Application Priority Data

Jan. 30, 2017 (EP) ..................................... 17153751

(51) Int. Cl.
| A61K 8/34 | (2006.01) |
| A61K 8/36 | (2006.01) |
| A61K 8/35 | (2006.01) |
| A61K 8/37 | (2006.01) |
| A61K 8/40 | (2006.01) |
| A61K 8/42 | (2006.01) |
| A61Q 15/00 | (2006.01) |
| C07C 33/20 | (2006.01) |
| C07C 49/217 | (2006.01) |
| C07C 57/03 | (2006.01) |
| C07C 69/003 | (2006.01) |
| C07C 233/09 | (2006.01) |
| C07C 255/50 | (2006.01) |
| C11B 9/00 | (2006.01) |

(52) U.S. Cl.
CPC ............. *A61K 8/361* (2013.01); *A61K 8/34* (2013.01); *A61K 8/35* (2013.01); *A61K 8/37* (2013.01); *A61K 8/40* (2013.01); *A61K 8/42* (2013.01); *A61Q 15/00* (2013.01); *C07C 33/20* (2013.01); *C07C 49/217* (2013.01); *C07C 57/03* (2013.01); *C07C 69/003* (2013.01); *C07C 233/09* (2013.01); *C07C 255/50* (2013.01); *C11B 9/0061* (2013.01); *C11B 9/0065* (2013.01)

(58) Field of Classification Search
None
See application file for complete search history.

(56) References Cited

U.S. PATENT DOCUMENTS

| 6,297,283 B1 | 10/2001 | Ishiwata et al. |
| 2001/0039279 A1 | 11/2001 | Ishiwata et al. |
| 2007/0046645 A1 | 3/2007 | Hirota et al. |
| 2011/0046050 A1 | 2/2011 | Gschneidner et al. |
| 2012/0258911 A1 | 10/2012 | Gschneidner et al. |
| 2014/0073595 A1 | 3/2014 | Koul et al. |
| 2016/0375135 A1 | 12/2016 | Gschneidner et al. |

FOREIGN PATENT DOCUMENTS

| CN | 104693390 A | 6/2015 | |
| GB | 2 528 480 A | 1/2016 | |
| GB | 2528480 | * 1/2016 | ............... C11B 9/00 |
| WO | 9816497 A1 | 4/1998 | |
| WO | 2006103527 A1 | 10/2006 | |
| WO | 2008112368 A2 | 9/2008 | |
| WO | 2016105118 A2 | 6/2016 | |

OTHER PUBLICATIONS

Markiewicz et al (J Org Chem 75:2061-2064, 2010) (Year: 2010).*
PCT International Search Report and Written Opinion dated Mar. 20, 2018 for PCT International Patent Application No. PCT/EP2018/052191.
PCT Notification of Transmittal of the International Preliminary Report on Patentability dated Mar. 29, 2018 for PCT International Patent Application No. PCT/EP2018/052191.
John T. Markiewicz et al: "Synthesis of 4-Methyldienoates Using a Vinylogous Horner-Wadsworth-Emmons Reagent. Application to the Synthesis of Trichostatic Acid",The Journal of Organic Chemistry, vol. 75, No. 6, Mar. 19, 2010 (Mar. 19, 2010), pp. 2061-2064.

(Continued)

*Primary Examiner* — Craig D Ricci
(74) *Attorney, Agent, or Firm* — Amster, Rothstein & Ebenstein LLP

(57) ABSTRACT

The present invention relates to new malodour-counteracting agents of formula (I) or stereoisomers thereof, particularly useful in blocking the olfactory perception of androstenone, Formula (I), wherein $R^1$, $R^2$, $R^3$, $R^4$, $R^5$, $R^6$, $R^7$ and X have the same meaning as that defined in the claims. The present invention also relates to consumer products comprising said agents. The present invention also relates to the use of said agents to suppress or attenuate undesirable odour, as well as to methods to suppress or attenuate undesirable odour employing said compounds.

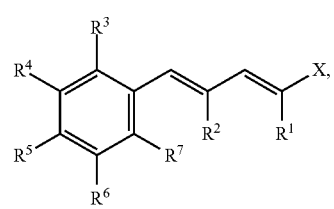

(I)

9 Claims, 1 Drawing Sheet

(56) References Cited

OTHER PUBLICATIONS

Marson C M et al: "Stereodefined and polyunsaturated inhibitors of histone deacetylase based on (2E,4E)-5-arylpenta-2,4-dienoic acid hydroxyamides", Bioorganic & Medicinal Chemistry Let, vol. 14, No. 10, May 17, 2004 (May 17, 2004), pp. 2477-2481.

Ya Grigorieva N et al: "Formal synthesis of strobilurins A and X", Russian Chemical Bulletin, vol. 59, No. 11, Mar. 31, 2011 (Mar. 31, 2011), pp. 2086-2093.

Hiroaki Horie et al: "Nickel-catalyzed intermolecular codimerization of acrylates and alkynes", Chemical Communications—ChemCom., vol. 47, No. 9, Jan. 1, 2011 (Jan. 1, 2011), p. 2658.

James W. Wilt et al: "Cyanomethylidenebis(triphenylphosphonium) Dibromide. Its Use in a Convenient Modification of the Wittig Reaction", Journal of Organic Chemistry, vol. 36, No. 14, Jan. 1, 1971 (Jan. 1, 1971), pp. 2026-2027.

Bhattacharya S et al: "Synthesis and Stereochemical Studies on the Reductions of Some Pyrrole Derivatives", Journal of the Chemical Society, Perkin Transactio, Royal Society of Chemistry, GB, Jan. 1, 1984 (Jan. 1, 1984), pp. 5-13.

Singh R et al: "A dimethylsulfonium methylide mediated highly regioselective olefination of conjugated polyolefin 1,1-dioates to conjugated polyene-2-yl-malonates and their applications in Diels@? Alder reactions", Tetrahedron, vol. 66, No. 13, Mar. 27, 2010 (Mar. 27, 2010), pp. 2284-2292.

Jing Zhang et al: "Exploring Bis(cyclometalated) Ruthenium(II) Complexes as Active Catalyst Precursors: Room-Temperature Alkene-Alkyne Coupling for 1,3-Diene Synthesis," Angew. Chem. Int. Ed. 2014, 53, 8437-8440.

David R. Williams et al: "A Preparation of Bromoolefins from Carbonyl Compounds," Tetrahedron Letters, vol. 22, No. 38, pp. 3745-3748, 1981.

Database Pubchem Compounds, Abstract No. CID 5374275, p. 3.

Perrin et al., "The Complete Mechanism of an Aldol Condensation," The Journal of Organic Chemistry, vol. 81, No. 13, Jul. 1, 2016, 17 pages (including cover sheet).

Japanese Office Action dated Sep. 7, 2021 in connection with Japanese Application No. 2019-561357.

Banker S K et al., "Palladium-Catalyzed Intramolecular Trost-Oppolzer-Type Alder-Ene Reaction of Dienyl Acetates to Cyclopentadienes," Angew Chem Int Ed Engl. Feb. 5, 2018;57(6):1678-1682.

Morris J et al., "Synthesis and Biological Evaluation of Antiplatelet 2-Aminochromones," J. Med. Chem., 1993, 36, 2026-2032.

* cited by examiner

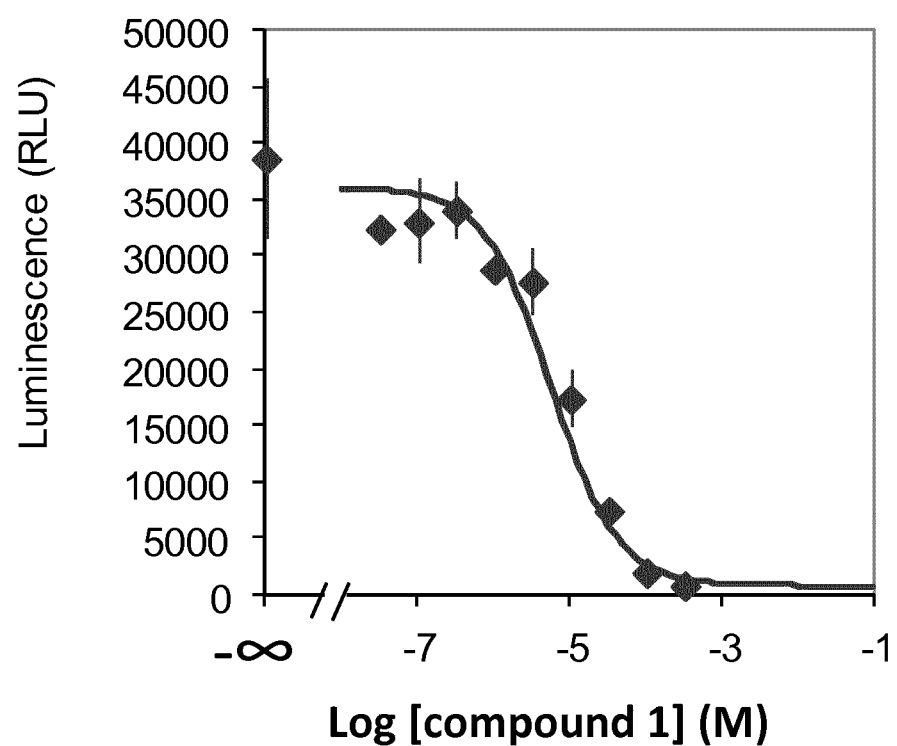

COMPOUNDS REDUCING MALODOUR PERCEPTION AND THE USE THEREOF

CROSS-REFERENCE TO RELATED APPLICATIONS

This application is a U.S. national stage entry under 35 U.S.C. § 371 of PCT International Patent Application No. PCT/EP2018/052191, filed Jan. 30, 2018, which claims priority to European Patent Application No. 17153751.7, filed Jan. 30, 2017, the contents of which are incorporated herein by reference in their entirety.

FIELD OF THE INVENTION

The present invention relates to new compounds, acting as blocking molecules, with a low odour profile that decrease the perception of the malodour molecule 5α-androst-16-en-3-one. The present invention also relates to the use of such compounds for reducing the perception of malodour, in particular sweat malodour. The present invention also provides a method for synthesizing the blocking molecules.

BACKGROUND OF THE INVENTION

5-α-Androst-16-en-3-one (androstenone) is a component of human sweat and is of particular importance in the sweat of males (D. B. Gower, *J. Steroid Biochem.*, 1972, 3, 45-103). It also found in saliva (S. Bird, D. B. Gower Experientia. 1983 Jul. 15; 39(7):790-2) and decaying urine (J. E. Amoore, P. Pelosi, L. J. Forrester Chem. Sens. Flavor 1977, 2, 401-405). It is also well known as a metabolite of male pigs and is linked to the distinctive off-note, known as boar taint, in the taste of their meat (D. B. Gower and B. A. Ruparelia, *J. Endocrin.*, 1993, 137, 167-187; V. Prelog and L. Ruzicka, *Helv. Chim. Acta*, 1944, 27, 61). It has an unpleasant odour, described variously as sweaty or urinous, with a very low odour detection threshold (A. Baydar, M. Petrzilka and M.-P. Schott, *Chem. Senses*, 1993, 18, 661-668). Thus, it is of commercial interest as a malodour and one role of deodorant perfumes is to hide its presence in axillary sweat.

A human olfactory receptor which is sensitive to androstenone and the related malodorant, androstadienone, has been identified by Keller et al. (A. Keller, H. Zhuang, Q. Chi, L. B. Vosshall and H. Matsunami, *Nature*, 2007, 449, 468-472 doi: 10.1038/nature06162). This receptor, OR7D4 (Genbank accession number EU49291), is a very narrowly tuned receptor and responds to a very limited number of compounds such as, for example, androstenone and androstadienone. Keller et al. found that there is a strong link between the presence of this receptor in an individual's genome and their ability to perceive androstenone. The ability to reduce the sensitivity of this receptor to androstenone would be of value in counteracting sweat or urine malodour perception and in the detection of boar flavour in pork. Therefore, compounds that would block or reduce the interaction of OR7D4 with androstenone, androstadienone or any other OR7D4 activator, would likely be efficient to achieve this counteracting task.

It is known that one molecule can block the ability of another to activate a receptor. This phenomenon is known as antagonism and one early example of its occurrence in the field of olfaction was reported by Bell et al. (G. A. Bell, D. G. Laing and H. Panhuber, *Brain Res.*, 1987, 426, 8-18) who used deoxyglucose measurement in the olfactory bulb as a measure of activation of neurons and found that one odorant could reduce the sensitivity of rat olfactory neurons, hence olfactory receptors, to another. The pairs studied correlated with sensory effects shown in humans.

Since then a number of examples of antagonism of olfactory receptors have been reported. Spehr et al. found that undecanal antagonises OR1D2 and prevents it from recognising Bourgeonal (M. Spehr, G. Gisselmann, A. Poplawski, J. A. Riffell, C. H. Wetzel, R. K. Zimmer, H. Hatt, *Science*, 2003, 299, 2054-2058) and later Brodin et al. found that this receptor effect translates into a sensory one (M. Brodin, M. Laska and M. J. Olsson, *Chem. Senses*, 2009, 34 (7), 625-630 doi: 10.1093/chemse/bjp044.).

Oka et al. reported antagonism of the response to eugenol of the mouse receptor mOREG by methylisoeugenol and isosafrole (Y. Oka, M. Omura, H. Kataoka and K. Touhara, *EMBO J.*, 2004, 23 (1), 120-126). In a later paper, they reported that a degradation product of isoeugenol, which they identified in stored samples of isoeugenol, is also an antagonist of mOREG. (Y. Oka, A. Nakamura, H. Watanabe and K. Touhara, *Chem. Senses*, 2004, 29, 815-822 doi: 10.1093/chemse/bjh247.) Etter, found that (+)-carvone antagonises the response of mOREG to eugenol (S. Etter, Ph.D. Thesis 3810, École Polytechnique Fédérale de Lausanne, 2007.). Sanz et al. found that the broadly tuned receptor OR1 G1 was antagonised by 1-hexanol, hexanal and cyclohexanone. G. Sanz, C. Schlegel, J.-C, Pernollet, and L. Briand *Chem. Senses*, 2005, 30, 69-80, doi: 10.1093/chemse/bji002. Isewka found that cinnamyl alcohol and 2-phenylethanol are antagonists of the rat receptor OR5 and that the human receptor OR17-4 is antagonised by 2-methylcyclohexanone, 2-phenylethyl acetate and valeric acid (P. Isewka, Ph.D. Thesis 3668, École Polytechnique Fédérale de Lausanne, 2006.), Peterlin et al. investigated the effect of a series of aldehydes on the mouse ORI7 receptor using octanal as ligand and found that 3-cyclopentylpropanal, 2-cyclohexylacetaldehyde and cycloheptanecarboxaldehyde functioned as antagonists (Z. Peterlin, Y. Li. G. Sun, R. Shah, S. Firestein and K. Ryan, Cell, *Chemistry and Biology*, 2008, 1317-1327).

In all of these examples, the antagonists possess odours. However, when used in perfumery or more generally in the field of flavours and fragrances, an antagonist should preferably be odourless or at least have a low odour profile. Indeed, an odourless molecule blocking the perception of a malodour could be introduced in a perfume or a fragrance without modifying the general odour quality of this perfume or fragrance. It would therefore leave a greater degree of freedom to perfumer to create new fragrances. In addition, an odourless blocker could be used in different situations where the malodour to be blocked is involved since it does not bring any additional odour note. For example, androstenone is a malodour molecule produced in human sweat but is also responsible of a malodour that taints the male pig urine and the male pork meat. Therefore, a blocker having a flower note could be used in a perfume or an air freshener but would not be suitable as a food additive aiming to counteract the boar flavour of pork meat.

To date, no antagonist has been reported for the androstenone receptor OR7D4.

SUMMARY OF THE INVENTION

The present inventors have now discovered a series of compounds that function as antagonists of OR7D4 and have further found that this antagonism results in a sensory effect. Thus the use of the compounds of the invention together with androstenone significantly reduces or eliminates the olfactory perception of androstenone.

According to a first aspect of the present invention, a compound of formula (I), or a stereoisomer thereof, is provided

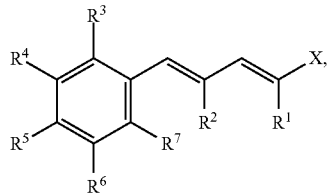
(I)

wherein

X is selected from the group consisting of —C(=O)OR$^8$, cyano, —C(=O)—C$_{1-6}$alkyl, —C(=O)—NR$^9$R$^{10}$, hydroxyC$_{1-6}$alkyl, —C(=O)H, and C$_{1-6}$alkoxyC$_{1-6}$alkyl;

R$^1$ is hydrogen or C$_{1-6}$alkyl;

R$^2$ is hydrogen or a group selected from C$_{1-7}$alkyl and C$_{2-7}$alkenyl, each group being optionally substituted with one or more C$_{3-6}$cycloalkyl;

R$^3$ is selected from the group consisting of hydrogen, halo, C$_{1-6}$alkyl, C$_{1-6}$alkoxy, C$_{1-6}$alkoxyC$_{1-6}$alkyl, and cyano;

R$^4$ is selected from the group consisting of hydrogen, halo, C$_{1-6}$alkyl, C$_{1-6}$alkoxy, C$_{1-6}$alkoxyC$_{1-6}$alkyl, and cyano;

R$^5$ is selected from the group consisting of hydrogen, halo, C$_{1-6}$alkyl, C$_{1-6}$alkoxy, C$_{1-6}$alkoxyC$_{1-6}$alkyl, and cyano;

R$^6$ is selected from the group consisting of hydrogen, halo, C$_{1-6}$alkyl, C$_{1-6}$alkoxy, C$_{1-6}$alkoxyC$_{1-6}$alkyl, and cyano;

R$^7$ is selected from the group consisting of hydrogen, halo, C$_{1-6}$alkyl, C$_{1-6}$alkoxy, C$_{1-6}$alkoxyC$_{1-6}$alkyl, and cyano;

R$^8$ is hydrogen or C$_{1-6}$alkyl;

R$^9$ is hydrogen or C$_{1-6}$alkyl; and

R$^{10}$ is hydrogen or C$_{1-6}$alkyl;

with the following provisos:

when R$^1$=R$^2$=hydrogen, then R$^3$ is selected from C$_{3-6}$alkyl, C$_{1-6}$alkoxy, and C$_{1-6}$alkoxyC$_{1-6}$alkyl;

when X is —C(=O)—NR$^9$R$^{10}$ then R$^1$ is —CH$_3$;

when R$^3$=R$^4$=R$^6$=R$^7$=hydrogen, then R$^2$ is selected from the group consisting of C$_{3-7}$alkyl and C$_{2-7}$alkenyl, each group being optionally substituted by one or more C$_{3-6}$cycloalkyl;

when X is —C(=O)H or —C(=O)OR$^8$, then R$^4$ is not C$_{1-6}$alkoxy;

and the compound of formula (I) is none of:

methyl (2E,4E)-4-(4-fluorobenzylidene)-2-nonenoate;
methyl 4-benzyliden-2-heptenoate;
(2E,4Z)-4-benzylidene-2-methyldec-2-en-1-ol;
(3E,5E)-5-methyl-6-(m-tolyl)hexa-3,5-dien-2-one;
methyl (2E,4E)-4-benzylidenehept-2-enoate;
methyl (2E,4E)-4-[(4-methoxyphenyl)methylene]non-2-enoate; and
(2E,4E)-4-benzylidenedec-2-enenitrile.

According to a second aspect of the present invention, a process is provided for the preparation of a compound of formula (I) according to the first aspect of the invention, comprising the steps of (a) coupling a compound of a formula A with a compound of formula B thereby obtaining a compound of formula C, and

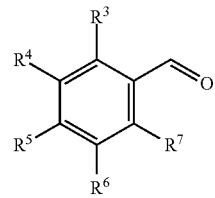
A

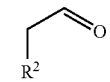
B

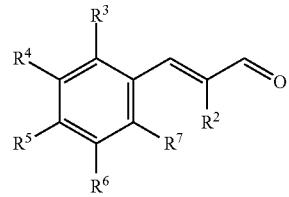
C (b1) contacting compound of formula C with phosphorane derivatives D thereby obtaining compound of formula (I);

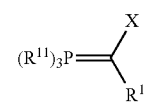
D or (b2) contacting compound of formula C phosphonate derivative F thereby obtaining compound of formula (I)

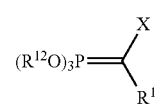
F

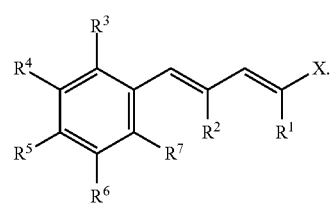
(I)

wherein R$^1$, R$^2$, R$^3$, R$^4$, R$^5$, R$^6$, R$^7$, and X have the same meaning as that defined herein; R$^{11}$ is C$_{1-12}$alkyl, or C$_{6-12}$aryl; and R$^{12}$ is C$_{1-12}$alkyl.

In a third aspect, the present invention also encompasses the use of a compound of formula (I) to suppress or attenuate undesirable odour; preferably body malodour, more preferably mammalian body malodour;

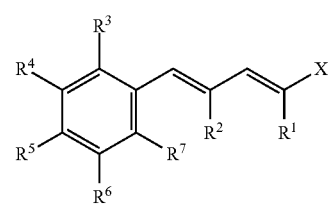
(I)

wherein

X is selected from the group consisting of —C(=O)OR$^8$, cyano, —C(=O)—C$_{1-6}$alkyl, —C(=O)—NR$^9$R$^{10}$, hydroxyC$_{1-6}$alkyl, —C(=O)H, and C$_{1-6}$alkoxyC$_{1-6}$alkyl;

$R^1$ is hydrogen or $C_{1-6}$alkyl;
$R^2$ is hydrogen or a group selected from $C_{1-7}$alkyl, and $C_{2-7}$alkenyl, each group being optionally substituted with one or more $C_{3-6}$cycloalkyl;
$R^3$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^4$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^5$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^6$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^7$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^8$ is hydrogen or $C_{1-6}$alkyl;
$R^9$ is hydrogen or $C_{1-6}$alkyl; and
$R^{10}$ is hydrogen or $C_{1-6}$alkyl;
with the proviso that the compound of formula (I) is not (2E,4Z)-4-benzylidene-2-methyldec-2-en-1-ol.

In a fourth aspect, the present invention also encompasses the use, preferably the non-therapeutic use of a compound according to the first aspect of the invention or methyl (2E,4E)-4-(4-fluorobenzylidene)-2-nonenoate as antagonists of OR7D4.

In a fifth aspect, the present invention also encompasses a consumer product comprising a compound according to the first aspect of the invention.

In a sixth aspect, the present invention also encompasses a method to suppress or attenuate undesirable odour, preferably body malodour, more preferably mammalian body malodour, preferably human axillary malodour, said method comprising the step of applying a malodour counteracting effective amount of a compound of formula (I) to the skin,

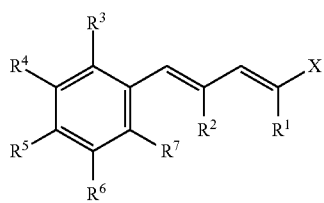

(I)

wherein
X is selected from the group consisting of —C(=O)OR$^8$, cyano, —C(=O)—C$_{1-6}$alkyl, —C(=O)—NR$^9$R$^{10}$, hydroxyC$_{1-6}$alkyl, —C(=O)H, and C$_{1-6}$alkoxyC$_{1-6}$alkyl;
$R^1$ is hydrogen or $C_{1-6}$alkyl;
$R^2$ is hydrogen or a group selected from $C_{1-7}$alkyl, and $C_{2-7}$alkenyl, each group being optionally substituted with one or more $C_{3-6}$cycloalkyl;
$R^3$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^4$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^5$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^6$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^7$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^8$ is hydrogen or $C_{1-6}$alkyl;
$R^9$ is hydrogen or $C_{1-6}$alkyl; and
$R^{10}$ is hydrogen or $C_{1-6}$alkyl;
with the proviso that said compound of formula (I) is not (2E,4Z)-4-benzylidene-2-methyldec-2-en-1-ol.

In a seventh aspect, the present invention also encompasses a method of counteracting malodour in an air space or a substrate comprising the step of introducing a malodour counteracting effective amount of a compound of formula (I)

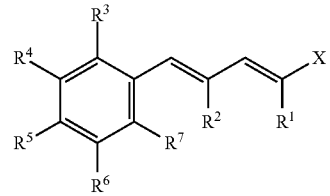

(I)

wherein
X is selected from the group consisting of —C(=O)OR$^8$, cyano, —C(=O)—C$_{1-6}$alkyl, —C(=O)—NR$^9$R$^{10}$, hydroxyC$_{1-6}$alkyl, —C(=O)H, and C$_{1-6}$alkoxyC$_{1-6}$alkyl;
$R^1$ is hydrogen or $C_{1-6}$alkyl;
$R^2$ is hydrogen or a group selected from $C_{1-7}$alkyl, and $C_{2-7}$alkenyl, each group being optionally substituted with one or more $C_{3-6}$cycloalkyl;
$R^3$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^4$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^5$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^6$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^7$ is selected from the group consisting of hydrogen, halo, $C_{1-6}$alkyl, $C_{1-6}$alkoxy, halo$C_{1-6}$alkyl, halo$C_{1-6}$alkoxy, $C_{1-6}$alkoxy$C_{1-6}$alkyl, and cyano;
$R^8$ is hydrogen or $C_{1-6}$alkyl;
$R^9$ is hydrogen or $C_{1-6}$alkyl; and
$R^{10}$ is hydrogen or $C_{1-6}$alkyl;
with the proviso that said compound of formula (I) is not (2E,4Z)-4-benzylidene-2-methyldec-2-en-1-ol.

The independent and dependent claims and statements set out particular and preferred features of the invention. Features from the dependent claims and statements may be combined with features of the independent or other dependent claims and statement as appropriate.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

Before the present invention is described, it is to be understood that this invention is not limited to particular compounds, methods, and processes described, as such compounds, methods, and processes may, of course, vary. It is also to be understood that the terminology used herein is not intended to be limiting, since the scope of the present invention will be limited only by the appended claims.

When describing the compounds and processes of the invention, the terms used are to be construed in accordance with the following definitions, unless a context dictates otherwise.

As used in the specification and the appended claims, the singular forms "a", "an," and "the" include both singular and plural referents unless the context clearly dictates otherwise. By way of example, "a compound" means one compound or more than one compound.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

As used herein, the term "and/or," when used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims and statements, any of the embodiments can be used in any combination.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

When describing the present invention, the terms used are to be construed in accordance with the following definitions, unless a context dictates otherwise.

Whenever the term "substituted" is used herein, it is meant to indicate that one or more hydrogen atoms on the atom indicated in the expression using "substituted" is replaced with a selection from the indicated group, provided that the indicated atom's normal valence is not exceeded, and that the substitution results in a chemically stable compound, i.e. a compound that is sufficiently robust to survive isolation from a reaction mixture.

The term "halo" or "halogen" as a group or part of a group is generic for fluoro, chloro, bromo, iodo.

The term "hydroxyl" or "hydroxy" as used herein refers to the group —OH.

The term "cyano" as used herein refers to the group —C≡N.

The term "$C_{1-12}$alkyl", as a group or part of a group, refers to a hydrocarbyl group of formula —$C_nH_{2n+1}$ wherein n is a number ranging from 1 to 12. Alkyl groups may be linear or branched and may be substituted as indicated herein. Thus, for example, "$C_{1-6}$alkyl" includes all linear or branched alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers. For example, "$C_{1-5}$alkyl" includes all includes all linear or branched alkyl groups with between 1 and 5 carbon atoms, and thus includes methyl, ethyl, n-propyl, i-propyl, butyl and its isomers (e.g. n-butyl, i-butyl and t-butyl); pentyl and its isomers. For example, "$C_{1-4}$alkyl" includes all linear or branched alkyl groups with between 1 and 4 carbon atoms, and thus includes methyl, ethyl, n-propyl, i-propyl, butyl and its isomers (e.g. n-butyl, i-butyl and t-butyl). For example "$C_{1-3}$alkyl" includes all linear or branched alkyl groups with between 1 and 3 carbon atoms, and thus includes methyl, ethyl, n-propyl, i-propyl.

The term "hydroxy$C_{1-6}$alkyl" as a group or part of a group, refers to a $C_{1-6}$alkyl group having the meaning as defined above wherein one or more hydrogen atoms are each replaced with one or more hydroxyl as defined herein. Non-limiting examples of hydroxy$C_{1-6}$alkyl group include hydroxymethyl, hydroxyethyl, and the like.

The term "halo$C_{1-6}$alkyl" as a group or part of a group, refers to a $C_{1-6}$alkyl group having the meaning as defined above wherein one or more hydrogen atoms are each replaced with one or more halogen as defined herein. Non-limiting examples of such halo$C_{1-6}$alkyl groups include chloromethyl, 1-bromoethyl, fluoromethyl, difluoromethyl, trifluoromethyl, 1,1,1-trifluoroethyl and the like.

The term "$C_{1-6}$alkoxy", as a group or part of a group, refers to a group having the formula —$OR^b$ wherein $R^b$ is $C_{1-6}$alkyl as defined herein above. Non-limiting examples of suitable $C_{1-6}$alkoxy include methoxy, ethoxy, propoxy, isopropoxy, butoxy, isobutoxy, sec-butoxy, tert-butoxy, pentyloxy and hexyloxy.

The term "$C_{1-6}$alkoxy$C_{1-6}$alkyl", as a group or part of a group, refers to a group having the formula —$R^a$—$OR^b$ wherein $R^a$ is $C_{1-6}$alkylene and $R^b$ is $C_{1-6}$alkyl as defined herein above.

The term "halo$C_{1-6}$alkoxy", as a group or part of a group, refers to a group of formula —O—$R^c$ wherein $R^c$ is halo$C_{1-6}$alkyl as defined herein. Non-limiting examples of suitable halo$C_{1-6}$alkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy, trichloromethoxy, 2-bromoethoxy, pentafluoroethyl, 3,3,3-trichloropropoxy, 4,4,4-trichlorobutoxy.

The term "$C_{2-7}$alkenyl" as a group or part of a group, refers to an unsaturated hydrocarbyl group, which may be linear, or branched, comprising one or more carbon-carbon double bonds, and comprising from 2 to 7 carbon atoms. Examples of $C_{2-7}$alkenyl groups are ethenyl, 2-propenyl, 2-butenyl, 3-butenyl, 2-pentenyl and its isomers, 2-hexenyl and its isomers, 2,4-pentadienyl, and the like.

The term "$C_{3-6}$cycloalkyl", as a group or part of a group, refers to a cyclic alkyl group, that is a monovalent, saturated, hydrocarbyl group having 1 or more cyclic structure, and comprising from 3 to 6 carbon atoms, preferably from 5 to 6 carbon atoms. Cycloalkyl includes all saturated hydrocarbon groups containing one or more rings, including monocyclic or bicyclic groups. The further rings of multi-ring cycloalkyls may be either fused, bridged and/or joined through one or more spiro atoms. Examples of $C_{3-6}$cycloalkyl groups include but are not limited to cyclopropyl, cyclobutyl, cyclopentyl, and cyclohexyl.

The term "$C_{6-12}$aryl", as a group or part of a group, refers to a polyunsaturated, aromatic hydrocarbyl group having a single ring (i.e. phenyl) or multiple aromatic rings fused together (e.g. naphthyl), or linked covalently, typically comprising 6 to 12 carbon atoms; wherein at least one ring is aromatic, preferably comprising 6 to 10 carbon atoms, wherein at least one ring is aromatic. The aromatic ring may optionally include one to two additional rings (either cycloalkyl, heterocyclyl or heteroaryl) fused thereto. Examples of suitable aryl include $C_{6-10}$aryl, more preferably $C_{6-8}$aryl. Non-limiting examples of $C_{6-12}$aryl comprise phenyl, biphenylyl, biphenylenyl, or 1- or 2-naphthanelyl; 5- or 6-tetralinyl, 1-, 2-, 3-, 4-, 5-, 6-, 7- or 8-azulenyl, 4-, 5-, 6 or 7-indenyl, 4- or 5-indanyl, 5-, 6-, 7- or 8-tetrahydronaphthyl, 1,2,3,4-tetrahydronaphthyl, and 1,4-dihydronaphthyl; 1-, 2-, 3-, 4- or 5-pyrenyl.

Whenever used in the present invention the term "compounds of the invention" or a similar term is meant to include the compounds of general formula (I) and any subgroup thereof, including all polymorphs and crystal habits thereof, and isomers thereof (including optical, geometric and tautomeric isomers) as hereinafter defined.

As used herein and unless otherwise stated, the term "stereoisomer" refers to all possible different isomeric as well as conformational forms which the compounds of structural formula herein may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The compounds of formulae (I) or any subgroups thereof comprise alkenyl or alkenylene group, and the geometric cis/trans (or Z/E) isomers are encompassed herein. Where structural isomers are interconvertible via a low energy barrier, tautomeric isomerism ('tautomerism') can occur. This can take the form of proton tautomerism in compounds of formula (I) containing, for example, a keto group, or so-called valence tautomerism in compounds which contain an aromatic moiety. It follows that a single compound may exhibit more than one type of isomerism.

Cis/trans isomers may be separated by conventional techniques well known to those skilled in the art, for example, chromatography and fractional crystallization.

Preferred statements (features) and embodiments of the compounds, methods and uses of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the below numbered aspects and embodiments 1 to 43, with any other statement and/or embodiments.

1. A compound of formula (I) or a stereoisomer thereof,

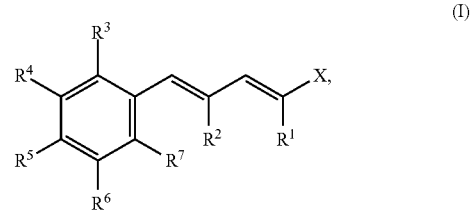

(I)

wherein

X is selected from the group consisting of —C(=O)$OR^8$, cyano, —C(=O)—$C_{1-6}$alkyl, —C(=O)—$NR^9R^{10}$, hydroxy$C_{1-6}$alkyl, —C(=O)H, and $C_{1-6}$alkoxy$C_{1-6}$alkyl;

$R^1$ is hydrogen or $C_{1-6}$alkyl;

$R^2$ is hydrogen or a group selected from $C_{1-7}$alkyl, and $C_{2-7}$alkenyl, each group being optionally substituted with one or more $C_{3-6}$cycloalkyl;

$R^3$ is selected from the group consisting of hydrogen, halo, $C_{1-6}$alkyl, $C_{1-6}$alkoxy, $C_{1-6}$alkoxy$C_{1-6}$alkyl, and cyano;

$R^4$ is selected from the group consisting of hydrogen, halo, $C_{1-6}$alkyl, $C_{1-6}$alkoxy, $C_{1-6}$alkoxy$C_{1-6}$alkyl, and cyano;

$R^5$ is selected from the group consisting of hydrogen, halo, $C_{1-6}$alkyl, $C_{1-6}$alkoxy, $C_{1-6}$alkoxy$C_{1-6}$alkyl, and cyano;

$R^6$ is selected from the group consisting of hydrogen, halo, $C_{1-6}$alkyl, $C_{1-6}$alkoxy, $C_{1-6}$alkoxy$C_{1-6}$alkyl, and cyano;

$R^7$ is selected from the group consisting of hydrogen, halo, $C_{1-6}$alkyl, $C_{1-6}$alkoxy, $C_{1-6}$alkoxy$C_{1-6}$alkyl, and cyano;

$R^8$ is hydrogen or $C_{1-6}$alkyl;
$R^9$ is hydrogen or $C_{1-6}$alkyl;
$R^{10}$ is hydrogen or $C_{1-6}$alkyl;

with the following provisos:
when $R^1=R^2$=hydrogen, then $R^3$ is selected from $C_{3-6}$alkyl, $C_{1-6}$alkoxy, and $C_{1-6}$alkoxy$C_{1-6}$alkyl;
when X is —C(=O)—$NR^9R^{10}$ then $R^1$ is —$CH_3$;
when $R^3=R^4=R^6=R^7$=hydrogen, then $R^2$ is selected from the group consisting of $C_{3-7}$alkyl and $C_{2-7}$alkenyl, each group being optionally substituted by one or more $C_{3-6}$cycloalkyl;
when X is —C(=O)H or —C(=O)$OR^8$, then $R^4$ is not $C_{1-6}$alkoxy;
and the compound of formula (I) is none of:
methyl (2E,4E)-4-(4-fluorobenzylidene)-2-nonenoate;
methyl 4-benzyliden-2-heptenoate;
(2E,4Z)-4-benzylidene-2-methyldec-2-en-1-ol;
(3E,5E)-5-methyl-6-(m-tolyl)hexa-3,5-dien-2-one;
methyl (2E,4E)-4-benzylidenehept-2-enoate;
methyl (2E,4E)-4-[(4-methoxyphenyl)methylene]non-2-enoate; and
(2E,4E)-4-benzylidenedec-2-enenitrile.

2. The compound according to statement 1, wherein the compound does not exceed 24 carbon atoms, preferably the compound has less than 22 carbon atoms.

3. The compound according to any one of statements 1 to 2, wherein
X is selected from the group consisting of —C(=O)$OC_{1-4}$ alkyl, cyano, —C(=O)—OH, —C(=O)—$C_{1-4}$ alkyl, —C(=O)—$NH_2$, —C(=O)—$NHC_{1-4}$alkyl, —C(=O)—$N(C_{1-4}$alkyl$)_2$, hydroxy$C_{1-4}$alkyl, —C(=O)H, and $C_{1-4}$alkoxy$C_{1-4}$alkyl;
$R^1$ is hydrogen or $C_{1-4}$alkyl;
$R^2$ is hydrogen or a group selected from $C_{2-7}$alkyl and $C_{2-6}$alkenyl, each group being optionally substituted with one or more $C_{3-6}$cycloalkyl;
$R^3$ is selected from the group consisting of hydrogen, halo, $C_{1-6}$alkyl, $C_{1-4}$alkoxy, $C_{1-4}$alkoxy$C_{1-4}$alkyl, and cyano;
$R^4$ is selected from the group consisting of hydrogen, halo, $C_{1-6}$alkyl, $C_{1-4}$alkoxy, $C_{1-4}$alkoxy$C_{1-4}$alkyl, and cyano;
$R^5$ is selected from the group consisting of hydrogen, halo, $C_{1-6}$alkyl, $C_{1-4}$alkoxy, $C_{1-4}$alkoxy$C_{1-4}$alkyl, and cyano;
$R^6$ is selected from the group consisting of hydrogen, halo, $C_{1-6}$alkyl, $C_{1-4}$alkoxy, $C_{1-4}$alkoxy$C_{1-4}$alkyl, and cyano; and
$R^7$ is selected from the group consisting of hydrogen, halo, $C_{1-6}$alkyl, $C_{1-4}$alkoxy, $C_{1-4}$alkoxy$C_{1-4}$alkyl, and cyano.

4. The compound according to any one of statements 1 to 3, wherein
X is selected from the group consisting of —C(=O)$OC_{1-2}$ alkyl, cyano, —C(=O)OH, C(=O)—$C_{1-2}$alkyl, —C(=O)—$NH_2$, —C(=O)—$NHC_{1-2}$alkyl, —C(=O)—$N(CH_3)_2$), hydroxy$C_{1-2}$alkyl, —C(=O)H, and $C_{1-2}$alkoxy$C_{1-2}$alkyl;
$R^1$ is hydrogen or $C_{1-2}$alkyl;
$R^2$ is hydrogen or a group selected from $C_{2-7}$alkyl and $C_{3-6}$alkenyl, each group being optionally substituted with one or more $C_{5-6}$cycloalkyl;
$R^3$ is selected from the group consisting of hydrogen, fluoro, chloro, $C_{1-6}$alkyl, $C_{1-2}$alkoxy, $C_{1-2}$alkoxy$C_{1-2}$ alkyl, and cyano;
$R^4$ is selected from the group consisting of hydrogen, fluoro, chloro, $C_{1-6}$alkyl, $C_{1-2}$alkoxy, $C_{1-2}$alkoxy$C_{1-2}$ alkyl, and cyano;
$R^5$ is selected from the group consisting of hydrogen, fluoro, chloro, $C_{1-6}$alkyl, $C_{1-2}$alkoxy, $C_{1-2}$alkoxy$C_{1-2}$ alkyl, and cyano;
$R^6$ is selected from the group consisting of hydrogen, fluoro, chloro, $C_{1-6}$alkyl, $C_{1-2}$alkoxy, $C_{1-2}$alkoxy$C_{1-2}$ alkyl, and cyano; and
$R^7$ is selected from the group consisting of hydrogen, fluoro, chloro, $C_{1-6}$alkyl, $C_{1-2}$alkoxy, $C_{1-2}$alkoxy$C_{1-2}$ alkyl, and cyano.

5. The compound according to any one of statements 1 to 4, wherein
X is selected from the group consisting of —C(=O)—O—$CH_3$, cyano, —C(=O)—O—$CH_2$—$CH_3$, —C(=O)OH, —C(=O)—$CH_3$, —C(=O)—$CH_2$—$CH_3$, —C(=O)—$NH_2$, —C(=O)—NH—$CH_3$, —C(=O)—N($CH_3)_2$, —$CH_2$—OH, —$CH_2$—$CH_2$—OH, —C(=O)H, and —$CH_2$—O—$CH_3$, —$CH_2$—O—$CH_2$—$CH_3$;
$R^1$ is hydrogen or —$CH_3$;
$R^2$ is hydrogen or a group selected from $C_{2-7}$alkyl and $C_{5-6}$alkenyl, each group being optionally substituted with one or more $C_{5-6}$cycloalkyl;
$R^3$ is selected from the group consisting of hydrogen, fluoro, chloro, $C_{1-6}$alkyl, $C_{1-2}$alkoxy, $C_{1-2}$alkoxy$C_{1-2}$ alkyl, and cyano;
$R^4$ is selected from the group consisting of hydrogen, fluoro, chloro, $C_{1-6}$alkyl, $C_{1-2}$alkoxy, $C_{1-2}$alkoxy$C_{1-2}$ alkyl, and cyano;
$R^5$ is selected from the group consisting of hydrogen, fluoro, chloro, $C_{1-6}$alkyl, $C_{1-2}$alkoxy, $C_{1-2}$alkoxy$C_{1-2}$ alkyl, and cyano;
$R^6$ is selected from the group consisting of hydrogen, fluoro, chloro, $C_{1-6}$alkyl, $C_{1-2}$alkoxy, $C_{1-2}$alkoxy$C_{1-2}$ alkyl, and cyano; and
$R^7$ is selected from the group consisting of hydrogen, fluoro, chloro, $C_{1-6}$alkyl, $C_{1-2}$alkoxy, $C_{1-2}$alkoxy$C_{1-2}$ alkyl, and cyano.

6. The compound according to any one of statements 1 to 2, wherein
X is selected from the group consisting of —C(=O)$OR^8$, cyano, —C(=O)—$C_{1-6}$alkyl, —C(=O)—$NR^9R^{10}$, —C(=O)H, and $C_{1-6}$alkoxy$C_{1-6}$alkyl;
$R^1$ is hydrogen or $C_{1-6}$alkyl;
$R^2$ is hydrogen or a group selected from $C_{1-7}$alkyl, and $C_{2-7}$alkenyl, each group being optionally substituted with one or more $C_{3-6}$cycloalkyl;
$R^3$ is selected from the group consisting of hydrogen, halo, $C_{1-6}$alkyl, $C_{1-6}$alkoxy, $C_{1-6}$alkoxy$C_{1-6}$alkyl, and cyano;
$R^4$ is selected from the group consisting of hydrogen, halo, $C_{1-6}$alkyl, $C_{1-6}$alkoxy, $C_{1-6}$alkoxy$C_{1-6}$alkyl, and cyano;
$R^5$ is selected from the group consisting of hydrogen, halo, $C_{1-6}$alkyl, $C_{1-6}$alkoxy, $C_{1-6}$alkoxy$C_{1-6}$alkyl, and cyano;
$R^6$ is selected from the group consisting of hydrogen, halo, $C_{1-6}$alkyl, $C_{1-6}$alkoxy, $C_{1-6}$alkoxy$C_{1-6}$alkyl, and cyano;
$R^7$ is selected from the group consisting of hydrogen, halo, $C_{1-6}$alkyl, $C_{1-6}$alkoxy, $C_{1-6}$alkoxy$C_{1-6}$alkyl, and cyano;
$R^8$ is hydrogen or $C_{1-6}$alkyl;
$R^9$ is hydrogen or $C_{1-6}$alkyl;
$R^{10}$ is hydrogen or $C_{1-6}$alkyl.

7. The compound according to any one of statements 1 to 2, 6, wherein
X is selected from the group consisting of —C(=O)OC$_{1-4}$ alkyl, cyano, —C(=O)—OH, —C(=O)—C$_{1-4}$ alkyl, —C(=O)—NH$_2$, —C(=O)—NHC$_{1-4}$alkyl, —C(=O)—N(C$_{1-4}$alkyl)$_2$, —C(=O)H, and C$_{1-4}$alkoxyC$_{1-4}$alkyl;
R$^1$ is hydrogen or C$_{1-4}$alkyl;
R$^2$ is hydrogen or a group selected from C$_{2-7}$alkyl and C$_{2-6}$alkenyl, each group being optionally substituted with one or more C$_{3-6}$cycloalkyl;
R$^3$ is selected from the group consisting of hydrogen, halo, C$_{1-6}$alkyl, C$_{1-4}$alkoxy, C$_{1-4}$alkoxyC$_{1-4}$alkyl, and cyano;
R$^4$ is selected from the group consisting of hydrogen, halo, C$_{1-6}$alkyl, C$_{1-4}$alkoxy, C$_{1-4}$alkoxyC$_{1-4}$alkyl, and cyano;
R$^5$ is selected from the group consisting of hydrogen, halo, C$_{1-6}$alkyl, C$_{1-4}$alkoxy, C$_{1-4}$alkoxyC$_{1-4}$alkyl, and cyano;
R$^6$ is selected from the group consisting of hydrogen, halo, C$_{1-6}$alkyl, C$_{1-4}$alkoxy, C$_{1-4}$alkoxyC$_{1-4}$alkyl, and cyano; and
R$^7$ is selected from the group consisting of hydrogen, halo, C$_{1-6}$alkyl, C$_{1-4}$alkoxy, C$_{1-4}$alkoxyC$_{1-4}$alkyl, and cyano.

8. The compound according to any one of statements 1 to 2, 6 to 7, wherein
X is selected from the group consisting of —C(=O)OC$_{1-2}$ alkyl, cyano, —C(=O)OH, C(=O)—C$_{1-2}$alkyl, —C(=O)—NH$_2$, —C(=O)—NHC$_{1-2}$alkyl, —C(=O)—N(CH$_3$)$_2$), —C(=O)H, and C$_{1-2}$alkoxyC$_{1-2}$ alkyl;
R$^1$ is hydrogen or C$_{1-2}$alkyl;
R$^2$ is hydrogen or a group selected from C$_{2-7}$alkyl and C$_{3-6}$alkenyl, each group being optionally substituted with one or more C$_{5-6}$cycloalkyl;
R$^3$ is selected from the group consisting of hydrogen, fluoro, chloro, C$_{1-6}$alkyl, C$_{1-2}$alkoxy, C$_{1-2}$alkoxyC$_{1-2}$ alkyl, and cyano;
R$^4$ is selected from the group consisting of hydrogen, fluoro, chloro, C$_{1-6}$alkyl, C$_{1-2}$alkoxy, C$_{1-2}$alkoxyC$_{1-2}$ alkyl, and cyano;
R$^5$ is selected from the group consisting of hydrogen, fluoro, chloro, C$_{1-6}$alkyl, C$_{1-2}$alkoxy, C$_{1-2}$alkoxyC$_{1-2}$ alkyl, and cyano;
R$^6$ is selected from the group consisting of hydrogen, fluoro, chloro, C$_{1-6}$alkyl, C$_{1-2}$alkoxy, C$_{1-2}$alkoxyC$_{1-2}$ alkyl, and cyano; and
R$^7$ is selected from the group consisting of hydrogen, fluoro, chloro, C$_{1-6}$alkyl, C$_{1-2}$alkoxy, C$_{1-2}$alkoxyC$_{1-2}$ alkyl, and cyano.

9. The compound according to any one of statements 1 to 2, 6 to 8, wherein
X is selected from the group consisting of —C(=O)—O—CH$_3$, cyano, —C(=O)—O—CH$_2$—CH$_3$, —C(=O)OH, —C(=O)—CH$_3$, —C(=O)—CH$_2$—CH$_3$, —C(=O)—NH$_2$, —C(=O)—NH—CH$_3$, —C(=O)—N(CH$_3$)$_2$, —C(=O)H, and —CH$_2$—O—CH$_3$, —CH$_2$—O—CH$_2$—CH$_3$;
R$^1$ is hydrogen or —CH$_3$;
R$^2$ is hydrogen or a group selected from C$_{2-7}$alkyl and C$_{5-6}$alkenyl, each group being optionally substituted with one or more C$_{5-6}$cycloalkyl;
R$^3$ is selected from the group consisting of hydrogen, fluoro, chloro, C$_{1-6}$alkyl, C$_{1-2}$alkoxy, C$_{1-2}$alkoxyC$_{1-2}$ alkyl, and cyano;
R$^4$ is selected from the group consisting of hydrogen, fluoro, chloro, C$_{1-6}$alkyl, C$_{1-2}$alkoxy, C$_{1-2}$alkoxyC$_{1-2}$ alkyl, and cyano;
R$^5$ is selected from the group consisting of hydrogen, fluoro, chloro, C$_{1-6}$alkyl, C$_{1-2}$alkoxy, C$_{1-2}$alkoxyC$_{1-2}$ alkyl, and cyano;
R$^6$ is selected from the group consisting of hydrogen, fluoro, chloro, C$_{1-6}$alkyl, C$_{1-2}$alkoxy, C$_{1-2}$alkoxyC$_{1-2}$ alkyl, and cyano; and
R$^7$ is selected from the group consisting of hydrogen, fluoro, chloro, C$_{1-6}$alkyl, C$_{1-2}$alkoxy, C$_{1-2}$alkoxyC$_{1-2}$ alkyl, and cyano.

10. The compound according to any one of statements 1 to 9, wherein
X is selected from the group consisting of —C(=O)—O—CH$_3$, cyano, —C(=O)—O—CH$_2$—CH$_3$, —C(=O)—CH$_3$, —C(=O)—NH$_2$, —C(=O)—NH—CH$_3$, —C(=O)—N(CH$_3$)$_2$;
R$^1$ is hydrogen or —CH$_3$;
R$^2$ is hydrogen or a group selected from C$_{5-7}$alkyl and C$_{5-6}$alkenyl, each group being optionally substituted with one or more C$_{5-6}$cycloalkyl; wherein at least one of R$^1$ or
R$^2$ is not hydrogen;
R$^3$ is hydrogen;
R$^4$ is hydrogen;
R$^5$ is hydrogen;
R$^6$ is hydrogen; and
R$^7$ is hydrogen.

11. The compound according to any one of statements 1 to 9, selected from the group consisting of:

| Compound | Structure |
| --- | --- |
| 1 | (structure) |
| 3 | (structure) |
| 4 | (structure) |

-continued
| Compound | Structure |
|---|---|
| 5 | 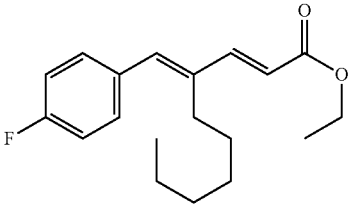 |
| 6 | 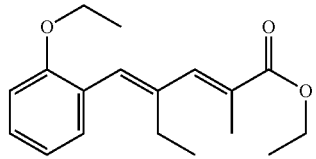 |
| 7 | 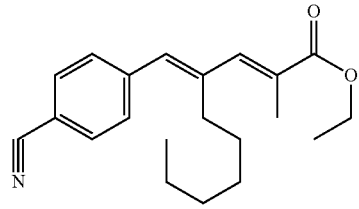 [SMILES: CCCCCCC(=C\c1ccc(C#N)cc1)/C=C(\C)C(=O)OCC] |
| 8 | 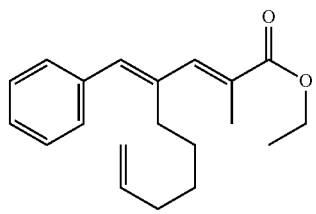 |
| 9 | 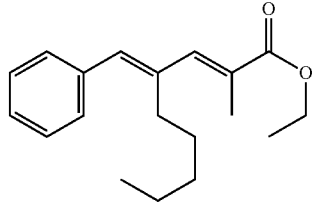 [SMILES: CCCCCC(=C\c1ccccc1)/C=C(\C)C(=O)OCC] |
| 10 | 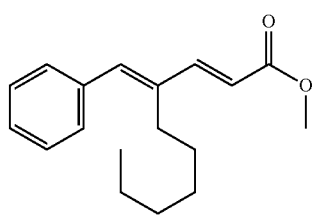 [SMILES: CCCCCCC(/C=C/C(=O)OC)=C\c1ccccc1] |
| 11 | 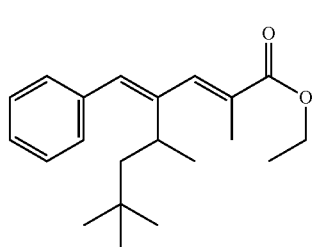 [SMILES: CCOC(=O)/C(C)=C/C(=C/c1ccccc1)C(C)CC(C)(C)C] |
-continued
| Compound | Structure |
|---|---|
| 12 | 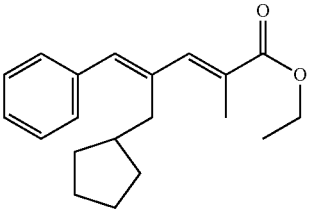 [SMILES: CCOC(=O)/C(C)=C/C(=C/c1ccccc1)CC1CCCC1] |
| 13 | 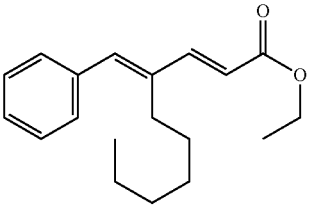 |
| 14 | 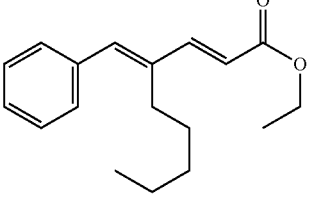 |
| 15 | 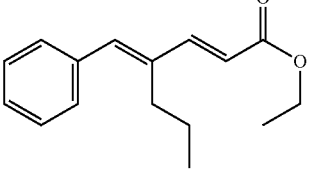 |
| 16 | 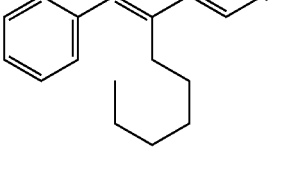 |
| 17 | 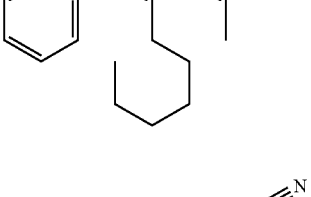 |
| 18 | 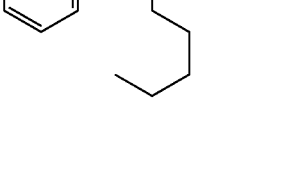 |

-continued

| Compound | Structure |
|---|---|
| 19 | (4-cyanophenyl-substituted diene with methyl, pentyl, and carboxylic acid) |
| 20 | (2-ethoxyphenyl-substituted diene with ethyl branch, methyl, and carboxylic acid) |
| 21 | (phenyl-substituted diene with pentyl branch, methyl, and carboxylic acid) |
| 22 | (phenyl-substituted diene with pentyl branch and carboxylic acid) |
| 23 | (phenyl-substituted diene with pentyl branch, methyl, and primary amide) |
| 24 | (phenyl-substituted diene with pentyl branch, methyl, and N-methyl amide) |
| 26 | (phenyl-substituted diene with butyl branch, methyl, and primary amide) |

-continued

| Compound | Structure |
|---|---|
| 28 | (phenyl-substituted diene with pentyl branch, methyl, and N,N-dimethyl amide) |
| 29 | (phenyl-substituted diene with hexyl branch, methyl, and methyl ketone) |
| 30 | (phenyl-substituted diene with hexyl branch and methyl ketone) |
| 31 | (3-methoxyphenyl-substituted diene with methyl and allylic alcohol) |
| 32 | (2-propylphenyl-substituted diene with allylic alcohol) |
| 33 | (4-fluorophenyl-substituted diene with pentyl branch and allylic alcohol) |
| 34 | (phenyl-substituted diene with butyl branch, methyl, and allylic alcohol) |
| 35 | (phenyl-substituted diene with propyl branch, methyl, and allylic alcohol) |

| Compound | Structure |
|---|---|
| 36 | (3-methoxyphenyl)-substituted pentadienal with methyl group |
| 37 | (2-ethylphenyl)-substituted pentadienal |
| 38 | (4-fluorophenyl)-substituted benzylidene with hexyl chain, dienal |
| 39 | phenyl benzylidene with hexyl chain, dienal |
| 40 | phenyl benzylidene with hexyl chain, methyl-dienal |
| 41 | phenyl benzylidene with propyl chain, methyl-dienal |
| 42 | phenyl benzylidene with hexyl chain, methyl, methoxy ether |
| 43 | phenyl benzylidene with hexyl chain, methyl, ethoxy ether |
| 44 | (4-fluorophenyl) benzylidene with pentyl chain, methyl, ethoxy ether |
| 45 | (4-fluorophenyl) benzylidene with pentyl chain, ethyl ester |

12. A compound selected from the group consisting of:

| Compound | Structure |
|---|---|
| 25 | (3-ethylphenyl) benzylidene-methyl-dienyl-N,N-dimethylamide |
| 27 | phenyl benzylidene with hexyl chain, dienamide |

13. A compound selected from the group consisting of the compounds listed in Table 1.

14. The compound according to statement 1 corresponding to ethyl (E)-4-((E)-benzylidene)-2-methyl-dec-2-enoate 15. The compound according to statement 1 corresponding to 4-benzylidenedec-2-enonitrile

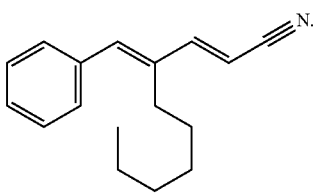 [SMILES: CCCCCCC(/C=C/C#N)=C\c1ccccc1]

16. The compound according to statement 1 corresponding to 5-benzylidene-3-methyldec-3-en-2-one

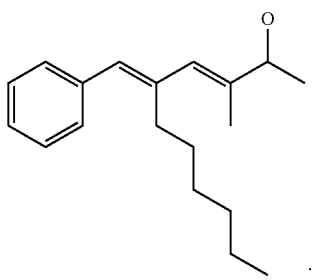 [SMILES: CCCCCCC(=C\c1ccccc1)/C=C(\C)C(C)O]

17. The compound according to statement 1 corresponding to ethyl 4-benzylidene-2-methyl-(2E,9)-decadienoate

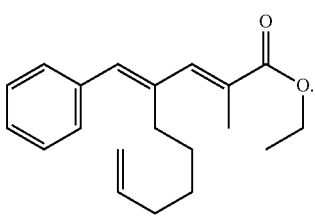 [SMILES: C=CCCCCC(=C\c1ccccc1)/C=C(\C)C(=O)OCC]

18. The compound according to statement 1 corresponding to ethyl 4-benzylidene-(2,5,7,7)-tetramethyloct-2-enoate

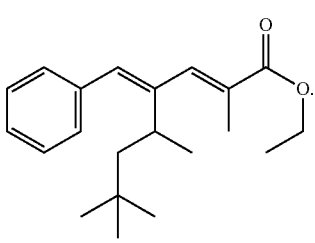 [SMILES: CCOC(=O)/C(C)=C/C(=C/c1ccccc1)C(C)CC(C)(C)C]

19. The compound according to statement 1 corresponding ethyl 5-benzyl-4-methylcyclopentyl-2-methyl-penta-(2,4)-dienoate

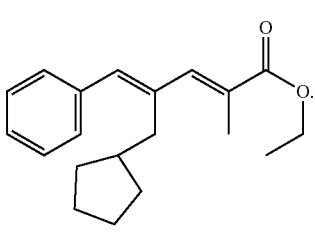 [SMILES: CCOC(=O)/C(C)=C/C(=C/c1ccccc1)CC1CCCC1]

20. Process for the preparation of a compound according to any one of statements 1 to 19, comprising the steps of
(a) coupling a compound of a formula A with a compound of formula B thereby obtaining a compound of formula C, and

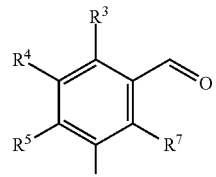

A

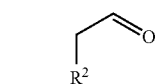

B

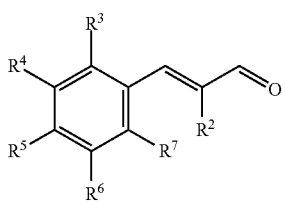

C (b1) contacting compound of formula C with phosphorane derivatives D thereby obtaining compound of formula (I);

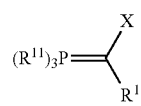

D or (b2) contacting compound of formula C phosphonate derivative F thereby obtaining compound of formula (I),

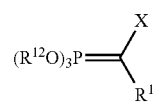

F

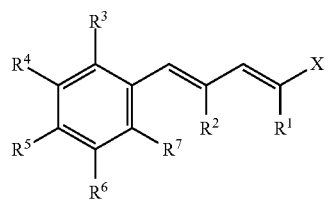

(I)

wherein $R^1$, $R^2$, $R^3$, $R^4$, $R^5$, $R^6$, $R^7$, and X have the same meaning as that defined in any one of statements 1 to 19; $R^{11}$ is $C_{1-12}$alkyl, or $C_{6-12}$aryl; preferably $C_{1-5}$alkyl or phenyl, and $R^{12}$ is $C_{1-12}$alkyl, preferably $C_{1-5}$alkyl.

21. Use of a compound of formula (I) to suppress or attenuate undesirable odour; preferably body malodour, more preferably mammalian body malodour,

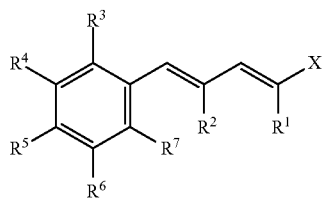

(I)

wherein

X is selected from the group consisting of —C(=O)OR$^8$, cyano, —C(=O)—C$_{1-6}$alkyl, —C(=O)—NR$^9$R$^{10}$, hydroxyC$_{1-6}$alkyl, —C(=O)H, and C$_{1-6}$alkoxyC$_{1-6}$alkyl;

R$^1$ is hydrogen or C$_{1-6}$alkyl;

R$^2$ is hydrogen or a group selected from C$_{1-7}$alkyl, and C$_{2-7}$alkenyl, each group being optionally substituted with one or more C$_{3-6}$cycloalkyl;

R$^3$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;

R$^4$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;

R$^5$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;

R$^6$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;

R$^7$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;

R$^8$ is hydrogen or C$_{1-6}$alkyl;

R$^9$ is hydrogen or C$_{1-6}$alkyl; and

R$^{10}$ is hydrogen or C$_{1-6}$alkyl;

with the proviso that the compound of formula (I) is not (2E,4Z)-4-benzylidene-2-methyldec-2-en-1-ol.

22. The use according to statement 21, wherein said compound is a compound as defined in any one of statements 1 to 19.

23. A method to suppress or attenuate undesirable odour, comprising the step of using a compound of formula (I) or a stereoisomer thereof to;

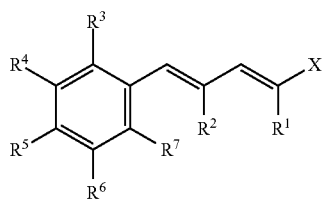

(I)

wherein

X is selected from the group consisting of —CN, —C(=O)OR$^8$, —C(=O)—C$_{1-6}$alkyl, —C(=O)—NR$^9$R$^{10}$, hydroxyC$_{1-6}$alkyl, —C(=O)H, and C$_{1-6}$alkoxyC$_{1-6}$alkyl;

R$^1$ is hydrogen or C$_{1-6}$alkyl;

R$^2$ is hydrogen or a group selected from C$_{1-7}$alkyl, and C$_{2-7}$alkenyl, each group being optionally substituted with one or more C$_{3-6}$cycloalkyl;

R$^3$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;

R$^4$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;

R$^5$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;

R$^6$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;

R$^7$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;

R$^8$ is hydrogen or C$_{1-6}$alkyl;

R$^9$ is hydrogen or C$_{1-6}$alkyl; and

R$^{10}$ is hydrogen or C$_{1-6}$alkyl;

with the proviso that the compound of formula (I) is not (2E,4Z)-4-benzylidene-2-methyldec-2-en-1-ol.

24. The method according to statement 23, wherein said compound is a compound as defined in any one of statements 1 to 19.

25. A compound according to any one of statements 1 to 19 or methyl (2E,4E)-4-(4-fluorobenzylidene)-2-nonenoate for use as antagonists of OR7D4, preferably wherein said use is non-therapeutic.

26. Use of a compound according to any one of statements 1 to 19 or methyl (2E,4E)-4-(4-fluorobenzylidene)-2-nonenoate as antagonists of OR7D4, preferably wherein said use is non-therapeutic.

27. A consumer product comprising a compound according to any one of the statements 1 to 19.

28. A consumer product as defined in statement 27 for use on the skin.

29. A consumer product as defined in statement 27 for use as an air-freshener.

30. A consumer product as defined in the statement 27 for use as a food additive.

31. A consumer product according to any of one of statements 27 to 30, which is an antiperspirant or deodorant product, further comprising a cosmetically acceptable carrier.

32. Use of a consumer product as defined in statement 27 on the skin.

33. Use of a consumer product as defined in statement 27 as an air-freshener.

34. Use of a consumer product as defined in the statement 27 as a food additive.

35. Use of consumer product according to any of one of statements 27, 28, 31, 32, as an antiperspirant or deodorant product.

36. A method to suppress or attenuate undesirable odour, preferably human axillary malodour, preferably body malodour, more preferably mammalian body malodour, said method comprising the step of applying a malodour counteracting effective amount of a compound of formula (I) or a stereoisomer thereof, to the skin,

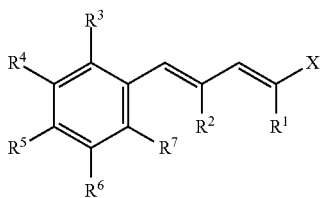

wherein
X is selected from the group consisting of —C(=O)OR$^8$, cyano, —C(=O)—C$_{1-6}$alkyl, —C(=O)—NR$^9$R$^{10}$, hydroxyC$_{1-6}$alkyl, —C(=O)H, and C$_{1-6}$alkoxyC$_{1-6}$alkyl;
R$^1$ is hydrogen or C$_{1-6}$alkyl;
R$^2$ is hydrogen or a group selected from C$_{1-7}$alkyl, and C$_{2-7}$alkenyl, each group being optionally substituted with one or more C$_{3-6}$cycloalkyl;
R$^3$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;
R$^4$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;
R$^5$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;
R$^6$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;
R$^7$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;
R$^8$ is hydrogen or C$_{1-6}$alkyl;
R$^9$ is hydrogen or C$_{1-6}$alkyl; and
R$^{10}$ is hydrogen or C$_{1-6}$alkyl;
with the proviso that the compound of formula (I) is not (2E,4Z)-4-benzylidene-2-methyldec-2-en-1-ol.

37. The method according to statement 36, wherein said compound is a compound as defined in any one of statement 1 to 19.
38. The method according to any one of statements 36 to 37, wherein the undesirable odour is that an activator of receptor OR7D4.
39. The method according to any one of statements 36 to 38, wherein the undesirable odour is that of androstenone (CAS no 18339-16-7).
40. The method according to any one of statements 36 to 38, wherein the undesirable odour is that of androstadienone (CAS no 4075-07-4).
41. A method of counteracting malodour in an air space or a substrate comprising the step of introducing a malodour counteracting effective amount of a compound of formula (I), or a stereoisomer thereof,

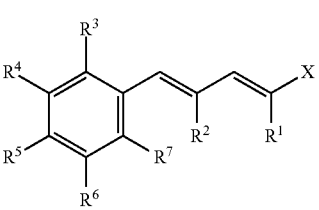

wherein
X is selected from the group consisting of —C(=O)OR$^8$, cyano, —C(=O)—C$_{1-6}$alkyl, —C(=O)—NR$^9$R$^{10}$, hydroxyC$_{1-6}$alkyl, —C(=O)H, and C$_{1-6}$alkoxyC$_{1-6}$alkyl;
R$^1$ is hydrogen or C$_{1-6}$alkyl;
R$^2$ is hydrogen or a group selected from C$_{1-7}$alkyl, and C$_{2-7}$alkenyl, each group being optionally substituted with one or more C$_{3-6}$cycloalkyl;
R$^3$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;
R$^4$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;
R$^5$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;
R$^6$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;
R$^7$ is selected from the group consisting of hydrogen, halo, C$_{1-6}$alkyl, C$_{1-6}$alkoxy, haloC$_{1-6}$alkyl, haloC$_{1-6}$alkoxy, C$_{1-6}$alkoxyC$_{1-6}$alkyl, and cyano;
R$^8$ is hydrogen or C$_{1-6}$alkyl;
R$^9$ is hydrogen or C$_{1-6}$alkyl; and
R$^{10}$ is hydrogen or C$_{1-6}$alkyl.

42. The method according to statement 41, wherein said compound is a compound as defined in any one of statements 1 to 19.
43. The method according to any one of statements 41 to 42, wherein the substrate is a functional product selected from the group consisting of a room freshener spray, a fragrance diffuser, a candle, a sachet, a clothes deodorant, a detergent, a fabric softener, a fabric refresher, a linen spray, a disposable diaper, a diaper pail deodorant, an antiperspirant, a deodorant, a garbage bag, a car freshener, a pet care product and an animal litter material.

A compound of formula (I), or a stereoisomer thereof, is provided herein, wherein
X is selected from the group consisting of —C(=O)OR$^8$, cyano, —C(=O)—C$_{1-6}$alkyl, —C(=O)—NR$^9$R$^{10}$ hydroxyC$_{1-6}$alkyl, —C(=O)H, and C$_{1-6}$alkoxyC$_{1-6}$alkyl;
R$^1$ is hydrogen or C$_{1-6}$alkyl;
R$^2$ is hydrogen or a group selected from C$_{1-7}$alkyl and C$_{2-7}$alkenyl, each group being optionally substituted with one or more C$_{3-6}$cycloalkyl;
R$^3$ is selected from the group consisting of hydrogen, halo, C$_{1-6}$alkyl, C$_{1-6}$alkoxy, C$_{1-6}$alkoxyC$_{1-6}$alkyl, and cyano;
R$^4$ is selected from the group consisting of hydrogen, halo, C$_{1-6}$alkyl, C$_{1-6}$alkoxy, C$_{1-6}$alkoxyC$_{1-6}$alkyl, and cyano;
R$^5$ is selected from the group consisting of hydrogen, halo, C$_{1-6}$alkyl, C$_{1-6}$alkoxy, C$_{1-6}$alkoxyC$_{1-6}$alkyl, and cyano;
R$^6$ is selected from the group consisting of hydrogen, halo, C$_{1-6}$alkyl, C$_{1-6}$alkoxy, C$_{1-6}$alkoxyC$_{1-6}$alkyl, and cyano;
R$^7$ is selected from the group consisting of hydrogen, halo, C$_{1-6}$alkyl, C$_{1-6}$alkoxy, C$_{1-6}$alkoxyC$_{1-6}$alkyl, and cyano;
R$^8$ is hydrogen or C$_{1-6}$alkyl;
R$^9$ is hydrogen or C$_{1-6}$alkyl; and
R$^{10}$ is hydrogen or C$_{1-6}$alkyl;

with the following provisos:

when $R^1=R^2$=hydrogen, then $R^3$ is selected from $C_{3-6}$alkyl, $C_{1-6}$alkoxy, and $C_{1-6}$alkoxy$C_{1-6}$alkyl;

when X is —C(=O)—NR$^9$R$^{10}$ then $R^1$ is —CH$_3$;

when $R^3=R^4=R^5=R^6=R^7$=hydrogen, then $R^2$ is selected from the group consisting of $C_{3-7}$alkyl and $C_{2-7}$alkenyl, each group being optionally substituted by one or more $C_{3-6}$cycloalkyl;

and the compound of formula (I) is none of:
methyl (2E,4E)-4-(4-fluorobenzylidene)-2-nonenoate;
(2E, 4E)-5-p-fluorobenzyl-2-methylpentadienal;
(2E,4E)-5-m-methoxybenzyl-2-methylpentadienoic acid;
(3E,5E)-6-m-methylbenzyl-5-methylhexadienone;
methyl (2E,4E)-4-benzyliden-2-heptenoate; and
(2E,4Z)-4-benzylidene-2-methyldec-2-en-1-ol.

In some preferred embodiments,

X is selected from the group consisting of cyano, —C(=O)O-Me, —C(=O)O-Et, —C(=O)CH$_3$, —C(=O)NH$_2$, —C(=O)NHCH$_3$, —C(=O)N(CH$_3$)$_2$, —CH$_3$OH, —CH(=O), —C(=O)OH, —CH$_2$OMe, and —CH$_2$OEt; preferably X is selected from the group consisting of cyano, —C(=O)O-Me, —C(=O)O-Et, —C(=O)CH$_3$, —C(=O)NH$_2$, —C(=O)NHCH$_3$, —C(=O)N(CH$_3$)$_2$, —CH(=O), —C(=O)OH, —CH$_2$OMe, and —CH$_2$OEt; preferably X is selected from the group consisting of cyano, —C(=O)OMe, —C(=O)OEt, —C(=O)CH$_3$, —CH$_2$OMe, —C(=O)NH$_2$, —C(=O)NHCH$_3$, and —C(=O)N(CH$_3$)$_2$; more preferably X is selected from the group consisting of cyano, —C(=O)OEt and —C(=O)CH$_3$;

$R^1$ is hydrogen or $C_{1-6}$alkyl; preferably, $R^1$ is $C_{1-4}$alkyl or hydrogen; preferably, $R^1$ is $C_{1-2}$alkyl or hydrogen; preferably $R^1$ is —CH$_3$ or hydrogen;

$R^2$ is hydrogen; $C_{1-7}$alkyl optionally substituted by $C_{3-6}$cycloalkyl; or $C_{2-6}$alkenyl; preferably $R^2$ is $C_{5-6}$alkyl, $C_{5-6}$alkenyl, 3-tert-butyl-1-methylpropyl, or $C_1$alkyl substituted with a $C_5$cycloalkyl; more preferably, $R^2$ is $C_6$alkyl, $C_6$alkenyl, 3-tert-butyl-1-methylpropyl, or $C_1$alkyl substituted with a $C_5$cycloalkyl;

$R^3$ is hydrogen, $C_{1-6}$alkyl, $C_{1-6}$alkoxy, cyano, or fluoro; preferably, $R^3$ is hydrogen, $C_{1-6}$alkoxy, or $C_{1-6}$alkyl; more preferably, $R^3$ is hydrogen, OMe, OEt or $C_{4-6}$alkyl;

$R^4$ is hydrogen, $C_{1-6}$alkyl, $C_{1-6}$alkoxy, cyano, or fluoro; preferably, $R^4$ is hydrogen or $C_{1-6}$alkoxy, or $C_{1-6}$alkyl, more preferably, $R^3$ is hydrogen, OMe, OEt, or $C_{1-3}$alkyl;

$R^5$ is hydrogen, fluoro, or cyano. In the preferred compounds of the invention, $R^5$ is hydrogen or fluoro, more preferably, $R^5$ is hydrogen;

$R^6$ is hydrogen; and $R^7$ is hydrogen.

According to some preferred embodiments, the preferred compounds of the invention do not exceed 24 carbon atoms and more particular the preferred compound comprises less than 22 carbon atoms.

In some preferred embodiments,

X is selected from the group consisting of —C(=O)OR$^8$, cyano, —C(=O)—C$_{1-6}$alkyl, —C(=O)—NR$^9$R$^{10}$ hydroxyC$_{1-6}$alkyl, —C(=O)H, and C$_{1-6}$alkoxyC$_{1-6}$alkyl;

$R^1$ is hydrogen or C$_{1-6}$alkyl;

$R^2$ is a group selected from C$_{4-7}$alkyl, C$_{4-7}$alkenyl, or C$_{1-2}$alkyl substituted with one or more C$_{3-6}$cycloalkyl;

$R^3$ is selected from the group consisting of hydrogen, halo, C$_{1-6}$alkyl, C$_{1-6}$alkoxy, C$_{1-6}$alkoxyC$_{1-6}$alkyl, and cyano;

$R^4$ is selected from the group consisting of hydrogen, halo, C$_{1-6}$alkyl, C$_{1-6}$alkoxy, C$_{1-6}$alkoxyC$_{1-6}$alkyl, and cyano;

$R^5$ is selected from the group consisting of hydrogen, halo, C$_{1-6}$alkyl, C$_{1-6}$alkoxy, C$_{1-6}$alkoxyC$_{1-6}$alkyl, and cyano;

$R^6$ is selected from the group consisting of hydrogen, halo, C$_{1-6}$alkyl, C$_{1-6}$alkoxy, C$_{1-6}$alkoxyC$_{1-6}$alkyl, and cyano;

$R^7$ is selected from the group consisting of hydrogen, halo, C$_{1-6}$alkyl, C$_{1-6}$alkoxy, C$_{1-6}$alkoxyC$_{1-6}$alkyl, and cyano;

$R^8$ is hydrogen or C$_{1-6}$alkyl;

$R^9$ is hydrogen or C$_{1-6}$alkyl; and $R^{10}$ is hydrogen or C$_{1-6}$alkyl.

In some preferred embodiments,

X is selected from the group consisting of —C(=O)OR$^8$, cyano, —C(=O)—C$_{1-6}$alkyl (COMe), —C(=O)—NR$^9$R$^{10}$, —C(=O)H, and C$_{1-6}$alkoxyC$_{1-6}$alkyl;

$R^1$ is hydrogen or C$_{1-4}$alkyl, preferably hydrogen or C$_{1-2}$alkyl, preferably hydrogen or methyl;

$R^2$ is a group selected from C$_{1-7}$alkyl, and C$_{2-7}$alkenyl; preferably C$_{2-7}$alkyl, and C$_{3-7}$alkenyl; preferably C$_{3-7}$alkyl, and C$_{4-7}$alkenyl; preferably C$_{4-7}$alkyl, and C$_{4-7}$alkenyl; preferably C$_{5-7}$alkyl, and C$_{5-7}$alkenyl;

$R^3$ is selected from the group consisting of hydrogen, halo, C$_{1-6}$alkyl, C$_{1-6}$alkoxy, and cyano;

$R^4$ is selected from the group consisting of hydrogen, halo, C$_{1-6}$alkyl, C$_{1-6}$alkoxy, and cyano;

$R^5$ is selected from the group consisting of hydrogen, halo (fluoro), C$_{1-6}$alkyl, C$_{1-6}$alkoxy, and cyano;

$R^6$ is selected from the group consisting of hydrogen, halo, C$_{1-6}$alkyl, C$_{1-6}$alkoxy, and cyano;

$R^7$ is selected from the group consisting of hydrogen, halo, C$_{1-6}$alkyl, C$_{1-6}$alkoxy, and cyano;

$R^8$ is hydrogen or C$_{1-6}$alkyl; preferably R$^8$ is C$_{1-6}$alkyl, preferably R$^8$ is C$_{1-4}$alkyl, preferably R$^8$ is C$_{1-2}$alkyl, $R^9$ is hydrogen or C$_{1-6}$alkyl; preferably hydrogen or C$_{1-4}$alkyl; preferably hydrogen or C$_{1-2}$alkyl; preferably hydrogen or methyl; and $R^{10}$ is hydrogen or C$_{1-6}$alkyl; preferably hydrogen or C$_{1-4}$alkyl; preferably hydrogen or C$_{1-2}$alkyl; preferably hydrogen or methyl.

In some preferred embodiments,

X is selected from the group consisting of —C(=O)OR$^8$, cyano, —C(=O)—C$_{1-4}$alkyl (COMe), —C(=O)—NR$^9$R$^{10}$, and —C(=O)H;

$R^1$ is hydrogen or C$_{1-2}$alkyl, preferably hydrogen or methyl;

$R^2$ is a group selected from C$_{1-7}$alkyl, and C$_{2-7}$alkenyl; preferably C$_{2-7}$alkyl, and C$_{3-7}$alkenyl; preferably C$_{3-7}$alkyl, and C$_{4-7}$alkenyl; preferably C$_{4-7}$alkyl, and C$_{4-7}$alkenyl; preferably C$_{5-7}$alkyl, and C$_{5-7}$alkenyl;

$R^3$ is selected from the group consisting of hydrogen, C$_{1-6}$alkyl, and C$_{1-6}$alkoxy;

$R^4$ is selected from the group consisting of hydrogen, halo, and C$_{1-6}$alkyl;

$R^5$ is selected from the group consisting of hydrogen, halo (fluoro), C$_{1-6}$alkyl, C$_{1-6}$alkoxy, and cyano;

$R^6$ is hydrogen;

$R^7$ is selected from the group consisting of hydrogen, halo, C$_{1-6}$alkyl, and cyano;

$R^8$ is C$_{1-6}$alkyl, preferably R$^8$ is C$_{1-4}$alkyl, preferably R$^8$ is C$_{1-2}$alkyl, $R^9$ is hydrogen or C$_{1-4}$alkyl; preferably hydrogen or C$_{1-2}$alkyl; preferably hydrogen or methyl; and $R^{10}$ is hydrogen or C$_{1-4}$alkyl; preferably hydrogen or C$_{1-2}$alkyl; preferably hydrogen or methyl.

In some preferred embodiments,

X is selected from the group consisting of —C(=O)OR$^8$, cyano, —C(=O)—C$_{1-4}$alkyl (COMe), —C(=O)—NR$^9$R$^{10}$, and —C(=O)H;

R$^1$ is hydrogen or C$_{1-2}$alkyl, preferably hydrogen or methyl;

R$^2$ is C$_{3-7}$alkyl, and C$_{4-7}$alkenyl; preferably C$_{4-7}$alkyl, and C$_{4-7}$alkenyl; preferably C$_{5-7}$alkyl, and C$_{5-7}$alkenyl;

R$^3$ is selected from the group consisting of hydrogen, C$_{1-6}$alkyl, and C$_{1-6}$alkoxy;

R$^4$ is selected from the group consisting of hydrogen, halo, and C$_{1-6}$alkyl;

R$^5$ is selected from the group consisting of hydrogen, halo (fluoro), C$_{1-6}$alkyl, C$_{1-6}$alkoxy, and cyano;

R$^6$ is hydrogen;

R$^7$ is selected from the group consisting of hydrogen, halo, C$_{1-6}$alkyl, and cyano;

R$^8$ is C$_{1-4}$alkyl, preferably R$^8$ is C$_{1-2}$alkyl,

R$^9$ is hydrogen or C$_{1-2}$alkyl; preferably hydrogen or methyl; and

R$^{10}$ is hydrogen or C$_{1-2}$alkyl; preferably hydrogen or methyl.

In some preferred embodiments,

X is selected from the group consisting of —C(=O)OR$^8$, cyano, —C(=O)—C$_{1-4}$alkyl (COMe), —C(=O)—NR$^9$R$^{10}$, and —C(=O)H;

R$^1$ is hydrogen or C$_{1-2}$alkyl, preferably hydrogen or methyl;

R$^2$ is C$_{3-7}$alkyl, and C$_{4-7}$alkenyl; preferably C$_{4-7}$alkyl, and C$_{4-7}$alkenyl; preferably C$_{5-7}$alkyl, and C$_{5-7}$alkenyl;

R$^3$ is hydrogen; R$^4$ is hydrogen;

R$^5$ is selected from the group consisting of hydrogen, halo (fluoro), C$_{1-6}$alkyl, C$_{1-6}$alkoxy, and cyano;

R$^6$ is hydrogen; R$^7$ is hydrogen; R$^8$ is C$_{1-2}$alkyl, R$^9$ is hydrogen or methyl; and R$^{10}$ is hydrogen or methyl.

Particularly preferred compounds of the invention are those listed in Table 1 hereafter:

TABLE 1

| Compound | Structure | (M + H)+ |
|---|---|---|
| 1 | | 301.44 |
| 2 | | 247.31 |
| 3 | | 245.33 |
| 4 | 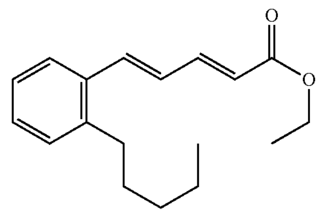 [SMILES: CCCCCc1ccccc1/C=C/C=C/C(=O)OCC] | 273.39 |
| 5 | 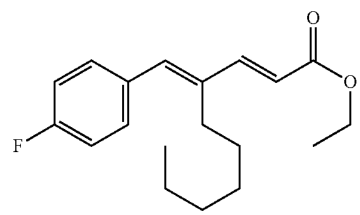 [SMILES: CCCCCCC(/C=C/C(=O)OCC)=C\c1ccc(F)cc1] | 305.41 |
| 6 | 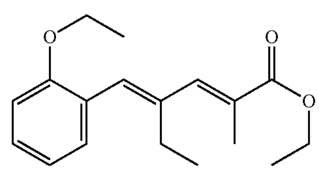 [SMILES: CCOC(=O)/C(C)=C/C(=C/c1ccccc1OCC)CC] | 289.39 |
| 7 | 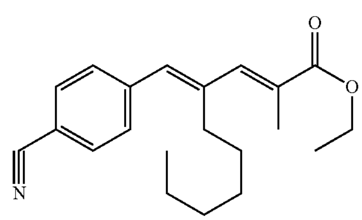 [SMILES: CCCCCCC(=C\c1ccc(C#N)cc1)/C=C(\C)C(=O)OCC] | 326.45 |
| 8 | 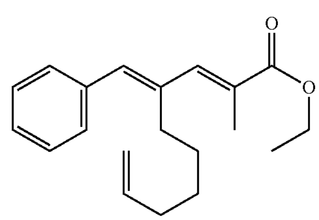 | 299.42 |
| 9 | 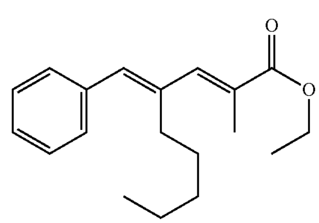 [SMILES: CCCCCC(=C\c1ccccc1)/C=C(\C)C(=O)OCC] | 287.20 |
| 10 | 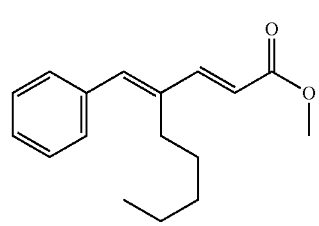 [SMILES: CCCCCC(/C=C/C(=O)OC)=C\c1ccccc1] | 273.18 |

TABLE 1-continued

| Compound | Structure | (M + H)+ |
|---|---|---|
| 11 | 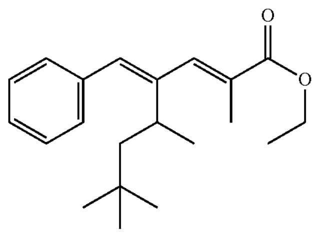 [SMILES: CCOC(=O)/C(C)=C/C(=C/c1ccccc1)C(C)CC(C)(C)C] | 315.46 |
| 12 | 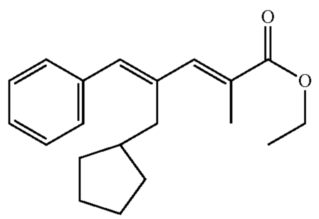 [SMILES: CCOC(=O)/C(C)=C/C(=C/c1ccccc1)CC1CCCC1] | 299.42 |
| 13 | 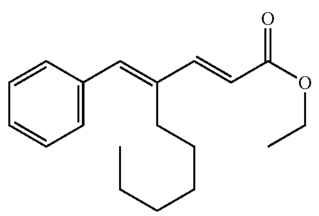 [SMILES: CCCCCCC(/C=C/C(=O)OCC)=C\c1ccccc1] | 287.20 |
| 14 | 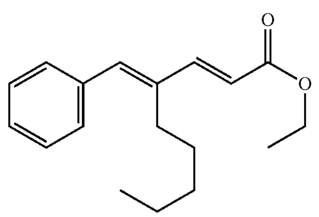 [SMILES: CCCCCC(/C=C/C(=O)OCC)=C\c1ccccc1] | 273.18 |
| 15 | 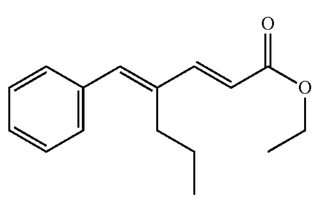 [SMILES: CCCC(/C=C/C(=O)OCC)=C\c1ccccc1] | 245.15 |
| 16 | 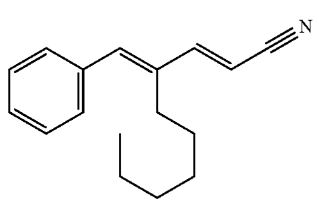 [SMILES: CCCCCCC(/C=C/C#N)=C\c1ccccc1] | 240.36 |
| 17 | 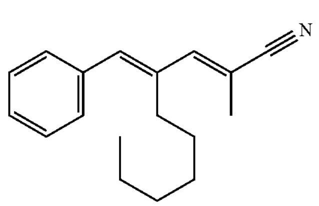 [SMILES: CCCCCCC(/C=C(\C)C#N)=C\c1ccccc1] | 254.19 |
| 18 | | 226.15 |
| 19 | | 298.45 |
| 20 | | 261.33 |
| 21 | | 273.18 |
| 22 | | 259.17 |
| 23 | | 272.40 |
| 24 | | 286.42 |

TABLE 1-continued
| Compound | Structure | (M + H)+ |
|---|---|---|
| 25 |  | 244.35 |
| 26 |  | 258.19 |
| 27 |  | 258.19 |
| 28 |  | 300.45 |
| 29 |  | 271.41 |
| 30 |  | 257.38 |
| 31 |  | 205.27 |
| 32 | 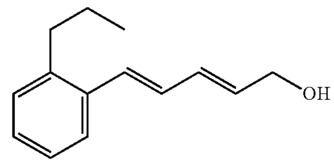 | 203.3 |
| 33 | 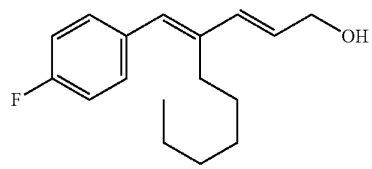 [SMILES: CCCCCCC(/C=C/CO)=C\c1ccc(F)cc1] | 263.37 |
| 34 | 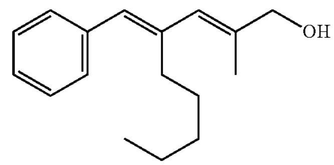 [SMILES: CCCCCC(/C=C(\C)CO)=C\c1ccccc1] | 245.37 |
| 35 | 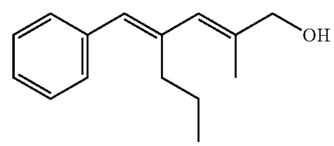 [SMILES: CCCC(/C=C(\C)CO)=C\c1ccccc1] | 217.32 |
| 36 | 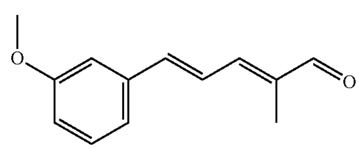 | 203.25 |
| 37 | 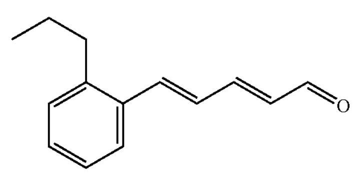 | 201.28 |
| 38 | 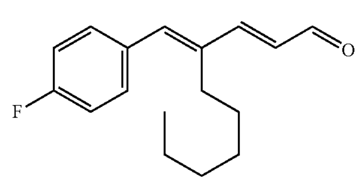 [SMILES: CCCCCCC(/C=C/C=O)=C\c1ccc(F)cc1] | 261.35 |
| 39 | 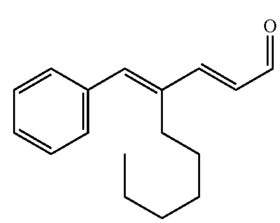 [SMILES: CCCCCCC(/C=C/C=O)=C\c1ccccc1] | 243.35 |

TABLE 1-continued

| Compound | Structure | (M + H)+ |
|---|---|---|
| 40 | 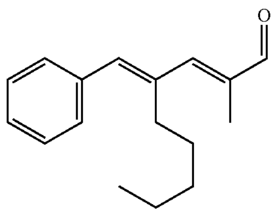 [SMILES: CCCCCC(/C=C(\C)C=O)=C\c1ccccc1] | 243.17 |
| 41 | 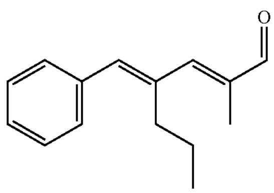 [SMILES: CCCC(/C=C(\C)C=O)=C\c1ccccc1] | 215.14 |
| 42 | 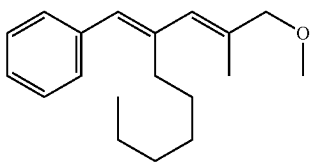 [SMILES: CCCCCCC(/C=C(\C)COC)=C\c1ccccc1] | 273.43 |
| 43 | 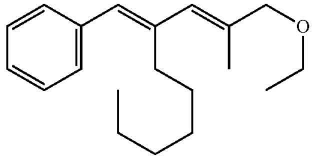 [SMILES: CCCCCCC(/C=C(\C)COCC)=C\c1ccccc1] | 287.46 |
| 44 | 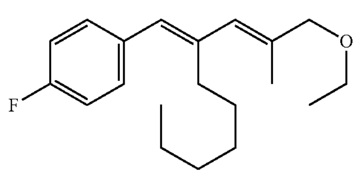 [SMILES: CCCCCCC(/C=C(\C)COCC)=C\c1ccc(F)cc1] | 305.45 |
| 45 | 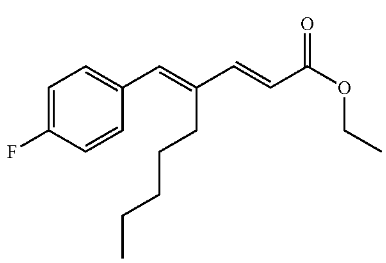 [SMILES: CCCCCC(/C=C/C(=O)OCC)=C\c1ccc(F)cc1] | 291.2 |

The compounds of the invention can be prepared by different ways with reactions known by the person skilled in the art. Reaction schemes as described in the examples section illustrate by way of example different possible approaches.

The invention also provides a compound of formula (I), as well as any one of the compounds of Table 1, or methyl (2E,4E)-4-(4-fluorobenzylidene)-2-nonenoate for use as antagonists of OR7D4, preferably wherein said use is non-therapeutic. According to one embodiment, this use as antagonist of OR7D4 results in a sensory effect which significantly reduces or eliminates the olfactory perception of androstenone or any other OR7D4 activator.

The invention also encompasses processes for the preparation of compounds of the invention.

In one embodiment, the invention further encompasses a process for the preparation of a compound of formula (I)

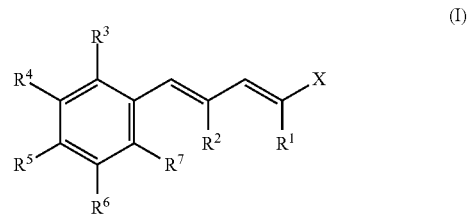

wherein $R^1$, $R^2$, $R^3$, $R^4$, $R^5$, $R^6$, $R^7$, and X are as defined above in respect to formula (I), which comprises, as shown in scheme 1, at least two steps procedure which starts by coupling a compound of a formula A with a compound of formula B, for example according to a transformation known to the person skilled in the art as the Knoevenagel condensation, the so produced intermediate C is then engaged in a second step, which can be for example either a Wittig reaction (using the adapted phosphorane derivatives D) or a Wittig-Horner reaction (sometimes called Horner-Wadsworth-Emmons Reaction as well, using the adapted phosphonate derivative F) to afford compound of formula (I), Scheme 1

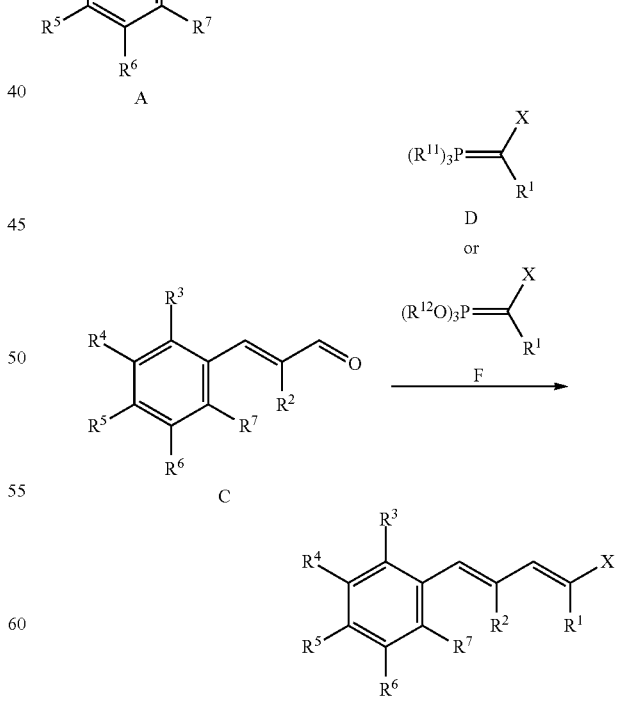

wherein $R^1$, $R^2$, $R^3$, $R^4$, $R^5$, $R^6$, $R^7$, and X are as defined above in respect to formula (I), and $R^{11}$ is $C_{6-12}$aryl or $C_{1-12}$alkyl, preferably $R^{11}$ is phenyl or $C_{1-5}$alkyl; and $R^{12}$ is $C_{1-12}$alkyl; preferably $C_{1-5}$alkyl.

Uses

The compounds hereinabove described, when applied to the human skin and in particular the skin of the axilla, may be used to prevent, suppress or attenuate undesirable odours, preferably body malodour, more preferably mammalian body malodour, more particularly human axillary malodour, still more particular the odour associated with androstenone released in sweat.

In a second aspect of the of invention, the compounds of formula (I) hereinabove described may be employed in consumer products such as cosmetic products primarily for use on human skin, such as under-arm deodorants, antiperspirants or any other products for use on the skin. Consumer products may also include lotions, powders, ointments, body-wipes, colognes, shaving creams and the like.

Additionally, however, the compounds referred to herein can be incorporated into all manner of consumer products that are designed to freshen, reduce, suppress or eliminate malodour on inanimate surfaces, especially fabrics, but particularly clothing or any other articles that may come into contact with, or are applied to, the body. Particularly, said consumer products are designed, in whole or in part, to reduce malodour on said inanimate surfaces that may be contaminated with sweat.

The consumer products into which the compounds may be incorporated include any such products for the treatment of fabric, for purposes such as (but not limited to) cleaning, softening, refreshening, rendering antistatic, rendering easier to iron or otherwise process. Typical non-limiting examples of such consumer products include fabric refreshers (such as spray-on compositions and pre-spotters), regular and concentrated fabric softeners and conditioners in liquid, solid or aerosol form, tumble dryer sheets, solids and liquid soaps and detergent bars, NSD Bars, liquid and powder detergents, liquid and solid bleaches, and adjuvant compositions. The compounds hereinabove defined may be incorporated into consumer products that are applied to or otherwise brought into contact with, a fabric, for example, by coating, immersing or spraying.

The compounds may also be employed in air freshener applications.

Malodour counteracting effective amount is understood to mean the amount of the inventive malodour counteractant compound employed in a functional product that is organoleptically effective to abate a given malodour while reducing the combined intensity of the odour level, wherein the given malodour is present in air space or has deposited on a substrate.

Typically, compounds hereinabove defined may be employed in consumer products in varying amounts that will depend on the nature of the consumer product and the particular end use application. Typically, however, one might expect to employ the compound in amounts ranging from 0.001% to 1%, preferably 0.005% to 0.5%, more preferably 0.01% to 0.2% by weight of the total consumer product composition.

In the preparation of a consumer product according to the present invention, the compounds hereinabove defined may be combined with other ingredients typically employed in consumer products. For example, in a deodorant or antiperspirant for use on the human or animal body, or for use on articles that might come into contact with human or animal skin, an additional malodour-counteracting active agent may be desirable. This might be a perfume, an antiperspirant active, or an anti-microbial active.

Typical antiperspirant actives include astringent active salts, in particular, aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates. Levels of incorporation may typically be from 5%-20% by weight of the composition of which they form a part.

Typical anti-microbial actives include quaternary ammonium compounds (like cetyltrimethylammonium salts), chlorhexidine and salts thereof; diglycerol monocaprate, diglycerol monolaurate, glycerol monolaurate, polyhexamethylene biguanide salts (also known as polyaminopropyl biguanide salts-, an example being Cosmocil CQ available from Arch chemicals), 2,4,4'-trichloro-2'-hydroxy-diphenyl ether (triclosan), and 3,7,11-trimethyldodeca-2,6,10-trienol (farnesol). Levels of incorporation may be from 0.01% to 1% by weight of the composition.

In addition, a consumer product may contain one or more excipients or adjuvants, which are typically included in such products in order to aid in their manufacture, storage, application or performance.

In particular, a consumer product may contain a carrier material that may be hydrophobic or hydrophilic, solid or liquid depending on the nature of the product and the use for which it is intended.

Hydrophobic carrier materials include silicones, that is, polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, or additionally, non-silicone hydrophobic materials may be used. Such materials include mineral oils, hydrogenated polyisobutene, polydecene, paraffins, isoparaffins of at least 10 carbon atoms, aliphatic or aromatic ester oils (e.g. isopropyl myristate, lauryl myristate, isopropyl palmitate, diisopropyl sebecate, diisopropyl adipate, or $C_8$ to $C_{18}$ alkyl benzoates), and polyglycol ethers, for example polyglycol butanol ethers.

Hydrophilic carrier materials, for example water, may also be employed. Water can be distilled, deionized, or tap water. Water, containing a small amount of low molecular weight monohydric alcohols, e.g., ethanol, methanol, and isopropanol, or polyols, such as ethylene glycol and propylene glycol, can also be useful.

Organic solvents might also be employed. They include organic solvents that are aliphatic alcohols, for example monohydric or polyhydric alcohols having 2 to 8 carbon atoms, and polyglycol ethers, such as oligoglycol ethers having 2 to 5 repeat units. Examples include dipropylene glycol, glycerol, propylene glycol, butylene glycol, ethanol, propanol, isopropanol, and industrial methylated spirits.

Mixtures of carrier materials may also be used. The amount of carrier material employed is dependent on the nature of the product and can range from 1-99%, more typically 10-95%, by weight of a consumer product composition.

Structurants and emulsifiers may also be employed in consumer product compositions of the invention. They may be present at levels from 0.01-50%, more typically 0.1-10% by weight of the composition.

Suitable structurants include cellulosic thickeners such as hydroxy propyl cellulose and hydroxy ethyl cellulose, and dibenzylidene sorbitol. Other suitable structurants include sodium stearate, stearyl alcohol, cetyl alcohol, hydrogenated castor oil, synthetic waxes, paraffin waxes, hydroxystearic acid, dibutyl lauroyl glutamide, alkyl silicone waxes, quaternium-18 bentonite, quaternium-18 hectorite, silica, and propylene carbonate. Suitable emulsifiers include steareth-2, steareth-20, steareth-21, ceteareth-20, glyceryl stearate, cetyl alcohol, cetearyl alcohol, PEG-stearate, dimethicone copolyol, and poloxamines.

Further emulsifiers/surfactants are perfume solubilisers and wash-off agents. Examples of the former include PEG-hydrogenated castor oil, available from BASF in the Cremaphor RH and CO ranges. Examples of the latter include poly(oxyethylene) ethers. Certain sensory modifiers are further desirable components in the compositions of the invention. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, talc, finely-divided silica (e.g. Aerosil 200), polyethylene (eg. Acumist B18), polysaccharides, corn starch, $C_{12-15}$ alcohol benzoate, PPG-3 myristyl ether, octyl dodecanol, $C_{7-14}$ isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

Consumer products according to the invention may contain solubilising aids for one or more other ingredients contained in said product, including compounds according to formula (I) if needed. A suitable solubilising aid is surfactant, preferably no-foaming or low-foaming surfactant. Suitable surfactants are nonionic surfactants, anionic surfactants, cationic surfactants, amphoteric surfactants, zwitterionic surfactants, and mixtures thereof, preferably nonionic surfactants and cationic surfactants, and mixtures thereof. Suitable solvents and diluents may be selected from compounds well known to the fragrance art for such purposes, typical non-limiting examples including propylene glycol, dipropylene glycol, isopropyl myristate, and the like.

Consumer products according to the invention may contain preservatives, pH control agents (such as buffers), chelating agents, defoaming agents, antifoaming agents, antistatic agents, colorants, antioxidants, aesthetic agents such as opacifiers, perlizers, dyes and mixtures thereof.

If the consumer product composition is in the form of an aerosol composition, a volatile propellant is typically employed. The level of incorporation of the volatile propellant is typically from 40-99% parts by weight.

Non-chlorinated volatile propellant are preferred, in particular liquefied hydrocarbons or halogenated hydrocarbon gases (particularly fluorinated hydrocarbons such as 1,1-difluoroethane and/or 1-trifluoro-2-fluoroethane) that have a boiling point of below 10 degrees Centigrade and especially those with a boiling point below zero degrees Centigrade. It is especially preferred to employ liquefied hydrocarbon gases, and especially $C_{3-6}$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane.

Other propellants that can be contemplated include alkyl ethers, such as dimethyl ether or compressed non-reactive gasses such air, nitrogen or carbon dioxide.

Fragrance is also a desirable additional component in a consumer product of the invention. Suitable materials include conventional perfumes, such as perfume oils and also include so-called deo-perfumes, as described in EP 545,556 and other publications. These latter materials may also qualify as additional organic anti-microbial agents. Levels of incorporation are preferably up to 20%, more typically up to 2% by weight. The fragrance ingredients may be selected for their odour characteristics, which are preferred in order to provide a fresh impression on the substrate to which the composition is directed.

Fragrance ingredients may be selected from the group consisting of aromatic and aliphatic esters having molecular weights from about 130 to about 250; aliphatic and aromatic alcohols having molecular weights from about 90 to about 240; aliphatic ketones having molecular weights from about 150 to about 260; aromatic ketones having molecular weights from about 150 to about 270; aromatic and aliphatic lactones having molecular weights from about 130 to about 290; aliphatic aldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320; and essentially free from nitromusks and halogenated fragrance materials.

Representative fragrance ingredients include: adoxal aliphatic aldehyde 2,6,10-trimethyl-9-undecen-1-al, allyl amyl glycolate, allyl amyl glycolate, allyl cyclohexane propionate, allyl-3-cyclohexyl propionate, amyl acetate, 3-methyl-1-butanol acetate, amyl salicylate, amyl salicylate, anisic aldehyde, 4-methoxy benzaldehyde, aurantiol, bacdanol, 2-ethyl-4-(2,2,3-trimethyl-3-cyclopenten-1-yl)-2-buten-1-ol, benzaldehyde, benzophenone, benzophenone, benzyl acetate, benzyl acetate, benzyl salicylate, benzyl salicylate, beta damascene, 1-(2,6,6-trimethyl-1-cyclohexen-1-yl)-2-buten-1-one, beta gamma hexanol, 3-hexen-1-ol, buccoxime, 1,5-dimethyl-oxime bicyclo[3,2,1]octan-8-one, cedrol, octahydro-3,6,8,8-tetramethyl-1H-3A,7-methanoazulen-6-ol, cetalox, dodecahydro-3A,6,6,9A-tetramethylnaphtho[2,1B]-furan, cis-3-hexenyl acetate, cis-3-hexenyl acetate, cis-3-hexenyl salicylate, beta, gamma-hexenyl salicylate, citronellol, 3,7-dimethyl-6-octenol, citronellyl nitrile, geranyl nitrile, clove stem oil, coumarin, cyclohexyl salicylate, cyclohexyl salicylate, cymal, 2-methyl-3-(para iso propylphenyl)propionaldehyde, decyl aldehyde, decyl aldehyde, delta damascene, 1-(2,6,6-trimethyl-3-cyclo-hexen-1-yl)-2-buten-1-one, dihydromyrcenol, 3-methylene-7-methyl octan-7-ol, dimethyl benzyl carbinyl ester, dimethyl benzyl carbinyl acetate, ethyl vanillin, ethyl-2-methyl butyrate, ethyl-2-methyl butyrate, ethylene brassylate, ethylene tridecan-1,13-dioate, eucalyptol, 1,8-epoxy-para-menthane, eugenol alcohol 4-allyl-2-methoxy phenol, exaltolide, cyclopentadecanolide, flor acetate, dihydro-nordicyclopentadienyl acetate, florhydral, 3-(3-isopropylphenyl) butanal, frutene, dihydro-nordicyclopentadienyl propionate, galaxolide, 1,3,4,6,7,8-hexahydro-4,6,6,7,8,8-hexamethylcyclopenta-gamma-2-benzopyrane, gamma decalactone, 4-N-hepty-4-hydroxybutanoic acid, gamma dodecalactone, 4-N-octyl-4-hydroxy-butanoic acid, geraniol, 3,7-dimethyl-2,6-octadien-1-ol, geranyl acetate, 3,7-dimethyl-2,6-octadien-1-yl acetate, geranyl nitrile, 3,7-dimethyl-2,6-octadienenitrile, helional, alpha-methyl-3,4, (methylenedioxy) hydrocinnamaldehyde, heliotropin, heliotropin hexyl acetate, hexyl acetate, hexyl cinnamic aldehyde, alpha-n-hexyl cinnamic aldehyde, hexyl salicylate, hexyl salicylate, hydroxyambran, 2-cyclododecyl-propanol, hydroxycitronellal, hydroxycitronellal, ionone alpha, 4-(2,6,6-trimethyl-1-cyclohexenyl-1-yl)-3-buten-2-one, ionone beta aliphatic ketone 4-(2,6,6-trimethyl-1-cyclohexen-1-yl)-3-butene-2-one, ionone gamma methyl 4-(2,6,6-trimethyl-2-cyclohexyl-1-yl)-3-methyl-3-buten-2-one, iso E super 7-acetyl-1,2,3,4,5,6,7,8-octahydro-1,1,6,7,tetramethyl naphthalene, iso eugenol ether 2-methoxy-4-(1-propenyl) phenol, iso jasmone aliphatic ketone 2-methyl-3-(2-pentenyl)-2-cyclopenten-1-one, koavone, acetyl di-isoamylene, lauric aldehyde, lavandin natural, lavender natural, lemon CP, d-limonene, d-limonene/orange terpenes alkene 1-methyl-4-iso-propenyl-1-cyclohexene, linalool, 3-hydroxy-3,7-dimethyl-1,6-octadiene, linalyl acetate ester 3-hydroxy-3,7-dimethyl-1,6 octadiene acetate, 2,4-dihydroxy-3,6-dimethyl benzoic acid methyl ester, lyral, 4-(4-hydroxy-4-methyl-pentyl) 3-cyclohexene-1-carboxaldehyde, majantol, 2,2-dimethyl-3-(3-methylphenyl)-propanol, mayol, 4-(1-methylethyl) cyclohexane methanol, methyl anthranilate, methyl-2-aminobenzoate, methyl beta naphthyl ketone, methyl beta naphthyl ketone, methyl cedrylone, methyl cedrenyl ketone, methyl chavicol, 1-methyloxy-4,2-propen-1-yl benzene, methyl dihydrojasmonate, methyl dihydrojasmonate, methyl nonyl acetaldehyde, methyl nonyl acetaldehyde, musk indanone, 4-acetyl-6-tert butyl-1,1-dimethyl indane, nerol, 2-cis-3,7-dimethyl-2,6-octadien-1-ol, nonalactone, 4-hydroxynonanoic acid, norlimbanol, 1-(2,2,6-trimethyl-cyclohexyl)-3-hexanol, orange CP, P. T. bucinal, 2-methyl-3(para tert butylphenyl)propionaldehyde, para hydroxy phenyl butanone, para hydroxy phenyl butanone patchouli, phenyl acetaldehyde, 1-oxo-2-phenylethane phenyl acetaldehyde dimethyl, phenyl acetaldehyde dimethyl acetal phenyl ethyl acetate, phenyl ethyl acetate phenyl ethyl alcohol, phenyl ethyl alcohol, phenyl ethyl phenyl acetate, 2-phenylethyl phenyl acetate, phenyl hexanol/phenoxanol, 3-methyl-5-phenylpentanol, polysantol, 3,3-dimethyl-5-(2,2,3-trimethyl-3-cyclopenten-1-yl)-4-penten-2-ol, prenyl acetate, 2-methylbuten-2-ol-4-acetate, rosaphen, 2-methyl-5-phenyl pentanol, sandalwood, alpha-terpinene aliphatic alkane 1-methyl-4-iso-propylcyclohexadiene-1,3-terpineol (alpha terpineol and alcohol para-menth-1-en-8-ol, para-beta terpineol) menth-1-en-1-ol, terpinyl acetate ester para-menth-1-en-8-yl acetate, tetra hydro linalool, 3,7-dimethyl-3-octanol, tetrahydromyrcenol, 2,6-dimethyl-2-octanol, tonalid, 7-acetyl-1,1,3,4,4,6-hexamethyl, tetralin, undecalactone lactone 4-N-heptyl-4-hydroxybutanoic acid, undecavertol, 4-methyl-3-decen-5-ol, undecyl aldehyde, undecanal, undecylenic aldehyde, undecylenic aldehyde, vanillin aromatic aldehyde 4-hydroxy-3-methoxybenzaldehyde, verdox, 2-tert-butyl cyclohexyl acetate, vertenex, 4-tert-butyl cyclohexyl acetate and mixtures thereof.

Preferably consumer products contain an effective amount of perfume to provide the freshening fragrance to surfaces when first applied and some lingering fragrance in-wear.

The compounds of the present invention may be in the form of liquids or solids and they may be simply admixed into consumer product bases in these neat forms. Alternatively, it may be desirable to solubilise a solid compound in a suitable solvent before mixing into a consumer product base.

Still further, it may be desired to spray dry a liquid compound onto a solid support to form a powder, which can then be admixed with a consumer product base.

Still further, it may be desirable to present the compounds in a delivery vehicle. For example, it may be desirable to present the compounds on or in a solid support. Said vehicles may be in the form of a core-shell capsule, wherein the compound is contained in a core and surrounded by a shell. Alternatively, it may be desired to absorb the compound into a porous body such as a porous bead or the like. Further still, in may be desirable to dissolve or disperse a compound in a matrix material.

Such vehicles may be employed as a means of affecting the rate of release of the compound into the vapour phase, or it may act as a means by which the compound can be incorporated into a consumer product base. Still further, it may be a means of stabilising a compound against an aggressive external environment.

Capsule shells may be formed from any of those materials conventionally known in the art and may include a naturally-derived material, such as gelatine or waxes; or a synthetic polymer, such as an aminoplast resin, an acrylic resin or a polyurea. Synthetic materials may include water-insoluble or water-soluble encapsulating materials such as polyethylenes, polyamides, polystyrenes, polyisoprenes, polycarbonates, polyesters, polyacrylates, vinyl polymers and polyurethanes and mixtures thereof.

Capsules may consist of a matrix of polysaccharide and polyhydroxy compounds, water-soluble or water-dispersible encapsulating materials comprising dextrins derived from ungelatinised starch acid-esters of substituted dicarboxylic acids; useful starches including, raw starch, pregelatinised starch, modified starch derived from tubers, legumes, cereal and grains, for example corn starch, wheat starch, rice starch, waxy corn starch, oat starch, cassava starch, waxy barley, waxy rice starch, sweet rice starch, amioca, potato starch, tapioca starch, oat starch, cassava starch, and mixtures thereof; modified starches including hydrolysed starch, acid thinned starch, starch esters of long chain hydrocarbons, starch acetates, starch octenyl succinate, and mixtures thereof.

The term "hydrolysed starch" refers to oligosaccharide-type materials that are typically obtained by acid and/or enzymatic hydrolysis of starches, preferably corn starch. Suitable hydrolysed starches for inclusion in the present invention include maltodextrins and corn syrup solids. The hydrolysed starches for inclusion with the mixture of starch esters have a Dextrose Equivalent (DE) values of from about 10 to about 36 DE. The DE value is a measure of the reducing equivalence of the hydrolysed starch referenced to dextrose and expressed as a percent (on a dry basis). The higher the DE value, the more reducing sugars present. A method for determining DE values can be found in Standard Analytical Methods of the Member Companies of Corn Industries Research Foundation, 6th ed. Corn Refineries Association, Inc. Washington, D.C. 1980, D-52.

Starch esters having a degree of substitution in the range of from about 0.01% to about 10.0% may be used to encapsulate the perfume oils of the present invention.

Modified starches having emulsifying and emulsion stabilizing capacity such as starch octenyl succinates have the ability to entrap the perfume oil droplets in the emulsion due to the hydrophobic character of the starch modifying agent. Preferably, the encapsulating material is water-soluble modified starch solid matrix, preferably a starch raw material that has been modified by treating said starch raw material with octenyl-succinic acid anhydride. More preferably the said modified starch is mixed with a polyhydroxy compound before treatment with octenyl-succinic acid anhydride.

A particular example of a modified starch is a waxy, maize starch, pregelatinised, dextrinised is mixed with sorbitol or any other alcohol type and then treated with octenyl succinic anhydride.

The use of such starches is described in European Patent 0 965 326, the contents of which are included herein by reference.

The compounds may be added to consumer product bases as such, or they may be added to the bases as part of a mixture of ingredients. For example, the compounds of the present invention may be mixed with fragrance ingredients to form a fragrance composition, which can then be added to a consumer product base.

Compounds of the present invention may have an odour, or they may be odourless. It is preferred, however, that they are odourless. In this way, they can be added to a perfume composition without influencing or affecting the particular hedonic effect that a perfumer is attempting to create.

When presented in a consumer product a compound of the present invention should exhibit a sufficient vapour pressure in order that it can reach the nasal epithelium and thereby interact with the olfactory receptor in the desired manner.

The olfactory receptor OR7D4 referred to hereinabove is a member of the family of G-protein coupled receptors (GPCRs). Expressed in cell membranes, the GPCR olfactory receptors are responsible for the detection of odorant molecules. Activated receptors are the initial players in a signal transduction cascade, which ultimately produces a nerve impulse, which is transmitted to the brain. Once the odorant has bound to the olfactory receptor, the receptor undergoes structural changes and it activates the G-protein. This in turn leads to a cascade of cellular events that transmits information to the brain. OR7D4 is an olfactory receptor that is narrowly tuned and responds only to androstenone and androstadienone (Keller et al 2007). This finding enables the OR7D4 receptor to be used in screening methods to identify compounds that antagonize its response to androstenone.

The present invention also encompasses the use of a compound according to the invention as agonist of OR7D4, preferably wherein said use is non-therapeutic.

These antagonist compounds may then be used in the consumer product applications in which it is desirable to reduce or to block the olfactory perception of androstenone.

Accordingly, the invention provides in another of its aspects a method of identifying agents (or a method of aiding in the selection of agents or a method of screening for said agents), which inhibit the binding of androstenone to OR7D4, the olfactory receptors whose activity is modulated by androstenone.

In a particular embodiment of the invention there is provided a method of identifying compounds (or a method of aiding in the selection of compounds or a method of screening for said compounds), which inhibit the binding of androstenone to the OR7D4 olfactory receptor.

In another aspect of the invention, in said method, a library comprising compounds as hereinabove defined is screened in an assay for detecting inhibition of binding between androstenone and olfactory receptors whose activity is modulated by androstenone, more particularly the OR7D4 olfactory receptor.

In a particular embodiment of the present invention there is provided a method for identifying compounds that antagonise the response of OR7D4 to androstenone comprising the steps of:

contacting at least one cell, or membrane thereof, expressing the nucleic acid sequence encoding OR7D4 or a functional equivalent thereof, with androstenone and at least one test compound according to formula (I) defined hereinabove, and measuring the effect of at least one test compound(s) on the response of OR7D4 to androstenone.

In an embodiment of the invention said method is an in vitro method.

Functional equivalents of the nucleotide sequence encoding OR7D4 include those nucleotide sequences that by virtue of the degeneracy of the genetic code possess a different nucleotide sequence to the OR7D4 nucleotide sequence, corresponding to GenBank accession number KP290356.1, but that encode for the same amino acid sequence, corresponding to GenBank accession number ALI87532, with the same activity. Functional equivalents encompass naturally occurring variants of the sequences described herein as well as synthetic nucleotide sequences. For example those nucleotide sequences that are obtained by chemical synthesis or recombination of naturally existing DNA. Functional equivalents may be the result of, natural or synthetic, substitutions, additions, deletions, replacements, or insertions of one or more nucleotides. Examples of functional equivalents include those nucleic acid sequences comprising a sense mutation resulting from the substitution of at least one conserved amino acid which does not lead to an alteration in the activity of the polypeptide and thus they can be considered functionally neutral. Other non-limiting examples of functional equivalents include fragments, orthologues, splice variants, single nucleotide polymorphisms, and allelic variants. Such functional equivalents may have 75%, 80%, or 90% homology to the nucleotide sequences of OR7D4.

Nucleotide sequence homology may be determined by sequence identity or by hybridisation. Sequence identity may be determined using basic local alignment search tool technology (hereinafter BLAST). BLAST technology is a heuristic search algorithm employed by the programs blastn which is publically available. If homology is determined by hybridisation, the nucleotide sequences should be considered substantially homologous provided that they are capable of selectively hybridizing to the OR7D4 nucleotide sequence disclosed herein. Hybridisation may be carried out under stringent hybridisation conditions at a temperature of 42° C. in a solution consisting of 50% formamide, 5× standard sodium citrate (hereinafter SSC), and 1% sodium dodecyl sulphate (hereinafter SDS). Washing may be carried out at 65° C. in a solution of 0.2×SSC and 0.1% SDS.

Background hybridization may occur because of other nucleotide sequences present, for example, in the cDNA or genomic DNA library being screened. Any signal that is less than 10 fold as intense as the specific interaction observed with the target DNA may be considered background. The intensity of interaction may be measured, for example, by radiolabelling the probe.

Suitable cells for use in the methods disclosed herein include prokaryote and eukaryotic cells, non-limiting examples of which include, bacteria cells, mammalian cells, yeast cells, or insect cells (including Sf9), amphibian cells (including melanophore cells), or worm cells including cells of *Caenorhabditis* (including *Caenorhabditis elegans*). Non limiting examples of suitable mammalian cells include, COS cells (including Cos-1 and Cos-7), CHO cells, HeLa cells, HEK293 cells, HEK293T cells, HEK293 T-Rex™ cells, or other transfectable eukaryotic cell lines and the like.

For use in the aforementioned method cells may be isolated cells or alternatively they may be components of tissue including, but not limited to, mammalian tissue and transgenic animal tissue.

The cells used in the method may naturally express a nucleotide sequence encoding OR7D4, or a functional equivalent thereof, or they may be recombinant cells expressing a nucleotide sequence encoding OR7D4, or a functional equivalent thereof.

Recombinant cells may be transfected with a nucleotide sequence or an amino acid sequence encoding OR7D4, or a functional equivalent thereof, transiently or stably, as is well known in the art.

Isolation and expression of OR7D4, or functional equivalents thereof, may be effected by well-established cloning techniques using probes or primers constructed based on the nucleic acid sequence disclosed herein. Once isolated, the nucleotide sequences may be amplified through the polymer chain reaction (hereinafter PCR).

Any known method for introducing nucleotide sequences into host cells may be used. It is only necessary that the particular genetic engineering procedure used be capable of successfully introducing the relevant genes into the host cell capable of expressing the proteins of interest.

These methods may involve introducing cloned genomic DNA, cDNA, synthetic DNA or other foreign genetic material into a host cell and include the use of calcium phosphate transfection, polybrene, protoplast fusion, electroporation, liposomes, microinjection, expression vectors, and the like.

According to other embodiments expression vectors may be used to infect or transfect host cells with the nucleic acid sequence encoding OR7D4, or a functional equivalent thereof, for use in the aforementioned method.

Expression vectors, both as individual expression vectors or as libraries of expression vectors, comprising at least one nucleic acid sequences encoding OR7D4 and/or functional equivalents thereof, may be introduced and expressed in a cell's genome, cytoplasm, or nucleus by a variety of conventional techniques. It is well within the purview of the person skilled in the art to decide upon a suitable technique.

Any suitable expression vector may be used. Non limiting examples of types of vectors include bacteriophage, plasmid, or cosmid DNA expression vectors, yeast expression vectors; viral expression vectors (for example baculovirus), or bacterial expression vectors.

After transfection, the transfected cells may be cultured using standard culturing conditions well known in the art. It will be apparent to the skilled person that different cells require different culture conditions including appropriate temperature and cell culture media. It is well within the purview of the person skilled in the art to decide upon culture conditions depending on the cells in question and the desired end result. Information on appropriate culturing media and conditions with respect to certain cells may be found on the American type culture collection (ATCC) Website.

The effect of a test compound on the response of OR7D4 may be determined by comparing the response of OR7D4 to androstenone in both the absence and presence of a test compound.

A method for identifying compounds that antagonize the response of OR7D4 to androstenone may comprise:
  I. contacting at least one cell, or membrane thereof, expressing the nucleic acid sequence encoding OR7D4 or a functional equivalent thereof, with androstenone or any other activator agonist of the receptor;
  II. measuring the response of OR7D4 to androstenone or any other activator agonist of the receptor;
  III. contacting at least one cell, or membrane thereof, with at least one test compound, and androstenone or any other activator agonist of OR7D4;
  IV. measuring the response of OR7D4 to androstenone or any other activator agonist of the receptor in the presence of the test compound;
  V. calculating the change in the response of OR7D4 to androstenone or any other activator of the receptor.

The response of OR7D4 may be determined by measuring the change in any parameter that is directly or indirectly under the influence of OR7D4. These parameters include physical, functional, and chemical effects. Examples of measurable parameters include, but are not limited to, changes in ion flux, membrane potential, current flow, transcription, G-protein binding, GPCR phosphorylation or dephosphorylation, signal transduction, receptor-ligand interactions, intracellular messenger concentrations e.g. phospholipase C, adenylate cyclase, guanylate cyclase, phospholipase, cAMP, cGMP, IP3, DAG, intracellular $Ca^{2+}$ ligand binding, neurotransmitter levels, GTP-binding, GTPase, adenylate cyclase, phospholipid-breakdown, diacylglycerol, inositol triphosphate, arachidonic acid release, protein kinase c (PKC), MAP kinase tyrosine kinase, and ERK kinase.

The aforementioned parameters may be measured by any means known to those skilled in the art, for example, changes in the spectroscopic characteristics (e.g. fluorescence, absorbance, refractive index), hydrodynamic (e.g. shape), chromatographic, or solubility properties, patch clamping, voltage-sensitive dyes, whole cell currents, radio-isotope efflux, inducible markers, oocyte OR7D4 gene expression, tissue culture OR7D4 cell expression, transcriptional activation of OR7D4 genes, ligand binding assays, voltage, membrane potential and conduction changes; ion flux assays, assays that measure changes in parameters of the transduction pathways such as intracellular $IP_3$ and $Ca^{2+}$, diacylglycerol/DAG, arachinoid acid, MAP kinase or tyrosine kinase, assays based on GTP-binding, GTPase, adenylate cyclase, phospholipid-breakdown, diacylglycerol, inositol triphosphate, arachidonic acid release, PKC, kinase and transcriptional reporters, or by other G-protein specific assays such as labelling with GTPγS.

To enable the measurement of certain parameters it may be desirable to link a G-protein or a reporter gene to OR7D4. Any suitable G-protein or reporter gene may be used and it is well within the purview of the person skilled in the art to decide upon an appropriate G-protein or reporter gene depending on the desired response. Examples of reporter genes include, but are not limited to luciferase, CAT, GFP, β-lactamase, β-galactosidase, and the so-called "immediate early" genes, c-fos proto-oncogene, transcription factor CREB, vasoactive intestinal peptide (VIP) gene, the somatostatin gene, the proenkephalin gene, the phosphoenolpyruvate carboxy-kinase (PEPCK) gene, genes responsive to NF-κB, and AP-1-responsive genes (including the genes for Fos and Jun, Fos-related antigens (Fra) 1 and 2, IκBα, ornithine decarboxylase, and annexins I and II).

In general reporter genes are linked to one or more transcriptional control elements or sequences necessary for receptor-mediated regulation of gene expression, including but not limited to, one or more promoter, enhancer and transcription-factor binding site necessary for receptor-regulated expression.

The assay methods described herein may be used to screen libraries of compounds for antagonists.

Accordingly, the invention provides in another of its aspects a library of compounds, comprising compounds of formula (I) as defined hereinabove.

In yet another aspect of the invention there is provided the use of a compound of the formula (I) as hereinabove defined in an in-vitro assay for detecting inhibition of binding between androstenone and olfactory receptors whose activity is triggered by androstenone, more particularly the OR7D4 olfactory receptor.

The term "antagonist" as used herein is used to describe a compound which does not activate OR7D4, and consequently does not bring about an intracellular response. Compounds that are antagonists thereby prevent or dampen the intracellular response mediated by the interaction of androstenone with OR7D4.

The term "IC50" or "inhibitory concentration 50", as used herein, is used to describe the concentration of antagonist that induces an half decrease of the intracellular response induced upon the interaction of OR7D4 with androstenone used at 31.6 micromolar or upon the interaction of OR7D4 with any other OR7D4 activator.

The term "blocking molecule" as used herein is used to describe a compound with, preferably odourless or possessing a low odour which, when smelled, reduces or suppresses the olfactory perception of androstenone. The assays may be run in high throughput screening methods that involve providing a chemical library containing a large number of potential antagonists. Such libraries may be screened in one or more of the assays described herein to identify those library compounds (particular chemical species or subclasses) that have an effect on the response of OR7D4 to androstenone.

Antagonists thus identified can then be directly used or may serve as leads to identify further antagonists by making and testing derivatives of compounds of formula (I).

Antagonists identified by a method described herein may be tested by simple sensory experiments using trained panellists. The identified antagonist may be smelled together with androstenone, and compared to a negative control just containing androstenone.

In another aspect there is provided a kit, for example a screening kit or high throughput screening kit, for identifying compounds that antagonise the response of OR7D4 to androstenone or any other activator of this receptor, comprising:
  I. at least one recombinant cell expressing the nucleotide sequence encoding OR7D4, or a functional equivalent thereof, and
  II. androstenone or any other activator of this receptor.

The kit may be used to carry out the method, as herein disclosed, for identifying compounds that antagonise the response of OR7D4 to androstenone or to any activator of this receptor.

In another aspect there is provided a method of using the aforementioned kit to identify compounds that antagonise the response of OR7D4 to androstenone or any activator of this receptor comprising:
  I. growing at least one recombinant cell expressing the nucleotide sequence encoding OR7D4, or a functional equivalent thereof, on a solid support in a culture medium;
  II. adding one or more test compound and androstenone or any activator of this receptor to the culture medium, and
  III. measuring the effect of the test compound on the response of OR7D4 to androstenone or any activator of this receptor.

BRIEF DESCRIPTION OF DRAWING

FIG. 1 represents a graph plotting the luminescence as a function of compound 1 concentration showing the effect of compound 1 of the invention as antagonist of the OR7D4. This analysis has been performed according to the procedure given in example section.

EXAMPLES

There now follows a series of non-limiting examples that serve to illustrate the invention.

CHEMICAL EXAMPLES

The following abbreviations are used:
NaH Sodium hydride
THF Tetrahydrofuran
n-Hex n-Hexyl
h hour
RT room temperature
TLC Thin layer chromatography
HCl Hydrochloric acid
MTBE Methyl-TerButylEther
$NaHCO_3$ Sodium bicarbonate
LC-MS Liquid Chromatography-Mass Spectrometry
MS Mass Spectrometry
HPLC High Performance Liquid Chromatography
ESI Electrospray Ionisation
$NH_4OAc$ Ammonium acetate
min minute
$K_2CO_3$ Potassium Carbonate
MeI Methyl Iodide
DCM Dichloromethane
$^1$H NMR Proton Nuclear Magnetic Resonance
$^{13}$C NMR Carbon Nuclear Magnetic Resonance
EtOAc Ethyl Acetate
$AlCl_3$ Aluminium Chloride
$Et_2O$ Diethyl ether
$Na_2SO_4$ Sodium sulfate
LAH Lithium Aluminium Hydride
n-BuLi Butyl Lithium
DMSO Dimethylsulfoxide
DMSO-d6 Deuterated Dimethylsulfoxide
TEA Triethylamine
TFA trifluoroacetic acid
ACN Acetonitrile
aq aqueous
$CDCl_3$ Deuterated Chloroform
EtOH Ethanol
DIBAL-H Diisobutylaluminium hydride
DME Dimethoxyethane
MeOH Methanol
$H_2O$ Water
s singleton
d doublet
t triplet
q quadruplet
m multiplet
EDCl.HCl N-Ethyl-N'-(3-dimethylaminopropyl)carbodiimide hydrochloride
HOBt hydroxybenzotriazol
DIPEA Diisopropylethylamine
MeLi Methyl Lithium
$NH_4Cl$ Ammonium Chloride
$MgSO_4$ Magnesium sulfate
NaCl Sodium Chloride
DMF Dimethylformamide
KOH Potassium hydroxide mL Millilitres Example 1: Synthesis of ethyl (E)-4-((E)-benzylidene)-2-methyldec-2-enoate (Compound 1) (Scheme 2)

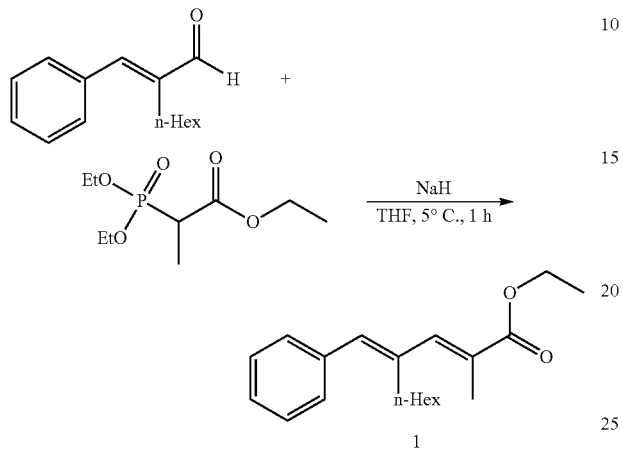

To a stirred suspension of NaH (60% dispersion in mineral oil) (188 mg, 7.86 mmol) in THF (3 mL) was added ethyl 2-(diethoxyphosphoryl)propanoate (1.5 mL, 6.94 mmol) in THF (3 mL) drop wise at 20° C. under nitrogen atmosphere. After completion of the addition, the reaction mixture was stirred at 20° C. for 1 h. Again, the mixture was cooled to 5° C. and a solution of (E)-2-benzylideneoctanal in THF (4 mL) was added. After completion of the addition, the reaction mixture was stirred at 5° C. for 1 h. The reaction was monitored by TLC; after completion of the reaction, the reaction mixture was poured into 2N HCl solution (40 mL) and extracted with MTBE (2×30 mL). Separated organic layer was washed with saturated NaHCO$_3$ solution (30 mL) and brine (30 mL). Organic layer was dried over sodium sulfate, filtered and concentrated under reduced pressure. Obtained crude material was purified through silica gel column chromatography using 10-20% EtOAc/hexanes to afford compound 1 (700 mg, 51%) as colourless liquid.

Compound 1: $^1$H NMR (400 MHz, DMSO-d$_6$) δ 7.42-7.35 (m, 2H), 7.34-7.20 (m, 3H), 7.15 (s, 1H), 6.56 (s, 1H), 4.21-4.12 (m, 2H), 2.40-2.34 (m, 2H), 2.00 (s, 3H), 1.44-1.35 (m, 2H), 1.28-1.20 (m, 9H), 0.85-0.79 (m, 3H); LC-MS (ESI): 89.60%; m/z 301.3 [M+H]$^+$ at RT 6.42 min and 10.39%; m/z 301.3[M+H]$^+$ at RT 6.08 min; (column; X-select CSH C-18 (50×3.0 mm, 2.5 μm); 2.5 mM NH$_4$OAc: ACN; 0.8 mL/min); HPLC (purity): 90.37%; (column: X SELECT CSH C-18 (150×4.6 mm, 3.5μ); RT 18.73 min; ACN: 5 Mm NH$_4$OAc; 1.0 mL/min).

Example 2: Synthesis of ethyl (2E,4E)-5-(3-methoxyphenyl)-2-methylpenta-2,4-dienoate (Compound 2) (Scheme 3)

Scheme 3

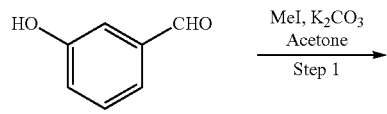

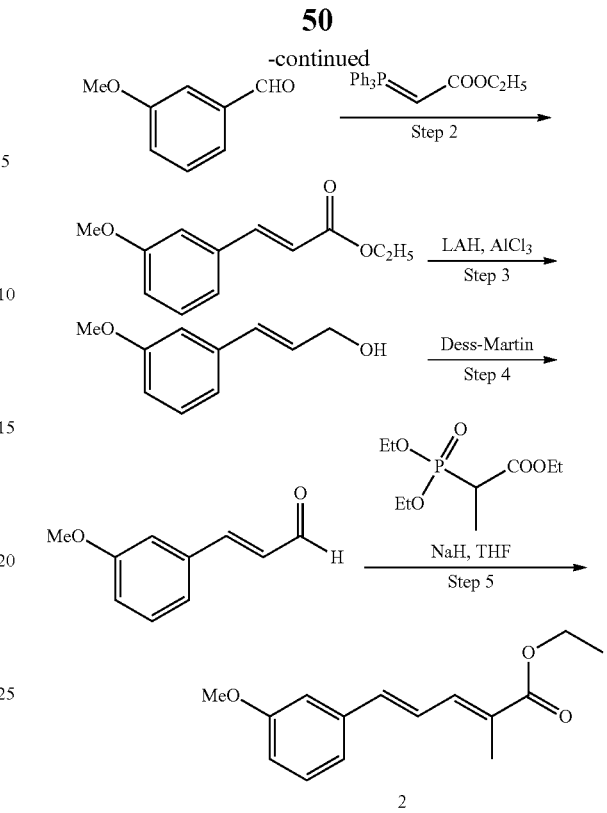

Step 1

To a solution of 3-hydroxybenzaldehyde (5 g, 40.9 mmol) in acetone (50 mL) were added K$_2$CO$_3$ (11.3 g, 81.7 mmol) followed by MeI (2.5 mL, 40.9 mmol) at room temperature under nitrogen atmosphere. The resultant reaction mixture was heated to 60° C. and stirred for 16 h. The reaction was monitored by TLC; after completion of the reaction, the reaction mixture was cooled to RT and diluted with water (50 mL) and extracted with DCM (50 mL×2). Combined organic layers were dried over sodium sulfate, filtered and concentrated under reduced pressure. Obtained crude material was purified through silica gel column chromatography using 10% EtOAc/hexanes to afford 3-methoxybenzaldehyde (4.6 g, 82%) as light yellow syrup.

3-Methoxybenzaldehyde: $^1$H NMR (500 MHz, DMSO-d$_6$): δ 9.98 (s, 1H), 7.52 (d, J=7.0 Hz, 1H), 7.50 (d, J=7.0 Hz, 1H), 7.42 (d, J=2.0 Hz, 1H), 7.28 (dt, J=7.0, 2.0 Hz, 1H), 3.83 (s, 3H); LC-MS (ESI): 99.20%; m/z 136.8 [M+H]$^+$; (column; Ascentis Express C-18 (50×3.0 mm, 2.7 μm); 0.025% Aq TFA+5% ACN:ACN+5% 0.025% Aq TFA; 1.2 mL/min).

Step 2

To a stirred solution of 3-methoxybenzaldehyde from step 1 (4.9 g, 35.5 mmol) in THF (60 mL) was added ethyl (triphenylphosphoranylidene)acetate (18.5 g, 53.2 mmol) under nitrogen atmosphere. The resultant reaction mixture was stirred room temperature for 16 h. The reaction was monitored by TLC; after completion of the reaction, the reaction mixture was diluted with water (50 mL) and extracted with EtOAc (50 mL×2). Combined organic layers were dried over sodium sulfate, filtered and concentrated under reduced pressure. Obtained crude material was purified through silica gel column chromatography using 5% EtOAc/hexanes to afford ethyl (E)-3-(3-methoxyphenyl)acrylate (6.1 g, 83%) as light yellow syrup.

Ethyl (E)-3-(3-methoxyphenyl)acrylate: $^1$H NMR (500 MHz, DMSO-$d_6$): δ 7.61 (d, J=16.0 Hz, 1H), 7.33-7.26 (m, 3H), 6.98 (dd, J=8.5, 2.0 Hz, 1H), 6.65 (d, J=16.5 Hz, 1H), 4.18 (q, J=7.0 Hz, 2H), 3.78 (s, 3H), 1.25 (t, J=7.0 Hz, 3H); LC-MS (ESI): 95.15%; m/z 207.0 [M+H]$^+$ at RT 3.41 min; (column; X-select CSH C-18 (50×3.0 mm, 2.5 μm); 2.5 mM NH$_4$OAc in water+5% ACN:ACN+5%2.5 mM NH$_4$OAc in water; 0.8 mL/min).

Step 3

To a stirred solution of LAH (189 mg, 4.85 mmol) in Et$_2$O (15 mL) was added AlCl$_3$ (647 mg, 4.85 mmol) at 0° C. under nitrogen atmosphere. After 15 minutes, ethyl (E)-3-(3-methoxyphenyl)acrylate from step 2 (1 g, 4.85 mmol) in Et$_2$O (5 mL) was added drop wise and the stirring was continued at 0° C. for 2 h. The reaction was monitored by TLC; after completion of the reaction, the reaction mixture was quenched with saturated aqueous Na$_2$SO$_4$ solution (5 mL), stirred for 30 minutes at room temperature and extracted with DCM (20 mL×2). Separated organic layer was dried over sodium sulfate, filtered and concentrated under reduced pressure. Obtained crude material was purified through silica gel column chromatography using 20% EtOAc/hexanes to afford Synthesis of (E)-3-(3-methoxyphenyl)prop-2-en-1-ol (520 mg, 72%) as light yellow syrup.

(E)-3-(3-methoxyphenyl)prop-2-en-1-ol: $^1$H NMR (500 MHz, DMSO-$d_6$): δ 7.22 (t, J=8.0 Hz, 1H), 6.99-6.96 (m, 2H), 6.80-6.78 (m, 1H), 6.51 (d, J=15.5 Hz, 1H), 6.40-6.35 (m, 1H), 4.84 (t, J=5.5 Hz, 1H), 4.11 (t, J=5.5 Hz, 2H), 3.75 (s, 3H); LC-MS (ESI): 99.55%; m/z 165.2 [M+H]$^+$ at RT 3.17 min; (column; X-select CSH C-18 (50×3.0 mm, 2.5 μm); 2.5 mM NH$_4$OAc:ACN; 0.8 mL/min).

Step 4

To a stirred solution of (E)-3-(3-methoxyphenyl)prop-2-en-1-ol from step 3 (520 mg, 3.17 mmol) in DCM (20 mL) cooled to 0° C. was added Dess-Martin Periodinane (2.68 g, 6.34 mmol) under nitrogen atmosphere. The resultant reaction mixture was stirred at RT for 2 h. The reaction was monitored by TLC; after completion of the reaction, the reaction mixture was quenched with saturated NaHCO$_3$ solution (20 mL) and extracted with DCM (20 mL×2). Separated organic layer was dried over sodium sulfate, filtered and concentrated under reduced pressure. Obtained crude material was purified through silica gel column chromatography using 10% EtOAc/hexane to afford (E)-3-(3-methoxyphenyl)acrylaldehyde (540 mg, 95%) as yellow syrup.

(E)-3-(3-methoxyphenyl)acrylaldehyde: $^1$H NMR (400 MHz, DMSO-$d_6$): δ 9.67 (d, J=7.7 Hz, 1H), 7.71 (d, J=15.9 Hz, 1H), 7.42-7.29 (m, 3H), 7.08-7.03 (m, 1H), 6.90 (dd, J=15.9, 7.7 Hz, 1H), 3.81 (s, 3H); LC-MS: 99.74%; m/z 162.8 [M+H]$^+$ at RT 3.04 min; (column; X-select CSH C-18 (50×3.0 mm, 2.5 μm); 2.5 mM NH$_4$OOCH in water+5% ACN:ACN+5%2.5 mM NH$_4$OAc in water; 0.8 mL/min).

Step 5: Synthesis of ethyl (2E,4E)-5-(3-methoxyphenyl)-2-methylpenta-2,4-dienoate (Compound 2)

To a stirred suspension of NaH (60% dispersion in mineral oil) (33 mg, 1.37 mmol) in THF (1 mL) was added ethyl 2-(diethoxyphosphoryl)propanoate (0.16 mL, 0.74 mmol) in THF (2 mL) at 20° C. under nitrogen atmosphere. After stirring for 1 h, (E)-3-(3-methoxyphenyl)acrylaldehyde (80 mg, 0.49 mmol) in THF (2 mL) was added drop wise and the stirring was continued at room temperature for 16 h. The reaction was monitored by TLC; after completion of the reaction, the reaction mixture was diluted with 2N HCl solution (10 mL) and extracted with Et$_2$O (10 mL×2). Separated organic layer was washed with saturated NaHCO$_3$, dried over sodium sulfate, filtered and concentrated under reduced pressure. Obtained crude material was purified through silica gel column chromatography using 10% EtOAc/hexanes to afford Compound 2 (95 mg, 78%) as colourless syrup.

Compound 2: $^1$H NMR (500 MHz, DMSO-$d_6$) δ 7.30-7.25 (m, 3H), 7.20-7.18 (m, 2H), 6.98 (d, J=3.5 Hz, 1H), 6.89 (dd, J=10.0, 3.0 Hz, 1H), 4.15 (q, J=7.0 Hz, 2H), 3.79 (s, 3H), 2.02 (s, 3H), 1.25 (t, J=7.0 Hz, 3H); LC-MS: 98.680%; m/z 246.9 [M+H]$^+$ at RT 2.97 min (column; Ascentis Express C-18 (50×3.0 mm, 2.7 μm); 0.025% Aq TFA+5% ACN:ACN+5% 0.025% Aq TFA; 1.2 mL/min); HPLC (purity): 88.08%; (column: ZORBAX SB C-18 (150× 4.6 mm, 3.5 μm); RT 11.70 min; ACN: 0.05% TFA; 1.0 mL/min).

Example 3: Synthesis of ethyl (2E,4E)-5-(2-propylphenyl)penta-2,4-dienoate (Compound 3) and Compound 4 (Scheme 4)

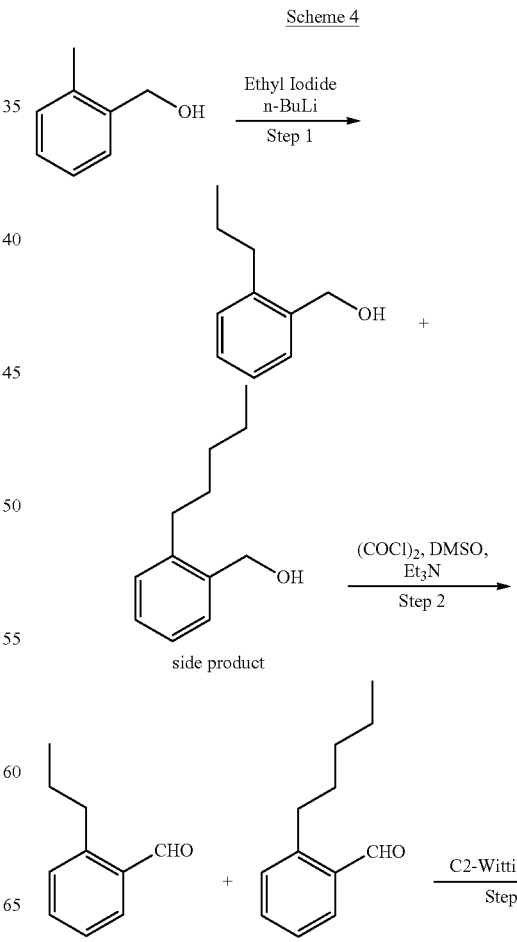

Scheme 4

53

-continued

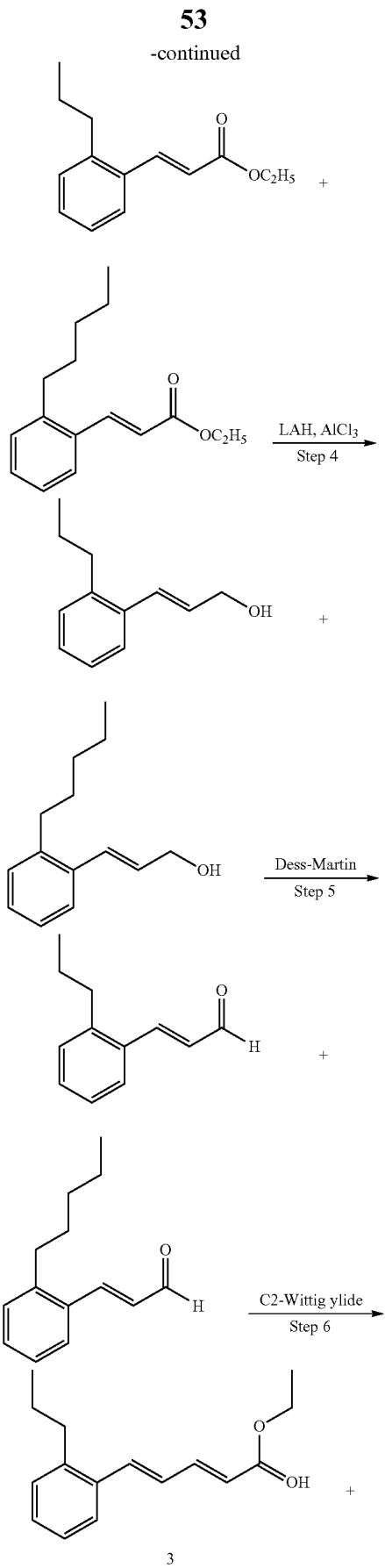

54

-continued

Step 1

To a stirred solution of o-Tolyl methanol (2 g, 16.37 mmol) in dry Et$_2$O (20 mL) was added n-BuLi (1.6M solution in hexane) (30.7 mL, 49.11 mmol) at room temperature under nitrogen atmosphere. The resultant reaction mixture was heated to reflux and stirred for 4 h. The reaction mixture was cooled to room temperature; ethyl iodine (1.3 mL, 16.37 mmol) was added and the stirring was continued at room temperature for 16 h. The reaction was monitored by TLC; after completion of the reaction, the mixture was diluted with water (30 mL) and extracted with EtOAc (30 mL×2). Combined organic layers were dried over sodium sulfate, filtered and concentrated under reduced pressure. Obtained crude material was purified through silica gel column chromatography using 10% EtOAc/hexanes to afford (2-propylphenyl)methanol (1.1 g, 46%) as syrup.

(2-propylphenyl)methanol: $^1$H NMR (500 MHz, DMSO-d$_6$): δ 7.35 (d, J=7.5 Hz, 1H), 7.16-7.11 (m, 3H), 5.02 (t, J=5.0 Hz, 1H), 4.50 (d, J=5.0 Hz, 2H), 2.58-2.53 (m, 2H), 1.56-1.50 (m, 2H), 0.92 (t, J=7.5 Hz, 3H); LC-MS (ESI): 64.65%; m/z 132.8 [M–H$_2$O+H]$^+$; (column; Ascentis Express C-18 (50×3.0 mm, 2.7 µm); 0.025% Aq TFA+5% ACN:ACN+5% 0.025% Aq TFA; 1.2 mL/min).

Step 2

To a solution of oxalyl chloride (0.5 mL, 5.33 mmol) in DCM (2 mL) was added DMSO (0.6 mL, 10.66 mmol) at −78° C. under nitrogen atmosphere and stirred for 1 h. After 1 h, (2-propylphenyl)methanol (200 mg, 1.33 mmol) in DCM (2 mL) was added drop wise and stirred for 3 h. The resultant reaction mixture was quenched with TEA (0.23 mL, 1.59 mmol) and stirred at room temperature for 1 h. The reaction was monitored by TLC; after completion of the reaction, the mixture was diluted with water (10 mL) and extracted with DCM (10 mL×2). Combined organic layers were dried over sodium sulfate, filtered and concentrated under reduced pressure. Obtained crude material 2-propylbenzaldehyde (180 mg, crude) was taken to next step without any further purification.

Step 3

To a stirred solution of 2-propylbenzaldehyde (1 g, 6.75 mmol) in THF (20 mL) was added ethyl (triphenylphosphoranylidene)acetate (3.5 g, 10.1 mmol) at RT under nitrogen atmosphere. The resultant reaction mixture was stirred room temperature for 16 h. The reaction was monitored by TLC; after completion of the reaction, volatiles were evaporated under reduced pressure. Obtained crude material was purified through silica gel column chromatography using 15%

EtOAc/hexane to afford ethyl (E)-3-(2-propylphenyl)acrylate (900 mg, 61%) as light yellow syrup.

Ethyl (E)-3-(2-propylphenyl)acrylate: $^1$H NMR (400 MHz, DMSO-$d_6$): δ 7.90 (d, J=15.9 Hz, 1H), 7.73 (d, J=7.7 Hz, 1H), 7.39-7.11 (m, 3H), 6.52 (d, J=15.9 Hz, 1H), 4.20 (q, J=7.1 Hz, 2H), 2.76-2.63 (m, 2H), 1.51 (dt, J=14.9, 7.4 Hz, 2H), 1.36-1.20 (m, 3H), 0.95-0.80 (m, 3H).

Step 4

To a stirred solution of LAH (161 mg, 4.12 mmol) in Et$_2$O (40 mL) was added AlCl$_3$ (550 mg, 4.12 mmol) at 0° C. under nitrogen atmosphere. After 15 minutes, ethyl (E)-3-(2-propylphenyl)acrylate (900 mg, 4.12 mmol) in Et$_2$O (10 mL) was added drop wise and the reaction was stirred at 0° C. for 2 h. The reaction was monitored by TLC; after completion of the reaction, the reaction mixture was quenched with 2N HCl solution (20 mL) and extracted with DCM (30 mL×2). Separated organic layer was dried over sodium sulfate, filtered and concentrated under reduced pressure. Obtained crude material was purified through silica gel column chromatography using 10% EtOAc/hexane to afford (E)-3-(2-propylphenyl)prop-2-en-1-ol (700 mg, 96%) as light yellow syrup.

(E)-3-(2-propylphenyl)prop-2-en-1-ol: $^1$H NMR (500 MHz, DMSO-$d_6$): δ 7.45 (d, J=7.5 Hz, 1H), 7.18-7.14 (m, 3H), 6.79 (d, J=16.0 Hz, 1H), 6.25-6.20 (m, 1H), 4.85 (t, J=5.5 Hz, 1H), 4.13 (d, J=5.5 Hz, 2H), 2.63-2.59 (m, 2H), 1.54-1.46 (m, 2H), 0.90 (t, J=7.5 Hz, 3H).

Step 5: Synthesis of (E)-3-(2-propylphenyl)acrylaldehyde

To a stirred solution of (E)-3-(2-propylphenyl)prop-2-en-1-ol (890 mg, 5.05 mmol) in DCM (50 mL) cooled to 0° C., was added Dess-Martin Periodinane (4.2 g, 10.1 mmol) portion wise under nitrogen atmosphere. The resultant reaction mixture was stirred at room temperature for 2 h. The reaction was monitored by TLC. After completion of the reaction, the reaction mixture was quenched with saturated NaHCO$_3$ solution (20 mL) and extracted with DCM (20 mL×2). Separated organic layer was dried over sodium sulfate, filtered and concentrated under reduced pressure. Obtained crude material (compound A) (1.1 g, crude) was taken to next step without any further purification.

Step 6: Synthesis of ethyl (2E,4E)-5-(2-propylphenyl)penta-2,4-dienoate (Compound 3) and ethyl (2E,4E)-5-(2-pentylphenyl)penta-2,4-dienoate (Compound 4)

To a stirred solution of compound A (1.1 g, 6.31 mmol) in THF (40 mL) was added C$_2$-Wittig ylide (3.2 g, 9.47 mmol) at under nitrogen atmosphere. The resultant reaction mixture was stirred at room temperature for 16 h. The reaction was monitored by TLC; after completion of the reaction, volatiles were evaporated under reduced pressure. Obtained crude material was purified through silica gel column chromatography using 5% EtOAc/hexane to afford mixture of products (1 g), which was separated by preparative HPLC to obtain Compound 3 (260 mg, 17%) and Compound 4 as a by-product (180 mg, 12%) as colourless syrup.

Compound 3: $^1$H NMR (500 MHz, DMSO-$d_6$): δ 7.64 (d, J=7.0 Hz, 1H), 7.55-7.50 (m, 1H), 7.39 (d, J=15.0 Hz, 1H), 7.27-7.19 (m, 3H), 7.05-6.99 (m, 1H), 6.07 (d, J=15.5 Hz, 1H), 4.15 (q, J=7.0 Hz, 2H), 2.70-2.67 (m, 2H), 1.52-1.48 (m, 2H), 1.24 (t, J=7.0 Hz, 3H), 0.91 (t, J=7.5 Hz, 3H); LC-MS: 99.76%; m/z 244.9 [M+H]$^+$ at RT 3.24 min (column; Ascentis Express C-18 (50×3.0 mm, 2.7 μm); 0.025% Aq TFA+5% ACN:ACN+5% 0.025% Aq TFA; 1.2 mL/min); HPLC (purity): 99.74%; (column: XSELECT CSH C-18 (150×4.6 mm, 3.5 μm); RT 12.83 min; ACN: 0.5% TFA; 1.0 mL/min).

Compound 4: $^1$H NMR (400 MHz, DMSO-$d_6$): δ 7.67-7.61 (m, 1H), 7.52 (dd, J=15.2, 11.0 Hz, 1H), 7.39 (d, J=15.4 Hz, 1H), 7.27-7.17 (m, 3H), 7.02 (dd, J=15.3, 11.0 Hz, 1H), 6.08 (d, J=15.3 Hz, 1H), 4.20-4.06 (m, 2H), 2.74-2.65 (m, 2H), 1.53-1.42 (m, 2H), 1.34-1.27 (m, 4H), 1.24 (t, J=7.1 Hz, 3H), 0.89-0.82 (m, 3H); LC-MS: 99.88%; m/z 273.0 [M+H]$^+$ at RT 3.50 min (column; Ascentis Express C-18 (50×3.0 mm, 2.7 μm); 0.025% Aq TFA+5% ACN:ACN+5% 0.025% Aq TFA; 1.2 mL/min); HPLC (purity): 99.53%; (column: XSELECT CSH C-18 (150×4.6 mm, 3.5 μm); RT 14.32 min; ACN: 0.5% TFA; 1.0 mL/min).

Example 4: Synthesis of ethyl (E)-4-((E)-4-fluorobenzylidene)dec-2-enoate (Compound 5) (Scheme 5)

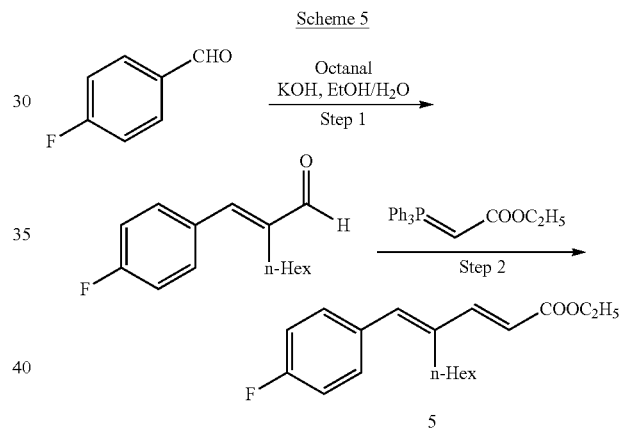

Step 1: Synthesis of (E)-2-(4-fluorobenzylidene)octanal

To a solution of octanal (3.5 mL, 23.4 mmol) in EtOH:H$_2$O (40 mL, 1:1) were added KOH (1.31 g, 23.4 mmol) and 4-fluorobenzaldehyde (2 g, 15.1 mmol) at 0° C. and the mixture was stirred for 16 h. The reaction was monitored by TLC; after completion of the reaction, ethanol was removed. Crude material was diluted with water (30 mL) and extracted with DCM (2×30 mL). Separated organic layer was dried over sodium sulfate, filtered and concentrated under reduced pressure. Obtained crude material was purified through silica gel column chromatography using 3% EtOAc/hexanes to afford (E)-2-(4-fluorobenzylidene)octanal (550 mg, 15%) as light yellow syrup.

$^1$H NMR (500 MHz, CDCl$_3$): δ 9.55 (s, 1H), 7.51 (dd, J=8.4, 5.5 Hz, 2H), 7.33-7.29 (m, 1H), 7.19-7.13 (m, 1H), 7.03-6.99 (m, 1H), 2.55-2.50 (m, 2H), 1.42-1.24 (m, 8H), 0.86 (t, J=6.7 Hz, 3H); LC-MS (ESI): 96.27%; m/z 235.0 [M+H]$^+$ at RT 3.25 min; (column; Ascentis Express C-18 (50×3.0 mm, 2.7 μm); 0.025% Aq TFA+5% ACN:ACN+5% 0.025% Aq TFA; 1.2 mL/min).

Step 2: Synthesis of ethyl (E)-4-((E)-4-fluorobenzylidene)dec-2-enoate

To a stirred solution of (E)-2-(4-fluorobenzylidene)octanal from step 1 (850 mg, 3.63 mmol) in toluene (20 mL) was added ethyl (triphenylphosphoranylidene)acetate (2.53 g, 7.26 mmol) in a sealed tube under nitrogen atmosphere. The reaction mixture was heated to 90° C. and stirred for 16 h. The reaction was monitored by TLC; after completion of the reaction, volatiles were evaporated under reduced pressure. Obtained crude material was purified through silica gel column chromatography using 5% EtOAc/hexanes followed by preparative HPLC to afford ethyl (E)-4-((E)-4-fluorobenzylidene)dec-2-enoate (250 mg, 22%) light yellow syrup.

Compound 5: $^1$H NMR (500 MHz, CDCl$_3$): δ 7.38 (d, J=15.9 Hz, 1H), 7.29 (dd, J=8.5, 5.6 Hz, 2H), 7.07 (t, J=8.7 Hz, 2H), 6.75 (s, 1H), 5.98 (d, J=15.9 Hz, 1H), 4.25 (q, J=7.0 Hz, 2H), 2.46-2.40 (m, 2H), 1.54-1.48 (m, 3H), 1.39-1.27 (m, 8H), 0.89 (t, J=6.8 Hz, 3H); LC-MS (ESI): 99.90%; m/z 305.1 [M+H]$^+$ at RT 3.59 min; (column; X-select CSH C-18 (50×3.0 mm, 2.7 μm); (column; Ascentis Express C-18 (50×3.0 mm, 2.7 μm); 0.025% Aq TFA+5% ACN:ACN+5% 0.025% Aq TFA; 1.2 mL/min); HPLC (purity): 98.01%; (column: X SELECT CSH C-18 (150×4.6 mm, 3.5μ); RT 15.61 min; ACN+5 mM NH$_4$OAc; 1.0 mL/min).

Example 5: Synthesis of ethyl (E)-4-((E)-2-ethoxybenzylidene)-2-methylhex-2-enoate (Compound 6) (Scheme 6)

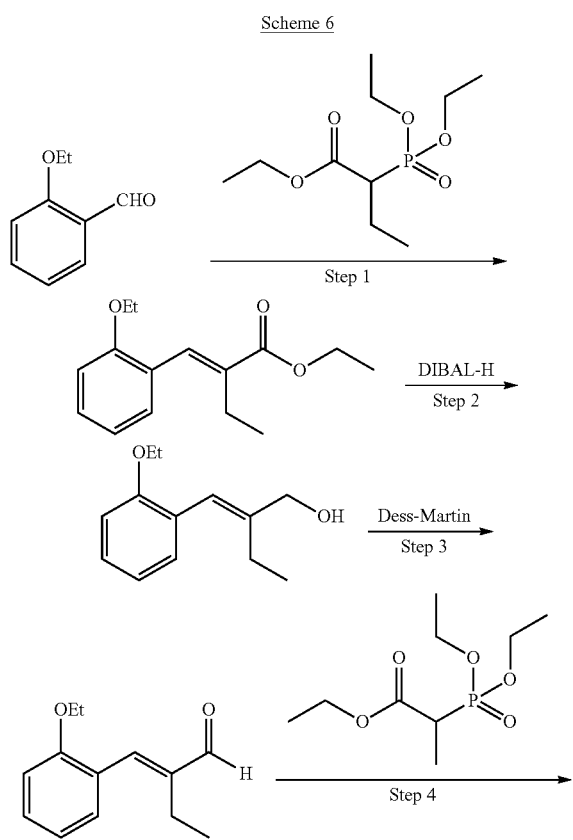

Scheme 6

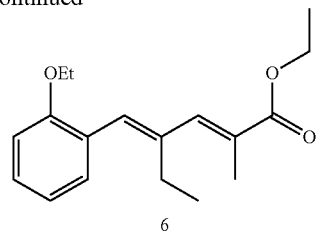

6

Step 1

To a stirred suspension of NaH (60% dispersion in mineral oil) (226 mg, 5.66 mmol) in THF (7 mL) was added ethyl 2-(diethoxyphosphoryl)butanoate (1.18 mL, 4.95 mmol) in THF (3 mL) drop wise at 0° C. under nitrogen atmosphere. After completion of the addition, the reaction mixture was stirred at RT for 1 h. Again, the mixture was cooled to 0° C. and 2-ethoxybenzaldehyde (500 mg, 3.33 mmol) was added and the mixture was stirred at RT for 16 h. The reaction was monitored by TLC; after completion of the reaction, the reaction mixture was quenched with cold water (20 mL) and extracted with EtOAc (3×20 mL). Separated organic layer was washed with saturated NaHCO$_3$ solution (30 mL) and brine (30 mL). Organic layer was dried over sodium sulfate, filtered and concentrated under reduced pressure. Obtained crude material was purified through silica gel column chromatography using 4% EtOAc/hexane to afford ethyl (E)-2-(2-ethoxybenzylidene)butanoate (500 mg, 60%) as colourless syrup.

ethyl (E)-2-(2-ethoxybenzylidene)butanoate: $^1$H NMR (400 MHz, CDCl$_3$): δ 7.28-7.26 (m, 1H), 7.23-7.14 (m, 1H), 6.97-6.78 (m, 3H), 4.28 (q, J=7.1 Hz, 2H), 4.11-4.00 (m, 2H), 2.52-2.44 (m, 2H), 1.45-1.40 (m, 3H), 1.35 (t, J=7.2 Hz, 3H), 1.18-1.13 (m, 3H); LC-MS (ESI): 70.79%; m/z 249.0 [M+H]$^+$ at RT 3.09 min; (column; column; Ascentis Express C-18 (50×3.0 mm, 2.7 μm); 0.025% Aq TFA+5% ACN:ACN+5% 0.025% Aq TFA; 1.2 mL/min).

Step 2

To a stirred solution of (E)-2-(2-ethoxybenzylidene)butanoate from step 1 (300 mg, 1.21 mmol) in DCM (10 mL) was added DIBAL-H (1.6 mL, 1.81 mmol) drop wise at −78° C. under nitrogen atmosphere. The reaction mixture was stirred at −78° C. for 4 h. The reaction was monitored by TLC; after completion of the reaction, the reaction mixture was quenched with saturated aqueous sodium potassium tartrate solution (50 mL), stirred for 30 minutes at room temperature and extracted with DCM (20 mL×2). Separated organic layer was dried over sodium sulfate, filtered and concentrated under reduced pressure to afford (E)-2-(2-ethoxybenzylidene)butan-1-ol (220 mg, 88%) as colourless syrup.

(E)-2-(2-ethoxybenzylidene)butan-1-ol: $^1$H NMR (500 MHz, CDCl$_3$): δ 7.25-7.15 (m, 2H), 6.96-6.87 (m, 2H), 6.59

(s, 1H), 6.43 (s, 1H), 4.29 (d, J=5.5 Hz, 2H), 4.10-4.03 (m, 2H), 2.32 (q, J=7.5 Hz, 2H), 1.43 (t, J=7.1 Hz, 3H), 1.12 (t, J=7.7 Hz, 3H); HPLC (purity): 73.87%; (column: X SELECT CSH C-18 (150×4.6 mm, 3.5µ); RT 10.80 min; ACN+5 mM NH₄OAc; 1.0 mL/min).

Step 3

A solution of (E)-2-(2-ethoxybenzylidene)butan-1-ol from step 2 (300 mg, 1.45 mmol) in DCM (10 mL) was cooled to 0° C. and then added Dess-Martin Periodinane (1.1 g, 2.44 mmol) under nitrogen atmosphere. The resultant reaction mixture was stirred at RT for 2 h. The reaction was monitored by TLC; after completion of the reaction, the reaction mixture was quenched with saturated NaHCO₃ solution (10 mL) and extracted with DCM (10 mL×2). Separated organic layer was dried over sodium sulfate, filtered and concentrated under reduced pressure. Obtained crude material was purified through silica gel column chromatography using 10% EtOAc/hexane to afford (E)-2-(2-ethoxybenzylidene)butanal. (270 mg, 90%) as yellow syrup.

(E)-2-(2-ethoxybenzylidene)butanal: ¹H NMR (400 MHz, CDCl₃): δ 9.58 (s, 1H), 7.64-7.55 (m, 1H), 7.48-7.45 (m, 1H), 7.38-7.31 (m, 1H), 7.18-7.15 (m, 1H), 7.02-6.97 (m, 1H), 4.14-4.05 (m, 2H), 2.51 (q, J=7.5 Hz, 2H), 1.46 (t, J=7.0 Hz, 3H), 1.16-1.11 (m, 3H); LC-MS: 97.32%; m/z 204.9 [M+H]⁺ at RT 2.90 min; (column; X-select CSH C-18 (50×3.0 mm, 2.5 µm); 0.025% Aq TFA+5% ACN:ACN+5% 0.025% Aq TFA; 1.2 mL/min); HPLC (purity): 95.55%; (column: X SELECT CSH C-18 (150×4.6 mm, 3.5µ); RT 11.42 min; ACN+5% 0.05% TFA: 0.05% TFA+5% ACN; 1.0 mL/min).

Step 4: Synthesis of ethyl (E)-4-((E)-2-ethoxybenzylidene)-2-methylhex-2-enoate (Compound 6)

To a stirred suspension of NaH (60% dispersion in mineral oil) (105 mg, 1.70 mmol) in THF (20 mL) was added ethyl 2-(diethoxyphosphoryl)propanoate (0.49 mL, 2.30 mmol) at 0° C. under nitrogen atmosphere and the mixture was stirred at room temperature for 1 h. Again the reaction mixture was cooled 0° C. and (E)-2-(2-ethoxybenzylidene) butanal (270 mg, 1.55 mmol) was added and the mixture was stirred at room temperature for 16 h. The reaction was monitored by TLC; after completion of the reaction, the reaction mixture was quenched with water (20 mL) and extracted with EtOAc (2×20 mL). Separated organic layer was washed with saturated NaHCO₃, dried over sodium sulfate, filtered and concentrated under reduced pressure. Obtained crude material was purified through silica gel column chromatography using 3% EtOAc/hexanes followed by preparative HPLC to afford ethyl (E)-4-((E)-2-ethoxybenzylidene)-2-methylhex-2-enoate 6 (80 mg, 18%) as colourless syrup. The trans geometry is confirmed by NOE analysis.

Compound 6: ¹H NMR (500 MHz, CDCl₃): δ 7.26-7.21 (m, 3H), 6.93 (t, J=7.5 Hz, 1H), 6.87 (d, J=8.1 Hz, 1H), 6.57 (s, 1H), 4.25 (q, J=7.0 Hz, 2H), 4.04 (q, J=6.9 Hz, 2H), 2.36 (q, J=7.5 Hz, 2H), 2.10 (d, J=1.2 Hz, 3H), 1.40 (t, J=6.9 Hz, 3H), 1.34 (t, J=7.2 Hz, 3H), 1.05 (t, J=7.5 Hz, 3H); LC-MS: 99.97%; m/z 289.0 [M+H]⁺ at RT 3.44 min (column; Ascentis Express C-18 (50×3.0 mm, 2.7 µm); 0.025% Aq TFA+5% ACN:ACN+5% 0.025% Aq TFA; 1.2 mL/min); HPLC (purity): 91.34%; (column: XSELECT CSH C-18 (150×4.6 mm, 3.5 µm); RT 14.13 min; ACN: 5 mM NH4OAc; 1.0 mL/min).

Example 6: Synthesis of ethyl (E)-4-((E)-4-cyanobenzylidene)-2-methyldec-2-enoate (Compound 7) (Scheme 7)

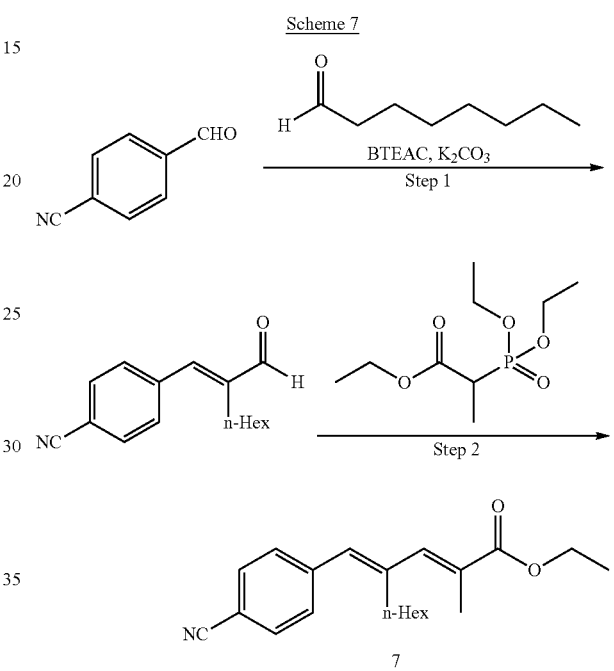

Step 1

To a solution of octanal (0.6 mL, 3.81 mmol) in DCM (20 mL) were added K₂CO₃ (2.6 g, 19.1 mmol), 4-isocyanobenzaldehyde (500 mg, 3.81 mmol) and benzyltriethyl ammonium chloride (434 mg, 1.91 mmol) at room temperature and the mixture was stirred for 16 h. The reaction was monitored by TLC; after completion of the reaction, the mixture was diluted with water (20 mL) and extracted with DCM (2×20 mL). Separated organic layer was dried over sodium sulfate, filtered and concentrated under reduced pressure. Obtained crude material was purified through silica gel column chromatography using 5% EtOAc/hexanes to afford (E)-4-(2-formyloct-1-en-1-yl)benzonitrile (620 mg, 67%) as light yellow syrup.

(E)-4-(2-formyloct-1-en-1-yl)benzonitrile: ¹H NMR (400 MHz, CDCl₃): δ 9.58 (s, 1H), 7.74 (d, J=8.3 Hz, 2H), 7.56 (d, J=8.2 Hz, 2H), 7.21 (s, 1H), 2.52-2.42 (m, 2H), 1.40-1.21 (m, 8H), 0.88 (t, J=6.8 Hz, 3H); LC-MS (ESI): 97.44%; m/z 240.3 [M–H]⁺ at RT 4.63 min; (column; X-select CSH C-18 (50×3.0 mm, 2.5 µm); 2.5 mM AqNH₄OAc:ACN; 0.8 mL/min); HPLC (purity): 94.20%; (column: X SELECT CSH C-18 (150×4.6 mm, 3.5µ); RT 12.48 min; ACN: 5 mM NH₄OAc; 1.0 mL/min).

Step 2: Synthesis of ethyl (E)-4-((E)-4-cyanobenzylidene)-2-methyldec-2-enoate (Compound 7)

To a stirred suspension of NaH (60% dispersion in mineral oil) (84 mg, 3.50 mmol) in THF (5 mL) was added ethyl 2-(diethoxyphosphoryl)propanoate (0.4 mL, 1.86 mmol) at 0° C. under nitrogen atmosphere. The mixture was stirred at room temperature for 1 h. Again the reaction mixture was cooled to 0° C., and (E)-4-(2-formyloct-1-en-1-yl)benzonitrile (300 mg, 1.24 mmol) in THF (5 mL) was added. The mixture was stirred at room temperature for 16 h. The reaction was monitored by TLC; after completion of the reaction, the reaction mixture was quenched with water (15 mL) and extracted with EtOAc (2×20 mL). Separated organic layer was washed with saturated NaHCO$_3$, dried over sodium sulfate, filtered and concentrated under reduced pressure. Obtained crude material was purified through silica gel column chromatography using 5% EtOAc/hexanes followed by preparative HPLC to afford compound 7 (120 mg, 30%) as colourless syrup.

Compound 7: $^1$H NMR (400 MHz, CDCl$_3$): δ 7.64 (d, J=8.4 Hz, 2H), 7.36 (d, J=8.0 Hz, 2H), 7.21-7.17 (m, 1H), 6.45 (s, 1H), 4.25 (q, J=7.1 Hz, 2H), 2.38-2.31 (m, 2H), 2.05 (d, J=1.5 Hz, 3H), 1.49-1.40 (m, 4H), 1.34 (t, J=7.2 Hz, 3H), 1.31-1.27 (m, 4H), 0.87 (t, J=6.8 Hz, 3H); LC-MS (ESI): 13.18%; m/z 326.4 [M+H]$^+$ at RT 5.48 min and 86.81%; m/z 326.4 [M+H]$^+$ at RT 5.59 min; (column: X-select CSH C-18 (50×3.0 mm, 2.5 μm); 2.5 mM Aq. NH$_4$OAc:ACN; 0.8 mL/min); HPLC (purity): 10.29 & 86.63%; (column: X SELECT CSH C-18 (150×4.6 mm, 3.5μ); RT 14.42 & 14.75 min; ACN: 5 mM NH$_4$OAc; 1.0 mL/min).

Compounds 8-15 have been prepared following the same chemical route and using the reagent described in the following table 2 (Scheme 8)

Compound 8: $^1$H NMR (500 MHz, CDCl$_3$): δ 7.38-7.33 (m, 2H), 7.29-7.23 (m, 3H), 7.21 (s, 1H), 6.51 (s, 1H), 5.83-5.73 (m, 1H), 5.03-4.91 (m, 2H), 4.25 (q, J=7.0 Hz, 2H), 2.43-2.36 (m, 2H), 2.07 (d, J=1.2 Hz, 3H), 2.05-2.01 (m, 2H), 1.52-1.37 (m, 4H), 1.34 (t, J=7.0 Hz, 3H).

Compound 9: $^1$H NMR (300 MHz, CDCl3) δ 7.44-7.14 (m, 6H), 6.49 (s, 1H), 4.25 (q, J=7.1 Hz, 2H), 2.43-2.30 (m, 2H), 2.07 (d, J=1.5 Hz, 3H), 1.46 (dd, J=10.0, 5.4 Hz, 4H), 1.31 (ddd, J=14.4, 10.4, 7.1 Hz, 7H), 0.94-0.77 (m, 3H)

Compound 10: $^1$H NMR (300 MHz, CDCl3) δ 7.60-7.16 (m, 6H), 6.80 (s, 1H), 5.99 (d, J=15.8 Hz, 1H), 3.79 (s, 3H), 2.53-2.38 (m, 2H), 1.63-1.20 (m, 8H), 0.89 (t, J=6.7 Hz, 3H).

Compound 11: $^1$H NMR (400 MHz, CDCl$_3$): δ 7.40-7.33 (m, 3H), 7.28-7.25 (m, 3H), 6.36 (s, 1H), 4.26 (q, J=7.2 Hz, 2H), 3.10-3.14 (m, 1H), 2.07 (d, J=1.5 Hz, 3H), 1.50 (dd, J=7.3, 14.1 Hz, 1H), 1.35 (t, J=7.2 Hz, 3H), 1.16 (d, J=4.5 Hz, 1H), 1.12 (d, J=7.0 Hz, 3H), 0.73 (s, 9H).

Compound 12: $^1$H NMR (500 MHz, CDCl$_3$): δ 7.39-7.34 (m, 2H), 7.31 (s, 2H), 7.29-7.24 (m, 2H), 6.52 (s, 1H), 4.26 (q, J=7.3 Hz, 2H), 2.45 (d, J=7.5 Hz, 2H), 2.10 (d, J=1.7 Hz, 3H), 2.01-1.92 (m, 1H), 1.76-1.68 (m, 2H), 1.54-1.46 (m, 4H), 1.35 (t, J=7.3 Hz, 3H), 1.14-1.05 (m, 2H).

Compound 13: $^1$H NMR (300 MHz, CDCl3) δ 7.84-7.67 (m, 6H), 7.47-7.16 (m, 2H), 6.79 (d, J=4.9 Hz, 1H), 6.02 (dd, J=22.7, 15.9 Hz, 1H), 4.22 (dq, J=14.2, 7.1 Hz, 2H), 2.52-2.32 (m, 2H), 1.62-1.49 (m, 2H), 1.31 (dt, J=8.9, 7.2 Hz, 7H), 0.89 (dd, J=8.2, 4.8 Hz, 3H)

Compound 14: $^1$H NMR (300 MHz, CDCl3) δ 7.47-7.21 (m, 6H), 6.80 (s, 1H), 5.98 (d, J=15.7 Hz, 1H), 4.25 (q, J=7.1 Hz, 2H), 2.53-2.40 (m, 2H), 1.64-1.19 (m, 9H), 0.96-0.83 (m, 3H)

Compound 15: $^1$H NMR (300 MHz, CDCl3) δ 7.50-7.16 (m, 5H), 6.81 (s, 1H), 5.98 (d, J=15.7 Hz, 1H), 4.25 (q, J=7.1 Hz, 2H), 2.42 (ddd, J=23.1, 11.8, 6.8 Hz, 2H), 1.70-1.47 (m, 2H), 1.33 (t, J=7.1 Hz, 3H), 0.99 (t, J=6.2 Hz, 3H).

Example 7: Synthesis of 4-benzylidenedec-2-enenitrile (Compound 16) (Scheme 9)

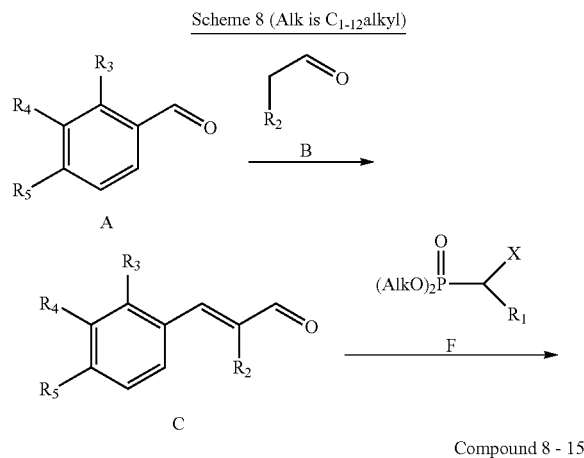

Scheme 8 (Alk is C$_{1-12}$alkyl)

Compound 8 - 15

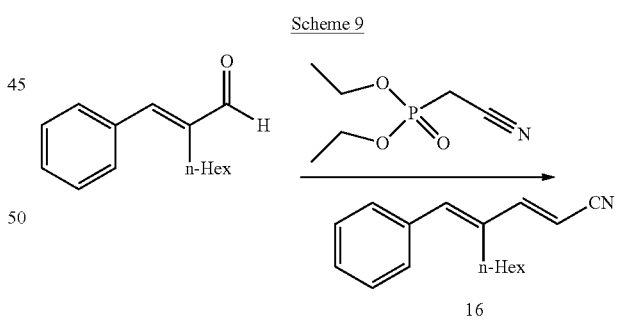

Scheme 9

TABLE 2

| Compound | Aldehyde A | Aldehyde B | Phosphonate F |
|---|---|---|---|
| 8 | Benzaldehyde | 7-Octenal | Ethyl 2-(diethoxyphosphoryl)propanoate |
| 9 | | Heptanal | |
| 10 | | Octanel | Methyl (diethoxyphosphoryl) acetate |
| 11 | | 3,5,5-trimethylhexanal | Ethyl 2-(diethoxyphosphoryl)propanoate |
| 12 | | 3-cyclopentyl pentanel | |
| 13 | | Octanel | Ethyl (diethoxyphosphoryl)acetate |
| 14 | | Heptanal | |
| 15 | | Pentanel | |

A suspension of sodium hydride (2.24 g, 55% dispersion in mineral oil, 51.3 mmol, 1.1 eq., washed twice with hexane) in 1,2-dimethoxyethane (DME, 100 ml) was treated dropwise with a solution of diethylcyanomethyl phosphonate (8.2 ml, 51.1 mmol, 1.1 eq.) in DME (10 ml). The resulting mixture was stirred for 1 h at 20° C., treated dropwise with a solution of alpha-hexyl-cinnamic aldehyde (10 g, 46.2 mmol) in DME (20 ml), stirred at 60° C. for 3 h, cooled to 20° C., poured into 2N aq. HCl/ice (200 ml), and extracted twice with MTBE (75 ml). The combined organic phases were washed three times with water (75 ml), four times with aqueous saturated NaCl solution (75 ml), dried (MgSO$_4$), and concentrated. The crude yellow/orange oil (12.3 g) was distilled using a ball-to-ball distillation apparatus (Kugelrohr, 160-200° C. oven temperature, 0.06-0.07 mbar) and the fraction distilled at 180-200° C. (0.06-0.07 mbar, 7.31 g, 86:10:4 mixture of isomers, light yellow solid) was distilled again using the same apparatus (190-220° C. oven temperature, 0.06 mbar) giving pure 4-benzylidene-dec-2-enenitrile (5.95 g, 54%, 83:13:4 mixture of isomers) as a white solid.

Compound 16: $^1$H-NMR (CDCl$_3$, 400 MHz): δ 7.42-7.36 (m, 2H), 7.35-7.28 (m, 3H), 7.10 (dd, J=0.8, 16.4, 1H), 6.73 (br. s, 1H), 5.41 (br. d, J=16.4, 1H), 2.45-2.39 (m, 2H), 1.56-1.46 (m, 2H), 1.42-1.24 (m, 6H), 0.89 (t, J=6.8, Me). $^{13}$C-NMR (CDCl$_3$, 100 MHz): δ 154.79 (d), 139.42 (d), 138.50 (s), 135.91 (s), 129.11 (d, 2C), 128.58 (d, 2C), 128.28 (d), 118.70 (s), 94.94 (d), 31.44 (t), 29.47 (t), 28.55 (t), 26.63 (t), 22.57 (t), 14.01 (q). MS (EI): m/z 240 [M+H]$^+$ Compounds 17 and 18 have been prepared following the same chemical route and using the reagent described in the following table 3 (Scheme 10).

Scheme 10 (Alk is C$_{1-12}$alkyl)

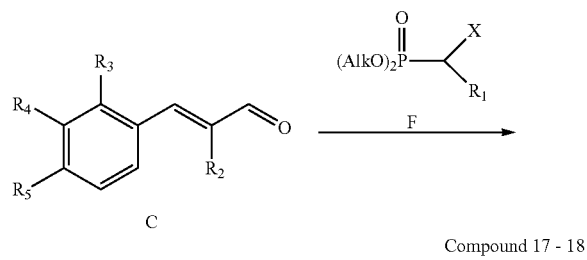

Compound 17 - 18

TABLE 3

| Compound | Aldehyde C | Phosphonate F |
|---|---|---|
| 17 | Hexyl cinnamaldehyde | Diethyl (1-cyanoethyl)phosphonate |
| 18 | 2-Benzylideneheptanal | Diethylcyanomethyl phosphonate |

Compound 17 $^1$H-NMR (300 MHz, CDCl3) δ 7.43-7.20 (m, 5H), 6.76 (s, 1H), 6.54 (dd, J=10.9, 9.7 Hz, 1H), 2.64-2.27 (m, 2H), 1.55 (s, 3H) 1.5-1.2 (m, 8H), 0.87 (t, J=6.0 Hz, 3H)

Compound 18 $^1$H-NMR (300 MHz, CDCl3) δ 7.52-7.26 (m, 5H), 7.11 (d, J=16.4 Hz, 1H), 6.75 (s, 1H), 5.41 (d, J=16.4 Hz, 1H), 2.51-2.35 (m, 2H), 1.66-1.44 (m, 2H), 1.36 (m, 4H), 1.02-0.81 (m, 3H)

Example 8: Synthesis of (E)-4-((E)-4-cyanobenzylidene)-2-methyldec-2-enoic Acid (Compound 19) (Scheme 11)

Scheme 11

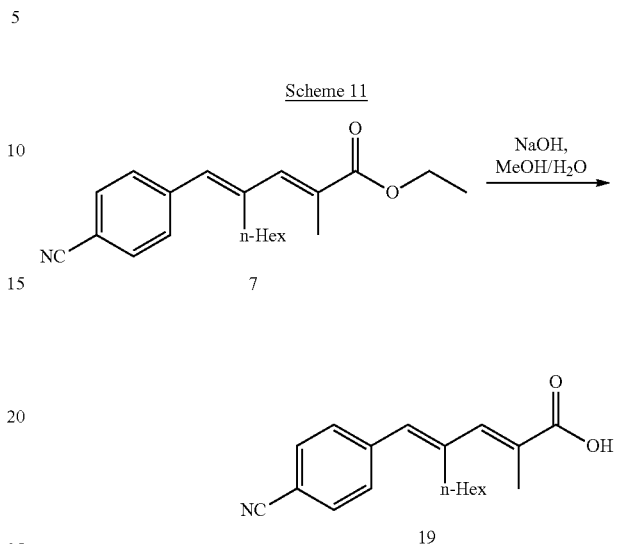

To a stirred solution of ethyl (E)-4-((E)-4-cyanobenzylidene)-2-methyldec-2-enoate (Compound 7) (30 mg, 0.09 mmol) in MeOH:H$_2$O (4 mL, 1:1) was added NaOH (7 mg, 0.18 mmol) at room temperature. The reaction mixture was heated to reflux for 3 h. The reaction was monitored by TLC; after completion of the reaction, methanol solvent was removed under reduced pressure. The reaction mixture was diluted with water (5 mL) and acidified with 2N HCl solution (pH-2) and extracted with EtOAc (2×10 mL). Combined organic layer was dried over sodium sulfate, filtered and concentrated under reduced pressure. Obtained crude material was purified preparative TLC to afford Compound 19 (10 mg, 36%) as colourless syrup.

Compound 19: $^1$H NMR (400 MHz, CDCl$_3$) δ 7.67-7.63 (m, 2H), 7.37 (d, J=8.0 Hz, 2H), 7.31-7.29 (m, 1H), 6.50 (s, 1H), 2.39-2.33 (m, 2H), 2.08 (d, J=1.4 Hz, 3H), 1.48-1.41 (m, 4H), 1.30-1.28 (m, 4H), 0.89-0.85 (m, 3H); LC-MS (ESI): 97.30%; m/z 296.1 [M−H]$^+$ at RT 3.77 min; (column; X-select CSH C-18 (50×3.0 mm, 2.5 μm); 2.5 mM NH$_4$OOCH in water+5% ACN:ACN+5%2.5 mM NH$_4$OOCH in water; 0.8 mL/min); HPLC (purity): 95.18%; (column: X SELECT CSH C-18 (150×4.6 mm, 3.5μ); RT 10.34 min; ACN: 5 mM NH$_4$OAc; 1.0 mL/min).

Compound 20 from compound 6: $^1$H NMR (500 MHz, CDCl$_3$): δ 7.38 (s, 1H), 7.26-7.22 (m, 2H), 6.97-6.92 (m, 1H), 6.88 (d, J=8.1 Hz, 1H), 6.64 (s, 1H), 4.05 (q, J=6.9 Hz, 2H), 2.39 (q, J=7.4 Hz, 2H), 2.12 (s, 3H), 1.41 (br t, J=6.9 Hz, 3H), 1.07 (t, J=7.5 Hz, 3H); LC-MS (ESI): 99.76%; m/z 259.1 [M−H]$^+$ at RT 3.48 min; (column; X-select CSH C-18 (50×3.0 mm, 2.5 μm); 2.5 mM NH$_4$OOCH in water+5% ACN:ACN+5%2.5 mM NH$_4$OOCH in water; 0.8 mL/min); HPLC (purity): 99.75%; (column: ZORBAX SB C-18 (150× 4.6 mm, 3.5 μm); RT 11.04 min; ACN+0.05% TFA: 0.05% TFA+ACN; 1.0 mL/min).

Example 9: Synthesis of 4-benzylidene-2-methyldec-2-enoic Acid (Compound 21) from Compound 1 (Scheme 12)

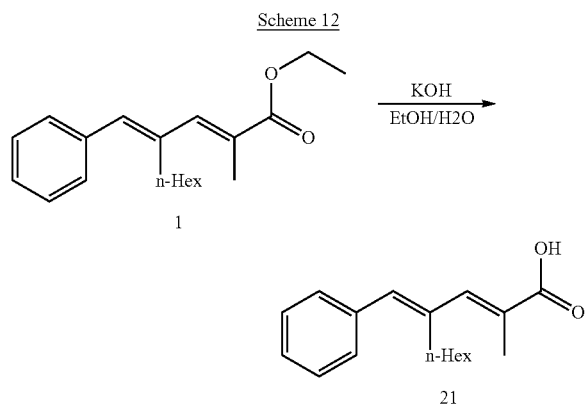

Ethyl 4-benzylidene-2-methyldec-2-enoate 1 (2.7 g, 8.99 mmol) was treated at 0° C., with a solution of KOH (0.84 g, 13.5 mmol) in a mixture of EtOH (19 ml) and water (8 ml). The resulting suspension was stirred at 20° C. for 24 h, washed with hexane (50 ml) and the aqueous phase acidified with 2N HCl/ice (50 ml) and extracted three times with MTBE (50 ml). The combined organic phases were washed once with aq. saturated NaCl solution, dried (MgSO₄), and concentrated giving crude 4-benzylidene-2-methyldec-2-enoic acid 21 (2.38 g, 97%, 81:13:6 mixture of isomers) as a brown oil.

Compound 21 (major isomer); $^1$H-NMR (CDCl$_3$, 400 MHz): d 8.90-8.50 (br. s, 1H), 7.40-7.32 (m, 3H), 7.31-7.22 (m, 3H), 6.55 (br. s, 1H), 2.44-2.37 (m, 2H), 2.09 (d, J=1.3, Me), 1.52-1.41 (m, 2H), 1.36-1.21 (m, 6H), 0.87 (t, J=6.9, Me). $^{13}$C-NMR (CDCl$_3$, 100 MHz): δ 174.12 (s), 144.61 (d), 138.98 (s), 136.97 (s), 132.57 (d), 128.84 (d, 2C), 128.30 (d, 2C), 127.15 (d and s), 31.58 (t), 31.33 (t), 29.22 (t), 28.88 (t), 22.58 (t), 14.02 (q), 13.91 (q). MS (EI): 273 (MH$^+$).

Compound 22 from Compound 13:

$^1$H NMR (300 MHz, CDCl3) δ 7.41-7.21 (m, 6H), 6.84 (s, 1H), 6.02 (dd, J=21.9, 15.8 Hz, 1H), 2.53-2.30 (m, 2H), 1.56 (s, 2H), 1.45-1.17 (m, 6H), 0.89 (t, J=5.2 Hz, 3H)

Example 10: Synthesis of (E)-4-((E)-benzylidene)-2-methyldec-2-enamide (Compound 23) (Scheme 13)

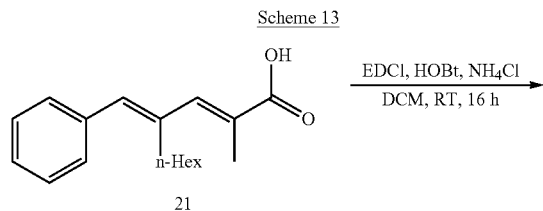

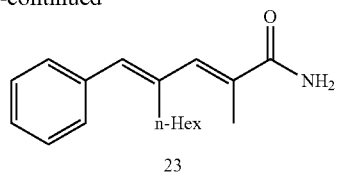

To a stirred solution of (E)-4-((E)-benzylidene)-2-methyldec-2-enoic acid 21 (150 mg, 0.53 mmol) in DCM (5 mL) were added EDCl.HCl (111 mg, 0.71 mmol), HOBt (74 mg, 0.55 mmol), NH$_4$Cl (44 mg, 0.82 mmol) and N-methylmorpholine (0.12 mL, 1.11 mmol) at 0° C. under nitrogen atmosphere. The resultant reaction mixture was stirred at RT for 16 h. The reaction was monitored by TLC; after completion of the reaction, the reaction mixture was diluted with EtOAc (20 mL) and washed with water (20 mL). Separated organic layer was dried over sodium sulfate, filtered and concentrated under reduced pressure. Obtained crude material was triturated with n-Hexane to afford Compound 23 (35 mg, 25%) as white solid.

Compound 23: $^1$H NMR (400 MHz, DMSO-d$_6$): δ 7.42-7.35 (m, 3H), 7.32-7.24 (m, 3H), 6.98 (br s, 1H), 6.80 (s, 1H), 6.44 (s, 1H), 2.35-2.29 (m, 2H), 1.96 (d, J=1.3 Hz, 3H), 1.45-1.36 (m, 2H), 1.31-1.17 (m, 6H), 0.83 (t, J=6.8 Hz, 3H); LC-MS (ESI): 99.83%; m/z 272.3 [M+H]$^+$; (column; X-select CSH C-18 (50×3.0 mm, 2.5 μm); RT 4.56 min. 2.5 mM NH$_4$OAc:ACN; 0.8 mL/min); HPLC (purity): 99.24%; (column: ZORBAX SB C-18 (150×4.6 mm, 5 μm); RT 10.81 min; ACN: 0.05% TFA; 1.0 mL/min).

Example 11: Synthesis of (E)-4-((E)-benzylidene)-N,2-dimethyldec-2-enamide (Compound 24) (Scheme 14)

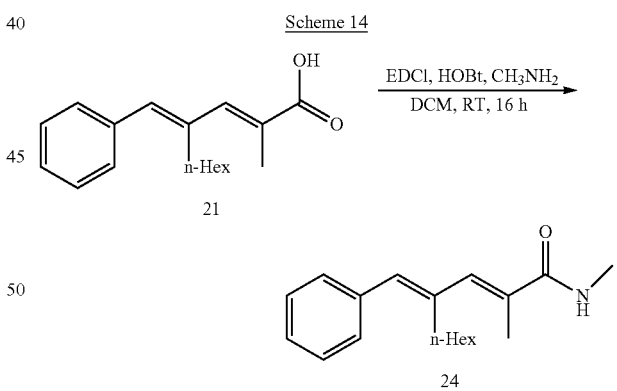

To a stirred solution of (E)-4-((Z)-benzylidene)-2-methyl-5-oxodec-2-enoic acid 21 (200 mg, 0.74 mmol) in DCM (6 mL) were added EDCl.HCl (148 mg, 0.96 mmol), HOBt (99 mg, 0.74 mmol), methylamine solution (2M in THF) (0.6 mL, 1.11 mmol) and DIPEA (0.24 mL, 1.47 mmol) at 0° C. under nitrogen atmosphere. The resultant reaction mixture was stirred at RT for 16 h. The reaction was monitored by TLC; after completion of the reaction, the reaction mixture was diluted with DCM (30 mL) and washed with water (30 mL). Separated organic layer was dried over sodium sulfate, filtered and concentrated under reduced pressure. Obtained crude material was purified through silica gel column chromatography using 20-30% EtOAc/hexanes to afford the title compound 24 (80 mg, 38%) as white solid.

Compound 24: ¹H NMR (500 MHz, DMSO-$d_6$): δ 7.84-7.81 (m, 1H), 7.39-7.33 (m, 2H), 7.29-7.22 (m, 3H), 6.72 (s, 1H), 6.41 (s, 1H), 2.65 (d, J=4.3 Hz, 3H), 2.32-2.28 (m, 2H), 1.95 (d, J=0.9 Hz, 3H), 1.42-1.34 (m, 2H), 1.28-1.15 (m, 6H), 0.81 (t, J=6.8 Hz, 3H); LC-MS (ESI): 91.80%; m/z 286.0 [M+H]$^+$; (column; X-select CSH C-18 (50×3.0 mm, 2.5 μm); RT 3.77 min. 2.5 mM NH$_4$OAc in water+5% ACN:ACN+5% 2.5 mM NH$_4$OOCH in water; 0.8 mL/min); HPLC (purity): 99.26%; (column: ZORBAX SB C-18 (150× 4.6 mm, 3.5 μm); RT 11.26 min; ACN: 0.05% TFA; 1.0 mL/min).

Example 12: Synthesis of (2E,4E)-5-(3-ethylphenyl)-N,N,4-trimethylpenta-2,4-dienamide (Compound 25) (Scheme 15)

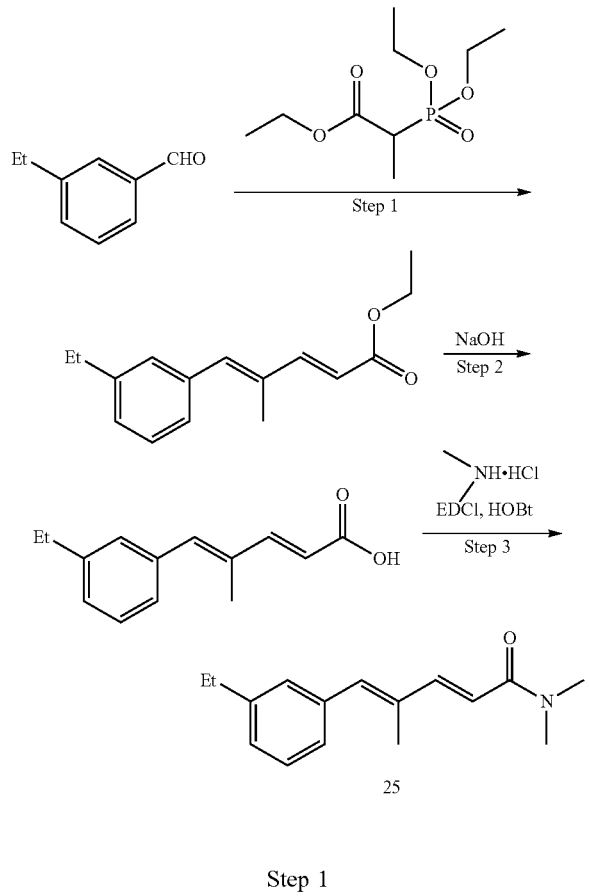

Scheme 15

Step 1

To a stirred suspension of NaH (60% dispersion in mineral oil) (101 mg, 4.20 mmol) in THF (3 mL) was added ethyl 2-(diethoxyphosphoryl)propanoate (0.47 mL, 2.23 mmol) at 0° C. under nitrogen atmosphere. The reaction mixture was stirred at room temperature for 1 h. Again the reaction mixture was cooled 0° C. and 3-ethylbenzaldehyde (0.19 mL, 1.49 mmol) in THF (2 mL) was added and the stirring was continued at room temperature for 16 h. The reaction was monitored by TLC; after completion of the reaction, the reaction mixture was quenched with water (10 mL) and extracted with EtOAc (2×20 mL). Separated organic layer was washed with saturated NaHCO$_3$, dried over sodium sulfate, filtered and concentrated under reduced pressure. Obtained crude material was purified through silica gel column chromatography using 3% EtOAc/hexanes to afford ethyl (E)-3-(3-ethylphenyl)-2-methylacrylate (250 mg, 77%) as white colour syrup.

Ethyl (E)-3-(3-ethylphenyl)-2-methylacrylate: ¹H NMR (500 MHz, CDCl$_3$): δ 7.69 (s, 1H), 7.35-7.30 (m, 1H), 7.26-7.23 (m, 2H), 7.18 (d, J=7.5 Hz, 1H), 4.29 (q, J=7.0 Hz, 2H), 2.69 (q, J=7.7 Hz, 2H), 2.14 (d, J=1.2 Hz, 3H), 1.37 (t, J=7.1 Hz, 3H), 1.27 (t, J=7.7 Hz, 3H); LC-MS (ESI): 82.65%; m/z 218.9 [M+H]$^+$ at RT 3.15 min; (column; Ascentis Express C-18 (50×3.0 mm, 2.7 μm); 0.025% Aq TFA+5% ACN:ACN+5% 0.025% Aq TFA; 1.2 mL/min).

Step 2

To a stirred solution of ethyl (2E,4E)-5-(3-ethylphenyl)-4-methylpenta-2,4-dienoate (300 mg, 1.22 mmol) in MeOH:H$_2$O (10 mL, 1:1) was added NaOH (98 mg, 2.45 mmol) at room temperature. The reaction mixture was heated to reflux for 3 h. The reaction was monitored by TLC; after completion of the reaction, methanol solvent was removed under reduced pressure. The reaction mixture was diluted with water (10 mL) and acidified with 2N HCl solution (pH-2) and extracted with EtOAc (2×20 mL). Combined organic layer was dried over sodium sulfate, filtered and concentrated under reduced pressure. Obtained crude material was purified through silica gel column chromatography using 10% EtOAc/hexanes to afford (2E,4E)-5-(3-ethylphenyl)-4-methylpenta-2,4-dienoic acid (255 mg, 96%) as light yellow syrup.

(2E,4E)-5-(3-ethylphenyl)-4-methylpenta-2,4-dienoic acid: ¹H NMR (CDCl$_3$, 500 MHz): δ 7.58 (d, J=15.6 Hz, 1H), 7.30 (t, J=8.1 Hz, 1H), 7.21-7.18 (m, 2H), 7.15 (d, J=7.5 Hz, 1H), 6.89 (s, 1H), 5.98 (d, J=15.6 Hz, 1H), 2.67 (q, J=7.5 Hz, 2H), 2.08 (s, 3H), 1.26 (t, J=7.7 Hz, 3H); LC-MS (ESI): 99.61%; m/z 215.6 [M–H]$^+$ at RT 3.24 min; (column; X-select CSH C-18 (50×3.0 mm, 2.5 μm); 2.5 mM NH$_4$OAc:ACN; 0.8 mL/min); HPLC (purity): 98.22%; (column: ZORBAX SB C-18 (150×4.6 mm, 3.5 μm); RT 10.35 min; ACN+5% 0.05% TFA: 0.05% TFA+5% ACN; 1.0 mL/min).

Step 3: Synthesis of (2E,4E)-5-(3-ethylphenyl)-N,N,4-trimethylpenta-2,4-dienamide (Compound 25)

To a stirred solution of (2E,4E)-5-(3-ethylphenyl)-4-methylpenta-2,4-dienoic acid (250 mg, 1.15 mmol) in DCM (10 mL) were added EDCl.HCl (233 mg, 1.51 mmol), HOBt (156 mg, 1.15 mmol), DIPEA (0.4 mL, 2.31 mmol) and dimethyl amine.HCl (140 mg, 1.73 mmol) at 0° C. under nitrogen atmosphere. The resultant reaction mixture was stirred at RT for 16 h. The reaction was monitored by TLC; after completion of the reaction, the reaction mixture was diluted with water (10 mL) and extracted with DCM (3×20 mL). Separated organic layer was dried over sodium sulfate, filtered and concentrated under reduced pressure. Obtained crude material was purified through silica gel column chromatography using 30% EtOAc/hexanes to afford compound 25 (130 mg, 46%) as yellow syrup.

Compound 25: ¹H NMR (400 MHz, CDCl$_3$): δ 7.48 (dd, J=15.2, 1.0 Hz, 1H), 7.31-7.28 (m, 1H), 7.19-7.15 (m, 2H), 7.11 (d, J=7.7 Hz, 1H), 6.83 (s, 1H), 6.39 (d, J=14.9 Hz, 1H), 3.14 (s, 3H), 3.06 (s, 3H), 2.66 (q, J=7.6 Hz, 2H), 2.07 (d, J=1.3 Hz, 3H), 1.25 (t, J=7.6 Hz, 3H); LC-MS (ESI): 98.90%; m/z 244.0 [M+H]$^+$ at RT 2.64 min; (column;

Ascentis Express C-18 (50×3.0 mm, 2.7 μm); 0.025% Aq TFA+5% ACN:ACN+5% 0.025% Aq TFA; 1.2 mL/min); HPLC (purity): 86.42%; (column: X SELECT CSH C-18 (150×4.6 mm, 3.5μ); RT 11.08 min; ACN: 5 mM NH₄OAc; 1.0 mL/min).

Compound 26 has been prepared from compound 9 in two steps (steps 2 and 3 of example 12)

Compound 26 ¹H NMR (300 MHz, CDCl3) δ 7.45-7.17 (m, 5H), 6.98 (s, 1H), 6.45 (s, 1H), 5.74 (s, 2H), 2.43-2.27 (m, 2H), 2.09 (d, J=1.3 Hz, 3H), 1.53-1.37 (m, 2H), 1.28 (dd, J=9.0, 5.3 Hz, 4H), 0.87 (t, J=6.8 Hz, 3H). Compound 27 has been prepared from compound 22 following the same chemical route, by performing step 3 of example 12, using NH₃ instead of NH—(CH₃)₂.

Compound 27 has been prepared from compound 22 in one single step (step 3 of example 12) following the same chemical route:

Compound 27 ¹H NMR (300 MHz, CDCl3) δ 7.46-7.17 (m, 6H), 6.78 (s, 1H), 6.03 (dd, J=23.1, 15.6 Hz, 1H), 5.52 (s, 2H), 2.53-2.31 (m, 2H), 1.55 (dd, J=10.2, 5.7 Hz, 2H), 1.44-1.20 (m, 6H), 0.89 (dd, J=8.7, 4.7 Hz, 3H)

Example 13: Synthesis of (E)-4-((E)-benzylidene)-N,N,2-trimethyldec-2-enamide (Compound 28) (Scheme 16)

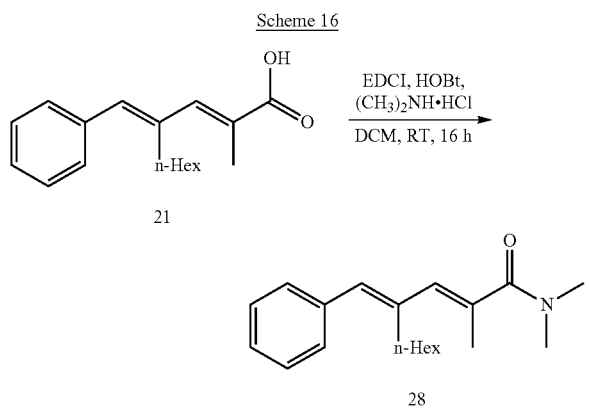

To a stirred solution of (E)-4-((E)-benzylidene)-2-methyldec-2-enoic acid (200 mg, 0.74 mmol) in DCM (6 mL) were added EDCl.HCl (148 mg, 0.96 mmol), HOBt (99 mg, 0.74 mmol), DIPEA (0.24 mL, 1.47 mmol) and dimethylamine hydrochloride (89 mg, 1.11 mmol) at 0° C. under nitrogen atmosphere. The resultant reaction mixture was stirred at RT for 16 h. The reaction was monitored by TLC; after completion of the reaction, the reaction mixture was diluted with DCM (20 mL) and washed with water (20 mL). Separated organic layer was dried over sodium sulfate, filtered and concentrated under reduced pressure. Obtained crude material was purified through silica gel column chromatography using 20-30% EtOAc/hexanes to afford Compound 28 (55 mg, 25%) as colourless liquid.

Compound 28: ¹H NMR (500 MHz, DMSO-d₆): δ 7.38-7.34 (m, 2H), 7.30-7.22 (m, 3H), 6.44 (s, 1H), 5.95 (s, 1H), 3.03-2.82 (m, 6H), 2.32-2.27 (m, 2H), 1.94 (d, J=1.4 Hz, 3H), 1.45-1.36 (m, 2H), 1.29-1.15 (m, 6H), 0.82 (t, J=6.8 Hz, 3H); LC-MS (ESI): 96.96%; m/z 300.3 [M+H]⁺; (column; X-select CSH C-18 (50×3.0 mm, 2.5 μm); RT 4.97 min. 2.5 mM NH₄OAc:ACN; 0.8 mL/min); HPLC (purity): 94.69%; (column: ZORBAX SB C-18 (150×4.6 mm, 5 μm); RT 11.74 min; ACN: 0.05% TFA; 1.0 mL/min).

Example 14: Synthesis of 5-benzylidene-3-methyl-undec-3-en-2-one (Compound 29) (Scheme 17)

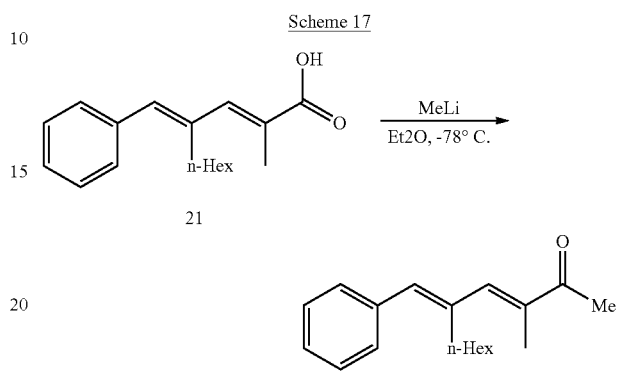

At −78° C., a solution of crude 4-benzylidene-2-methyl-dec-2-enoic acid (2.38 g, 8.74 mmol, co-evaporated twice with toluene) in diethyl ether (130 ml) was treated dropwise within 40 min. with a 1.6M solution of MeLi in Et₂O (12 ml, 19.2 mmol, 2.2 eq.) and the resulting solution was warmed to 0° C. within 30 min., stirred at that temperature for 2.5 h, cooled to −78° C., treated within 5 min. with acetone (0.83 ml), allowed to reached 0° C., poured into an aqueous saturated NH₄Cl solution (100 ml), and extracted twice with MTBE (60 ml). The combined organic phases were washed once with aq. saturated NaCl solution, dried (MgSO₄), and concentrated. The crude product (2.33 g, light yellow oil) was distilled (180° C. oven temperature, 0.06 mbar) using a ball-to-ball (Kugelrohr) distillation apparatus giving pure 5-benzylidene-3-methylundec-3-en-2-one 29 (2 g, 85%, 86:8:5 mixture of isomers) as a light yellow oil.

Compound 29: (3E,5E)-5-benzylidene-3-methylundec-3-en-2-one (major isomer): ¹H-NMR (CDCl₃, 400 MHz): δ 7.40-7.33 (m, 2H), 7.31-7.23 (m, 3H), 7.06 (br. s, 1H), 6.54 (br. s, 1H), 2.45-2.38 (m, 2H), 2.40 (s, Me), 2.01 (d, J=1.5, Me), 1.51-1.40 (m, 2H), 1.37-1.21 (m, 6H), 0.87 (t, J=6.9, Me). ¹³C-NMR (CDCl₃, 100 MHz): δ 200.32 (s), 143.24 (d), 139.08 (s), 137.37 (s), 136.95 (s), 132.27 (d), 128.79 (d, 2C), 128.31 (d, 2C), 127.13 (d), 31.57 (t), 31.46 (t), 29.21 (t), 28.90 (t), 25.84 (q), 22.56 (t), 14.01 (q), 13.22 (q). MS (EI): m/z 271 [M+H]⁺

Example 15: Synthesis of (E)-5-((E)-benzylidene) undec-3-en-2-one (Compound 30) (Scheme 18)

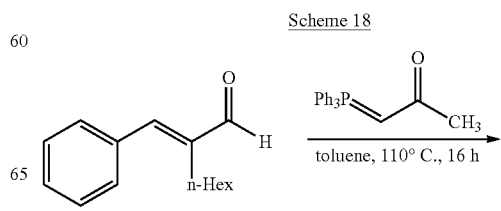

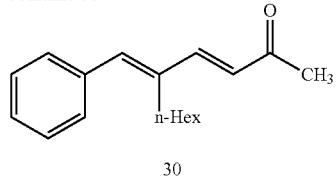

30

A solution of (E)-2-benzylideneoctanal (500 mg, 2.31 mmol) and 1-(triphenyl-λ⁵-phosphanylidene)propan-2-one (736 mg, 2.31 mmol) in toluene (10 mL) in a sealed tube under argon atmosphere was heated to 110° C. and stirred for 16 h. The reaction was monitored by TLC; after completion of the reaction, the reaction mixture was concentrated under reduced pressure. The crude material was purified through silica gel column chromatography using 10-15% EtOAc/hexanes to afford Compound 30 (200 mg, 33%) as pale yellow syrup.

Compound 30: $^1$H NMR (400 MHz, CDCl$_3$): δ 7.42-7.28 (m, 5H), 7.22 (s, 1H), 6.84 (s, 1H), 6.26 (d, J=16.1 Hz, 1H), 2.51-2.44 (m, 2H), 2.35 (s, 3H), 1.55-1.49 (m, 2H), 1.42-1.26 (m, 6H), 0.92-0.86 (m, 3H); LC-MS (ESI): 98.15%; m/z 257.1 [M+H]$^+$; (Column; Ascentis Express C-18 (50× 3.0 mm, 2.7 μm); RT 3.34 min. 0.025% Aq TFA+5% ACN:ACN+5% 0.025% Aq TFA; 1.2 mL/min); HPLC (purity): 95.26%; (column: X SELECT CSH C$_{18}$ (150×4.6 mm, 3.5μ); RT 13.91 min; 5 Mm NH$_4$OAc:ACN; 1.0 mL/min).

Example 16: Synthesis of (2E,4E)-5-(3-methoxyphenyl)-2-methylpenta-2,4-dien-1-ol (Compound 31) (Scheme 19)

Scheme 19

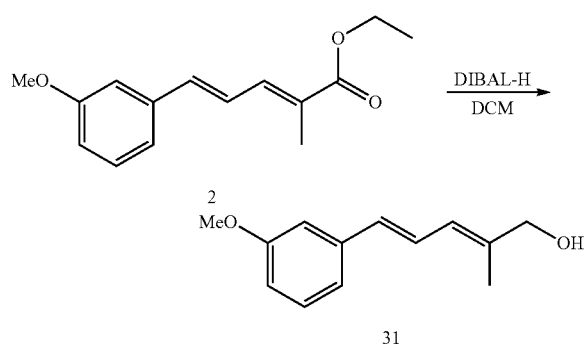

A solution of (2E,4E)-5-(3-methoxyphenyl)-2-methylpenta-2,4-dienoate 2 (compound 2) (100 mg, 0.41 mmol) in DCM (5 mL) was cooled to −78° C. and then DIBAL-H (0.6 mL, 0.61 mmol) was added drop wise under nitrogen atmosphere. The resultant reaction mixture was stirred at −78° C. for 6 h. The reaction was monitored by TLC; after completion of the reaction, the reaction mixture was quenched with 2N HCl solution (10 mL) and extracted with DCM (10 mL×2). Separated organic layer was dried over sodium sulfate, filtered and concentrated under reduced pressure. Obtained crude material was purified through silica gel column chromatography using 15% EtOAc/hexanes to afford compound 31 (42 mg, 51%) as white thick syrup.

Compound 31: $^1$H NMR (400 MHz, DMSO-d$_6$): δ 7.25-7.18 (m, 1H), 7.16-7.01 (m, 3H), 6.79-6.75 (m, 1H), 6.48 (d, J=15.5 Hz, 1H), 6.18 (br d, J=11.1 Hz, 1H), 4.85 (t, J=5.7 Hz, 1H), 3.90 (d, J=5.5 Hz, 2H), 3.76 (s, 3H), 1.80 (s, 3H); LC-MS (ESI): 99.19%; m/z 187.0 [M−OH+H]$^+$ at RT 2.37 min; (column; Ascentis Express C-18 (50×3.0 mm, 2.7 μm); 0.025% Aq TFA+5% ACN:ACN+5% 0.025% Aq TFA; 1.2 mL/min); HPLC (purity): 88.12%; (column: XSELECT CSH C-18 (150×4.6 mm, 3.5 μm); RT 9.22 min; ACN:0.5% TFA); 1.0 mL/min).

Example 17: Synthesis of (2E,4E)-5-(2-propylphenyl)penta-2,4-dien-1-ol (Compound 32) (Scheme 20)

Scheme 20

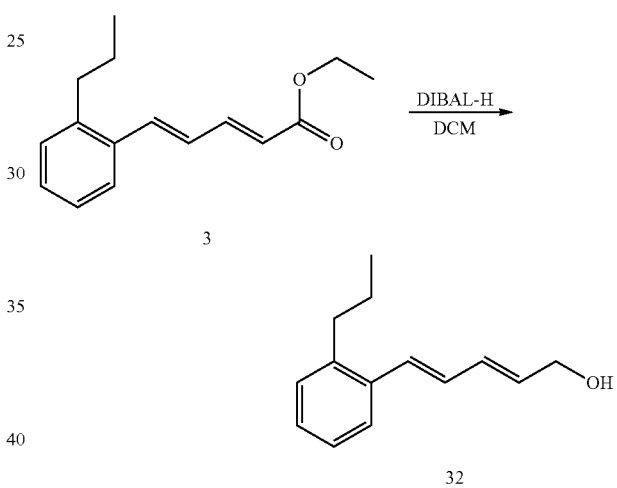

A solution of ethyl (2E,4E)-5-(2-propylphenyl)penta-2,4-dienoate (Compound 3) (100 mg, 0.41 mmol) in DCM (20 mL) was cooled to −78° C. and then DIBAL-H (0.6 mL, 0.61 mmol) was added under nitrogen atmosphere. The resultant reaction mixture was stirred at −78° C. for 5 h. The reaction was monitored by TLC; after completion of the reaction, the reaction mixture was quenched with sodium potassium tartrate solution (10 mL) and extracted with DCM (10 mL×2). Separated organic layer was dried over sodium sulfate, filtered and concentrated under reduced pressure. Obtained crude material was purified through silica gel column chromatography using 15% EtOAc/hexanes to afford compound 32 (21 mg, 25%) as colourless syrup.

Compound 32: $^1$H NMR (400 MHz, DMSO-d$_6$): δ 7.57-7.51 (m, 1H), 7.21-7.13 (m, 3H), 6.79 (d, J=5.4 Hz, 2H), 6.48-6.39 (m, 1H), 5.95 (dt, J=15.2, 5.3 Hz, 1H), 4.78 (t, J=5.5 Hz, 1H), 4.05 (td, J=1.6, 5.4 Hz, 2H), 2.66-2.60 (m, 2H), 1.54-1.46 (m, 2H), 0.91 (t, J=7.4 Hz, 3H); LC-MS (ESI): 95.27%; m/z 184.9 [M−H$_2$O+H]$^+$ at RT 2.71 min; (column; Ascentis Express C-18 (50×3.0 mm, 2.7 μm); 0.025% Aq TFA+5% ACN:ACN+5% 0.025% Aq TFA; 1.2 mL/min); HPLC (purity): 87.46%; (column: XSELECT CSH C-18 (150×4.6 mm, 3.5 μm); RT 10.58 min; ACN: 0.5% TFA); 1.0 mL/min).

Example 18: Synthesis of (E)-4-((E)-4-fluorobenzylidene)-2-methyldec-2-en-1-ol (Compound 33) to Compound 35 (Scheme 21)

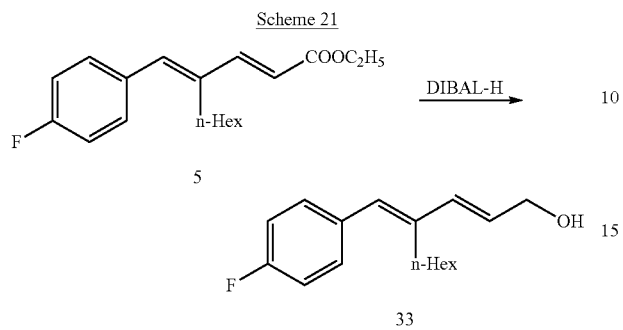

A solution of ethyl (E)-4-((E)-4-fluorobenzylidene)-2-methyldec-2-enoate 5 (500 mg, 1.57 mmol) in DCM (10 mL) was cooled to −78° C. and then DIBAL-H (2.36 mL, 2.35 mmol) was added drop wise under nitrogen atmosphere. The resultant reaction mixture was stirred at −78° C. for 6 h. The reaction was monitored by TLC; after completion of the reaction, the reaction mixture was quenched with 2N HCl solution (10 mL), stirred for 30 minutes and then extracted with DCM (3×10 mL). Separated organic layer was dried over sodium sulfate, filtered and concentrated under reduced pressure. Obtained crude material was purified through silica gel column chromatography using 10% EtOAc/hexanes to afford (E)-4-((E)-4-fluorobenzylidene)-2-methyldec-2-en-1-ol 33 (230 mg, 53%) as colourless syrup.

Compound 33: $^1$H NMR (400 MHz, CDCl$_3$): δ 7.25-7.19 (m, 2H), 7.06-7.00 (m, 2H), 6.43 (s, 1H), 6.31 (dd, J=15.8, 0.7 Hz, 1H), 5.94 (dt, J=15.6, 6.0 Hz, 1H), 4.31-4.24 (m, 2H), 2.43-2.35 (m, 2H), 1.54-1.47 (m, 2H), 1.40-1.24 (m, 7H), 0.92-0.85 (m, 3H); LC-MS (ESI): 99.19%; m/z 244.9 [M−OH+H]$^+$ at RT 3.11 min; (column; Ascentis Express C-18 (50×3.0 mm, 2.7 µm); 0.025% Aq TFA+5% ACN: ACN+5% 0.025% Aq TFA; 1.2 mL/min); HPLC (purity): 99.38%; (column: XSELECT CSH C-18 (150×4.6 mm, 3.5 µm); RT 12.94 min; ACN+5% 0.5% TFA:0.5% TFA+5% ACN); 1.0 mL/min).

Compound 34 has been prepared from compound 9 following the same chemical route as described in example 18.

Compound 34: $^1$H NMR (300 MHz, CDCl3) δ 7.51-7.07 (m, 5H), 6.35 (s, 1H), 6.00 (s, 1H), 4.13 (s, 2H), 2.35-2.21 (m, 2H), 1.88 (d, J=1.3 Hz, 3H), 1.66-1.15 (m, 6H), 0.87 (t, J=6.8 Hz, 3H).

Compound 35 has been prepared using the same chemical route described in example 18 (Scheme 22):

Scheme 22

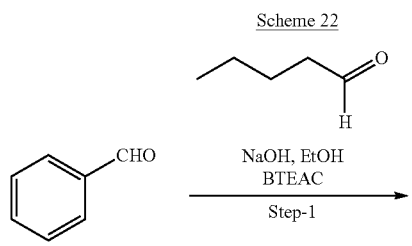

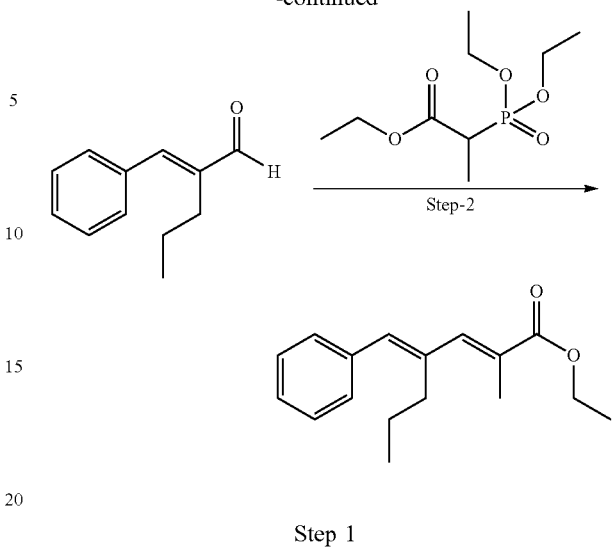

Step 1

Pentanal (2 g, 23.2 mmol) was dissolved in EtOH (20 mL) and NaOH (1.4 g, 34.8 mmol) was added at 0° C. After stirring for 10 minutes, benzaldehyde (2.46 mL, 27.8 mmol) followed by BTEAC (2.6 g, 11.4 mmol) were added. The resultant reaction mixture was stirred at room temperature for 16 h. The reaction was monitored by TLC. After completion of the reaction, volatiles were removed under reduced pressure. Crude material was diluted with water (30 mL) and extracted with DCM (2×50 mL). Organic layer was dried over sodium sulfate and concentrated under reduced pressure. Obtained crude material was purified through silica gel column chromatography using 5% EtOAc/hexanes to afford (E)-2-benzylidenepentanal (1.7 g, 42%) as syrup.

LC-MS (ESI): 79.18%; m/z 175.3 [M+H]$^+$ at RT 4.58 min; (column; X Select CSH C-18 (50×3.0 mm, 2.5 µm); 2.5 mM Aq.NH$_4$OAc:ACN; 0.8 mL/min).

Step 2: Synthesis of ethyl (E)-4-((E)-benzylidene)-2-methylhept-2-enoate

NaH (60% dispersion in mineral oil) (664 mg, 27.6 mmol) was dissolved in THF (30 mL) and ethyl 2-(diethoxyphosphoryl)propanoate (3.14 mL, 14.6 mmol) was added to the mixture at 0° C. under nitrogen atmosphere. After stirring for 1 h at room temperature, (E)-2-benzylidenepentanal (1.7 g, 9.77 mmol) was added at 0° C. and stirring was continued for 16 h at room temperature. The reaction was monitored by TLC. After completion of the reaction, the reaction mixture was quenched with water and extracted with EtOAc (2×30 mL). Separated organic layer was washed with saturated NaHCO$_3$, dried over sodium sulfate, filtered and concentrated under reduced pressure. Obtained crude material was purified through silica gel column chromatography using 5% EtOAc/hexanes to afford title compound (1.9 g, 76%) as colourless syrup.

$^1$H NMR (400 MHz, CDCl$_3$): δ 7.39-7.28 (s, 5H), 7.22 (s, 1H), 6.51 (s, 1H), 4.25 (d, J=7.2 Hz, 2H), 2.36 (d, J=8.0 Hz, 2H), 2.07 (d, J=1.5 Hz, 3H), 1.52-1.43 (m, 2H), 1.33 (t, J=7.2 Hz, 3H), 0.92 (t, J=7.5 Hz, 3H).

Further reduction of the so obtained ethyl ester using Example 18 protocol afforded compound 35

Compound 35: $^1$H NMR (300 MHz, CDCl3) δ 7.40-7.16 (m, 5H), 6.36 (s, 1H), 6.00 (s, 1H), 4.14 (s, 2H), 2.28 (dd, J=9.1, 6.7 Hz, 2H), 1.89 (d, J=1.2 Hz, 3H), 1.66-1.37 (m, 2H), 0.92 (dd, J=9.8, 4.9 Hz, 3H).

Example 19: Synthesis of (2E,4E)-5-(3-methoxyphenyl)-2-methylpenta-2,4-dienal (Compound 36) (Scheme 23)

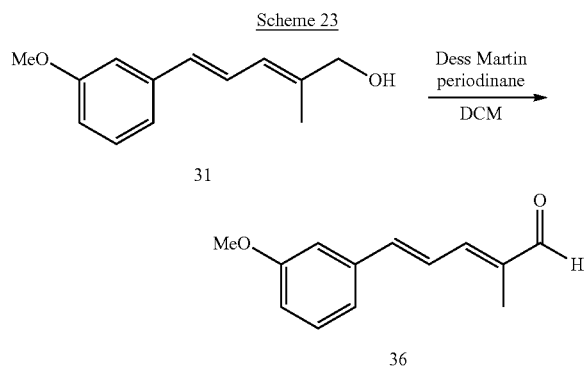

A solution of compound 31 (50 mg, 0.24 mmol) in DCM (5 mL) was cooled to 0° C. and then Dess-Martin Periodinane (155 mg, 0.736 mmol) was added under nitrogen atmosphere. The resultant reaction mixture was stirred at RT for 2 h. The reaction was monitored by TLC; after completion of the reaction, the reaction mixture was quenched with saturated NaHCO$_3$ solution (10 mL) and extracted with DCM (10 mL×2). Separated organic layer was dried over sodium sulfate, filtered and concentrated under reduced pressure. Obtained crude material was purified through silica gel column chromatography using 10% EtOAc/hexanes to afford compound 36 (38 mg, 77%) as light yellow syrup.

Compound 36: $^1$H NMR (400 MHz, DMSO-d$_6$): δ 9.49 (s, 1H), 7.50-7.41 (m, 1H), 7.35-7.19 (m, 4H), 7.13 (d, J=15.5 Hz, 1H), 6.96-6.91 (m, 1H), 3.81 (s, 3H), 1.89 (d, J=0.9 Hz, 3H); LC-MS: 93.69%; m/z 203.2[M+H]$^+$ at RT 4.01 min; (column; X-select CSH C-18 (50×3.0 mm, 2.5 μm); 2.5 mM NH$_4$OAc:ACN; 0.8 mL/min); HPLC (purity): 93.90%; (column: ZORBAX SB C-18 (150×4.6 mm, 3.5 μm); RT 10.18 min; ACN: 0.05% TFA; 1.0 mL/min).

Example 20: Synthesis of (2E,4E)-5-(2-propylphenyl)penta-2,4-dienal (Compound 37) (Scheme 24)

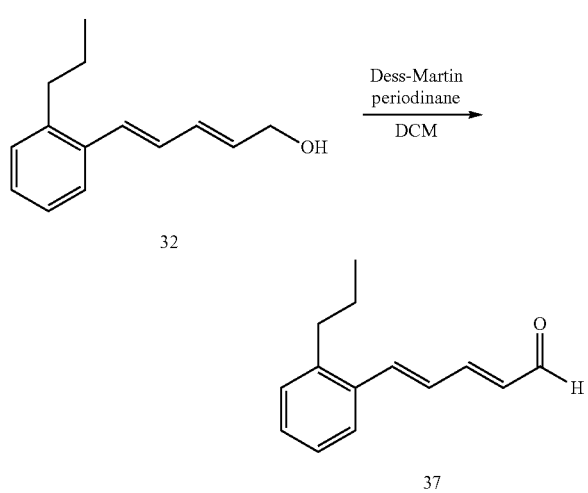

A solution of compound 32 (60 mg, 0.29 mmol) in DCM (20 mL) was cooled to 0° C. and then Dess-Martin Periodinane (189 mg, 0.44 mmol) was added under nitrogen atmosphere. The resultant reaction mixture was stirred at RT for 16 h. The reaction was monitored by TLC; after completion of the reaction, the reaction mixture was quenched with saturated NaHCO$_3$ solution (10 mL) and extracted with DCM (20 mL×2). Separated organic layer was dried over sodium sulfate, filtered and concentrated under reduced pressure. Obtained crude material was purified through silica gel column chromatography using 10% EtOAc/hexanes to afford the compound (25 mg, 42%) as a thick syrup.

Compound 37: $^1$H NMR (500 MHz, CDCl$_3$): δ 9.63 (d, J=7.5 Hz, 1H), 7.60 (d, J=7.5 Hz, 1H), 7.33-7.27 (m, 3H), 7.24-7.18 (m, 2H), 6.97-6.91 (m, 1H), 6.27 (dd, J=15.0, 7.5 Hz, 1H), 2.70 (t, J=7.5 Hz, 2H), 1.63-1.57 (m, 2H), 0.98 (t, J=7.5 Hz, 3H); LC-MS: 99.90%; m/z 201.3[M+H]$^+$ at RT 4.45 min; (column; X-select CSH C-18 (50×3.0 mm, 2.5 μm); 2.5 mM NH$_4$OAc:ACN; 0.8 mL/min); HPLC (purity): 97.07%; (column: ZORBAX SB C-18 (150×4.6 mm, 3.5 μm); RT 11.44 min; ACN: 0.05% TFA; 1.0 mL/min).

Example 21: Synthesis of (E)-4-((E)-4-fluorobenzylidene)dec-2-enal (Compound 38) (Scheme 25)

Scheme 25

To a stirred solution of (E)-4-((E)-4-fluorobenzylidene)dec-2-en-1-ol (compound 33) (80 mg, 0.31 mmol) in DCM (5 mL) was added Dess-Martin Periodinane (194 mg, 0.45 mmol) at 0° C. under nitrogen atmosphere. The resultant reaction mixture was stirred at RT for 3 h. The reaction was monitored by TLC; after completion of the reaction, the reaction mixture was quenched with saturated NaHCO$_3$ solution (10 mL) and extracted with DCM (20 mL×2). Separated organic layer was washed with saturated NaHCO$_3$ solution (10 mL), dried over sodium sulfate, filtered and concentrated under reduced pressure. Obtained crude material was purified through silica gel column chromatography using 5% EtOAc/hexanes to afford compound 38 (55 mg, 69%) as yellow syrup.

Compound 38: $^1$H NMR (500 MHz, CDCl$_3$): δ 9.64 (d, J=7.8 Hz, 1H), 7.34 (dd, J=8.7, 5.5 Hz, 2H), 7.19 (d, J=15.6 Hz, 1H), 7.10 (t, J=8.7 Hz, 2H), 6.85 (s, 1H), 6.29 (dd, J=15.6, 7.8 Hz, 1H), 2.51-2.44 (m, 2H), 1.53-1.49 (m, 2H), 1.42-1.35 (m, 2H), 1.33-1.25 (m, 4H), 0.89 (t, J=6.9 Hz, 3H); LC-MS: 99.57%; m/z 261.3[M+H]$^+$ at RT 5.05 min; (column; X-select CSH C-18 (50×3.0 mm, 2.5 μm); 2.5 mM Aq NH$_4$OAc:ACN; 0.8 mL/min); HPLC (purity): 94.74%;

(column: ZORBAX SB C-18 (150×4.6 mm, 3.5 μm); RT 14.06 min; ACN+0.05% TFA: 0.05% TFA+ACN; 1.0 mL/min).

Compounds 40 and 41 have been prepared from compound 34 and from compound 35, respectively, following the chemical route described in example 21.

Compound 40: $^1$H NMR (300 MHz, CDCl3) δ 9.50 (s, 1H), 7.45-7.27 (m, 5H), 6.86 (d, J=1.1 Hz, 1H), 6.73 (s, 1H), 2.50 (dd, J=9.2, 6.8 Hz, 2H), 2.00 (d, J=1.3 Hz, 3H), 1.61-1.23 (m, 6H), 0.88 (t, J=7.0 Hz, 3H)

Compound 41: $^1$H NMR (300 MHz, CDCl3) δ 9.50 (s, 1H), 7.45-7.20 (m, 5H), 6.88-6.82 (m, 1H), 6.74 (s, 1H), 2.54-2.42 (m, 2H), 2.00 (d, J=1.3 Hz, 3H), 1.66-1.41 (m, 2H), 0.95 (t, J=7.3 Hz, 3H)

Example 22: Synthesis of (E)-4-((E)-benzylidene)dec-2-en-1-ol (Compound 45) and (E)-4-((E)-benzylidene)dec-2-enal (Compound 39) (Scheme 26)

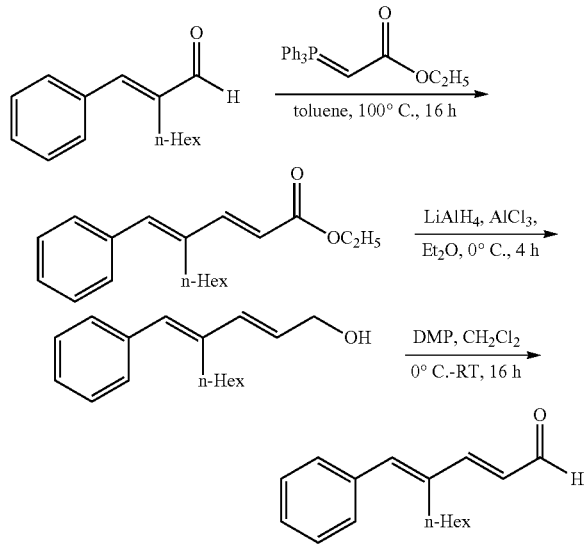

Step 1

A solution of (E)-2-benzylideneoctanal (1 g, 4.63 mmol) and ethyl 2-(triphenyl-λ$^5$-phosphanylidene)acetate (3.22 g, 9.26 mmol) in toluene (10 mL) in a sealed tube under argon atmosphere was heated to 100° C. and stirred for 16 h. The reaction was monitored by TLC; after completion of the reaction, the reaction mixture was concentrated under reduced pressure to obtain the crude. The crude material was purified through silica gel column chromatography using 10% EtOAc/hexanes to afford ethyl (E)-4-((E)-benzylidene)dec-2-enoate (1 g, 77%) as colourless syrup.

Ethyl (E)-4-((E)-benzylidene)dec-2-enoate: $^1$H NMR (400 MHz, CDCl$_3$): δ 7.44-7.25 (m, 6H), 6.80 (s, 1H), 5.98 (d, J=15.8 Hz, 1H), 4.25 (q, J=7.1 Hz, 2H), 2.50-2.42 (m, 2H), 1.56-1.48 (m, 2H), 1.41-1.24 (m, 9H), 0.92-0.85 (m, 3H); LC-MS (ESI): 85.22%; m/z 287.1 [M+H]$^+$; (column; Kinetex EVO C-18 (50×3.0 mm, 2.6 μm); RT 4.73 min. 2.5 mM NH$_4$OAC in water+5% ACN:ACN+5% 2.5 mM NH$_4$OOCH in water; 0.8 mL/min).

Step 2: Synthesis of (E)-4-((E)-benzylidene)dec-2-en-1-ol

To a stirred solution of lithium aluminium hydride (66 mg, 1.74 mmol) in diethylether (7 mL) was added aluminium chloride (233 mg, 1.74 mmol) at 0° C. under argon atmosphere. The mixture was stirred for 15 min. Ethyl (E)-4-((E)-benzylidene)dec-2-enoate (500 mg, 1.74 mmol) in diethylether (3 mL) was then added drop wise at 0° C. and the reaction mixture was stirred at the same temperature for 4 h. The reaction was monitored by TLC; after completion of the reaction, the reaction mixture was quenched with 2 N HCl (10 mL), stirred for 30 min and extracted with CH$_2$Cl$_2$ (2×20 mL). The organic layer was separated, dried over sodium sulfate, filtered and concentrated under reduced pressure. The crude material was purified through silica gel column chromatography using 20% EtOAc/hexanes to afford title compound (210 mg, 49%) as colourless syrup.

(E)-4-((E)-benzylidene)dec-2-en-1-ol: $^1$H NMR (400 MHz, CDCl$_3$): δ 7.37-7.32 (m, 2H), 7.29-7.27 (m, 2H), 7.25-7.20 (m, 1H), 6.48 (s, 1H), 6.33 (dd, J=15.7, 0.8 Hz, 1H), 5.98-5.915 (m, 1H), 4.28 (t, J=5.3 Hz, 2H), 2.46-2.40 (m, 2H), 1.60-1.55 (m, 1H), 1.54-1.50 (m, 1H), 1.41-1.32 (m, 3H), 1.32-1.24 (m, 4H), 0.91-0.86 (m, 3H); LC-MS (ESI): 97.08%; m/z 227.1 [M–H$_2$O]$^+$; (column; Kinetex EVO C-18 (50×3.0 mm, 2.6 μm); RT 3.91 min. 2.5 mM NH$_4$OOCH in water+5% ACN:ACN+5% 2.5 mM NH$_4$OOCH in water; 0.8 mL/min); HPLC (purity): 92.14%; (column: X SELECT CSH C18 (150×4.6 mm, 3.5μ); RT 12.98 min; 5 Mm NH$_4$OAc:ACN; 1.0 mL/min).

Step 3: Synthesis of (E)-4-((E)-benzylidene)dec-2-enal (Compound 39)

To a stirred solution of Compound 45 (50 mg, 0.2 mmol) in CH$_2$Cl$_2$ (5 mL) was added Dess-Martin periodinane (130 mg, 0.31 mmol) at 0° C. under argon atmosphere. The reaction mixture was gradually warmed to RT and stirred for 16 h. The reaction was monitored by TLC; after completion of the reaction, the reaction mixture was quenched with saturated NaHCO$_3$ solution (5 mL) and extracted with CH$_2$Cl$_2$ (2×10 mL). The organic layer was separated, dried over sodium sulfate, filtered and concentrated under reduced pressure. The crude material was purified through silica gel column chromatography using 10% EtOAc/hexanes to afford the compound (35 mg, 71%) as pale yellow syrup.

Compound 39: $^1$H NMR (500 MHz, CDCl$_3$): δ 9.64 (d, J=7.8 Hz, 1H), 7.43-7.31 (m, 5H), 7.21 (d, J=15.6 Hz, 1H), 6.90 (s, 1H), 6.29 (dd, J=7.8, 15.6 Hz, 1H), 2.53-2.48 (m, 2H), 1.59-1.51 (m, 4H), 1.42-1.35 (m, 2H), 1.33-1.27 (m, 4H), 0.89 (br t, J=6.8 Hz, 3H); LC-MS (ESI): 87.11%; m/z 243.1 [M+H]$^+$; (column; Kinetex EVO C-18 (50×3.0 mm, 2.6 μm); RT 4.23 min. 2.5 mM NH$_4$OOCH in water+5% ACN:ACN+5% 2.5 mM NH$_4$OOCH in water; 0.8 mL/min).

Example 23: Synthesis of ((E)-2-((E)-3-methoxy-2-methylprop-1-en-1-yl)oct-1-en-1-yl)benzene (Compound 42) (Scheme 27)

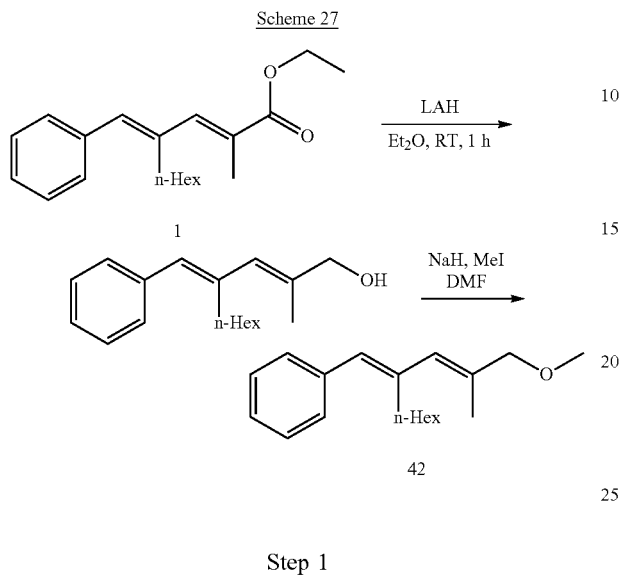

Step 1

To a stirred solution of ethyl (E)-4-((E)-benzylidene)-2-methyldec-2-enoate (compound 1) (100 mg, 0.33 mmol) in Et$_2$O (3 mL) was added LAH (24 mg, 0.66 mmol) at 0° C. under nitrogen atmosphere. The resultant reaction mixture was stirred at RT for 1 h. The reaction was monitored by TLC; after completion of the reaction, the reaction mixture was diluted with EtOAc (20 mL), stirred for 30 minutes at RT and then washed with water (20 mL). Separated organic layer was dried over sodium sulfate, filtered and concentrated under reduced pressure. Obtained crude material was purified through silica gel column chromatography using 10% EtOAc/hexanes to afford (E)-4-((E)-benzylidene)-2-methyldec-2-en-1-ol (40 mg, 47%) as colourless liquid.

(E)-4-((E)-benzylidene)-2-methyldec-2-en-1-ol: $^1$H NMR (400 MHz, DMSO-d$_6$): δ 7.38-7.32 (m, 2H), 7.28-7.19 (m, 3H), 6.30 (s, 1H), 5.95 (s, 1H), 4.84-4.78 (m, 1H), 3.91 (d, J=5.4 Hz, 2H), 1.77 (s, 3H), 1.45-1.37 (m, 2H), 1.32-1.16 (m, 6H), 0.83 (t, J=6.9 Hz, 3H); LC-MS (ESI): 94.50%; m/z 241.3[M-18+H]$^+$ at RT 5.14 min and 5.49%; m/z 241.3[M-18+H]$^+$ at RT 5.30 min; (column; X-select CSH C-18 (50×3.0 mm, 2.5 µm); 2.5 mM NH$_4$OAc:ACN; 0.8 mL/min); HPLC (purity): 87.17%; (column: ZORBAX SB C-18 (150×4.6 mm, 3.5 µm); RT 11.99 min; ACN: 0.05% TFA; 1.0 mL/min).

Step 2: Synthesis of ((E)-2-((E)-3-methoxy-2-methylprop-1-en-1-yl)oct-1-en-1-yl)benzene (Compound 42)

To a suspension of NaH (60% dispersion in mineral oil) (34 mg, 1.41 mmol) in DMF (5 mL) was added (E)-4-((E)-benzylidene)-2-methyldec-2-en-1-ol from step 1 (150 mg, 0.58 mmol) at 0° C. under nitrogen atmosphere. The reaction mixture was stirred for 1 h. Methyl iodide (0.07 mL, 1.16 mmol) was then added and the stirring was continued for 1 h. The reaction was monitored by TLC; after completion of the reaction, the reaction mixture was quenched with ice cold water (10 mL) and extracted with ether (2×20 mL). Separated organic layer was washed with water (20 mL), dried over sodium sulfate, filtered and concentrated under reduced pressure. Obtained crude material was purified through silica gel column chromatography using 10% EtOAc/hexanes to afford compound 42 (125 mg, 79%) as colourless syrup.

Compound 42: $^1$H NMR (500 MHz, DMSO-d$_6$): δ 7.37-7.32 (m, 2H), 7.26-7.19 (m, 3H), 6.32 (s, 1H), 5.94 (s, 1H), 3.84 (s, 2H), 3.22 (s, 3H), 2.25 (t, J=8.1 Hz, 2H), 2.87 (s, 2H), 1.43-1.35 (m, 2H), 1.27-1.16 (m, 7H), 0.81 (t, J=6.9 Hz, 3H); LC-MS (ESI): 93.79%; m/z 241.1 [M−OCH$_3$]$^+$ at RT 4.10 min and 4.13%; m/z 241.1[M−OCH$_3$]$^+$ at RT 4.21 min; (column; Ascentis Express C-18 (50×3.0 mm, 2.7 µm); 0.025% Aq TFA+5% ACN:ACN+5% 0.025% Aq TFA; 1.2 mL/min); HPLC (purity): 84.26%+10.13%; (column: ZORBAX SB C-18 (150×4.6 mm, 3.5 µm); RT 20.95 & 22.14 min; ACN: 0.05% TFA; 1.0 mL/min).

Example 24: Synthesis of ((E)-2-((E)-3-ethoxy-2-methyl prop-1-en-1-yl)oct-1-en-1-yl)benzene (Compound 43) (Scheme 28)

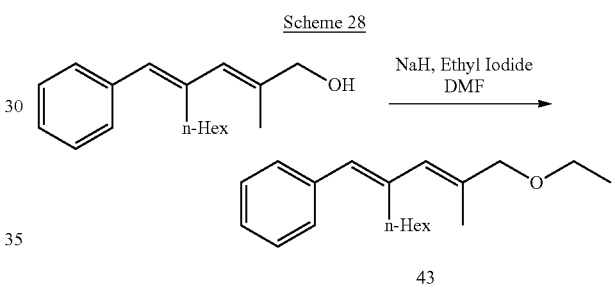

To a suspension of NaH (60% dispersion in mineral oil) (34 mg, 1.41 mmol) in DMF (5 mL) was added (E)-4-((E)-benzylidene)-2-methyldec-2-en-1-ol (CC-014) (150 mg, 0.58 mmol) at 0° C. under nitrogen atmosphere. The reaction mixture was stirred for 1 h, and ethyl iodide (0.09 mL, 1.16 mmol) was then added and the stirring was continued for 1 h. The reaction was monitored by TLC; after completion of the reaction, the reaction mixture was quenched with ice cold water (10 mL) and extracted with ether (2×20 mL). Separated organic layer was washed with water (20 mL), dried over sodium sulfate, filtered and concentrated under reduced pressure. Obtained crude material was purified through silica gel column chromatography using 10% EtOAc/hexanes to afford Compound 43 (125 mg, 75%) as colourless syrup.

Compound 43: $^1$H NMR (500 MHz, DMSO-d$_6$): δ 7.38-7.32 (m, 2H), 7.28-7.20 (m, 3H), 6.32 (s, 1H), 5.95 (s, 1H), 3.89 (s, 2H), 3.41 (q, J=7.1 Hz, 2H), 2.26 (t, J=7.5 Hz, 2H), 1.79 (s, 3H), 1.44-1.36 (m, 2H), 1.28-1.18 (m, 6H), 1.14 (t, J=6.9 Hz, 3H), 0.82 (t, J=6.9 Hz, 3H); LC-MS (ESI): 92.58%; m/z 240.9 [M-OEt]$^+$ at RT 4.34 min and 4.38%; m/z 240.0[M-OEt]$^+$ at RT 4.43 min; (column; Ascentis Express C-18 (50×3.0 mm, 2.7 µm); 0.025% Aq TFA+5% ACN:ACN+5% 0.025% Aq TFA; 1.2 mL/min); HPLC (purity): 82.70%+9.94%; (column: ZORBAX SB C-18 (150× 4.6 mm, 3.5 µm); RT 24.78 & 26.41 min; ACN+5% 0.05% TFA: 0.05% TFA+5% ACN; 1.0 mL/min).

Example 25: Synthesis of 1-((E)-2-((E)-3-ethoxy-2-methylprop-1-en-1-yl)oct-1-en-1-yl)-4-fluorobenzene (Compound 44) (Scheme 29)

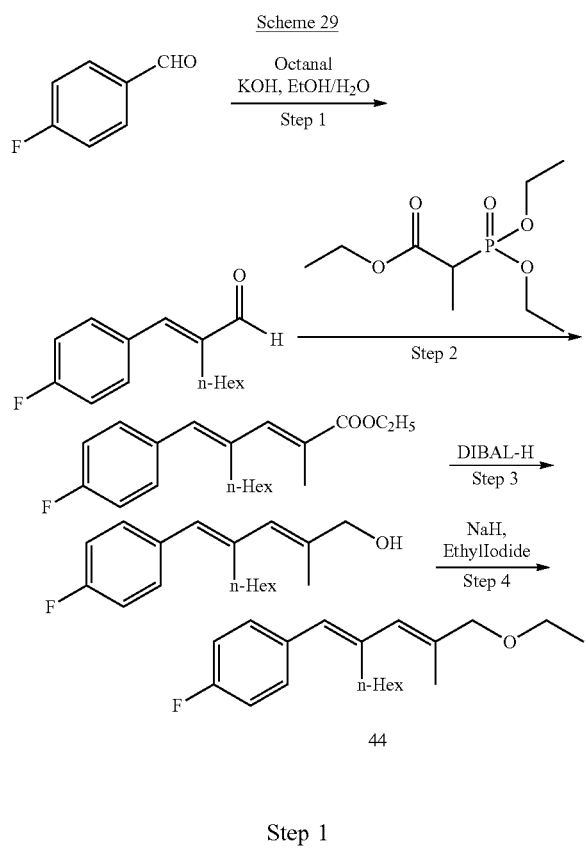

Scheme 29

Step 1

To a solution of octanal (3.5 mL, 23.4 mmol) in EtOH:H$_2$O (40 mL, 1:1) were added KOH (1.31 g, 23.4 mmol) and 4-fluorobenzaldehyde (2 g, 15.6 mmol) at 0° C. The reaction mixture was stirred for 16 h. The reaction was monitored by TLC; after completion of the reaction, ethanol was removed. Crude material was diluted with water (30 mL) and extracted with DCM (3×30 mL). Separated organic layer was dried over sodium sulfate, filtered and concentrated under reduced pressure. Obtained crude material was purified through silica gel column chromatography using 3% EtOAc/hexanes to afford crude (E)-2-(4-fluorobenzylidene)octanal (1.3 g) as yellow syrup, which was taken to next step without any further purification.

Step 2

Ethyl 2-(diethoxyphosphoryl)propanoate (1.8 mL, 8.33 mmol) was added drop wise at 0° C. under nitrogen atmosphere to a stirred suspension of NaH (60% dispersion in mineral oil) (377 mg, 15.7 mmol) in THF (10 mL). After completion of the addition, the reaction mixture was stirred at RT for 1 h. Again, the mixture was cooled to 0° C. and (E)-2-(4-fluorobenzylidene)octanal (1.3 g, 5.55 mmol) in THF (10 mL) was slowly added and the stirring was continued at RT for 5 h. The reaction was monitored by TLC; after completion of the reaction, the reaction mixture was quenched water (20 mL) and extracted with EtOAc (3×20 mL). Separated organic layer was dried over sodium sulfate, filtered and concentrated under reduced pressure. Obtained crude material was purified through silica gel column chromatography using 3% EtOAc/hexane to afford ethyl (E)-4-((E)-4-fluorobenzylidene)-2-methyldec-2-enoate (1.1 g, 62%) as light yellow syrup.

Ethyl (E)-4-((E)-4-fluorobenzylidene)-2-methyldec-2-enoate: $^1$H NMR (500 MHz, CDCl$_3$) δ 7.26-7.19 (m, 3H), 7.12-7.00 (m, 2H), 6.45 (s, 1H), 4.25 (q, J=6.9 Hz, 2H), 2.38-2.32 (m, 2H), 2.06 (s, 3H), 1.38-1.31 (m, 3H), 1.30-1.18 (m, 8H), 0.93-0.83 (m, 3H); LC-MS (ESI): 79.24%; m/z 318.9 [M+H]$^+$ at RT 3.70 min; (column; Ascentis Express C-18 (50×3.0 mm, 2.7 µm); 0.025% Aq TFA+5% ACN:ACN+5% 0.025% Aq TFA; 1.2 mL/min).

Step 3

A solution of ethyl (E)-4-((E)-4-fluorobenzylidene)-2-methyldec-2-enoate (500 mg, 1.57 mmol) in DCM (10 mL) was cooled to −78° C. and then DIBAL-H (2.36 mL, 2.35 mmol) was added drop wise under nitrogen atmosphere. The resultant reaction mixture was stirred at −78° C. for 6 h. The reaction was monitored by TLC; after completion of the reaction, the reaction mixture was quenched with 2N HCl solution (10 mL), stirred for 30 minutes and then extracted with DCM (3×10 mL). Separated organic layer was dried over sodium sulfate, filtered and concentrated under reduced pressure. Obtained crude material was purified through silica gel column chromatography using 10% EtOAc/hexanes to afford (E)-4-((E)-4-fluorobenzylidene)-2-methyldec-2-en-1-ol (230 mg, 53%) as colourless syrup.

(E)-4-((E)-4-fluorobenzylidene)-2-methyldec-2-en-1-ol: $^1$H NMR (500 MHz, CDCl$_3$) δ 7.20 (dd, J=8.4, 5.8 Hz, 2H), 7.06-6.99 (m, 2H), 6.30 (s, 1H), 5.98 (s, 1H), 4.13 (s, 2H), 2.28-2.23 (m, 2H), 1.87 (s, 3H), 1.47-1.38 (m, 3H), 1.33-1.21 (m, 5H), 0.87 (t, J=6.9 Hz, 3H); HPLC (purity): 86.31%; (column: XSELECT CSH C-18 (150×4.6 mm, 3.5 µm); RT 13.38 min; ACN: 5 mM NH$_4$OAc; 1.0 mL/min).

Step 4: Synthesis of 1-((E)-2-((E)-3-ethoxy-2-methylprop-1-en-1-yl)oct-1-en-1-yl)-4-fluorobenzene (Compound 44)

(E)-4-((E)-4-fluorobenzylidene)-2-methyldec-2-en-1-ol from step 3 (180 mg, 0.65 mmol) in THF (5 mL) was added to a stirred suspension of NaH (60% dispersion in mineral oil) (50 mg, 2.10 mmol) in THF (5 mL), at 0° C. under nitrogen atmosphere. After stirring for 15 minutes, ethyl iodide (0.11 mL, 1.30 mmol) was added and the stirring was continued at room temperature for 16 h. The reaction was monitored by TLC; after completion of the reaction, the reaction mixture was quenched with ice water (10 mL) and extracted with EtOAc (2×15 mL). Separated organic layer was dried over sodium sulfate, filtered and concentrated under reduced pressure. Obtained crude material was purified through silica gel column chromatography using 5% EtOAc/hexanes to afford compound 44 (100 mg, 50%) as light yellow syrup.

Compound 44: $^1$H NMR (500 MHz, CDCl$_3$): δ=7.20 (dd, J=8.4, 5.8 Hz, 2H), 7.01 (t, J=8.7 Hz, 2H), 6.30 (s, 1H), 5.95 (s, 1H), 3.95 (s, 2H), 3.49 (q, J=7.0 Hz, 2H), 2.27-2.22 (m, 2H), 1.85 (d, J=0.9 Hz, 3H), 1.47-1.38 (m, 2H), 1.28-1.23 (m, 9H), 0.86 (t, J=6.9 Hz, 3H); LC-MS: 10.00%; m/z 259.3 [M-(OEt-1)]$^+$ at RT 4.47 min; (column; X-select CSH C-18 (50×3.0 mm, 2.5 µm); ACN: 2.5 mM NH$_4$OAc; 0.8 mL/min); HPLC (purity): 99.78%; (column: XSELECT CSH C-18 (150×4.6 mm, 3.5 µm); RT 17.84 min; ACN: 5 mM NH$_4$OAc; 1.0 mL/min).

Example 26: Synthesis of ethyl (E)-4-((E)-4-fluorobenzylidene)non-2-enoate Compound 45 (Scheme 30)

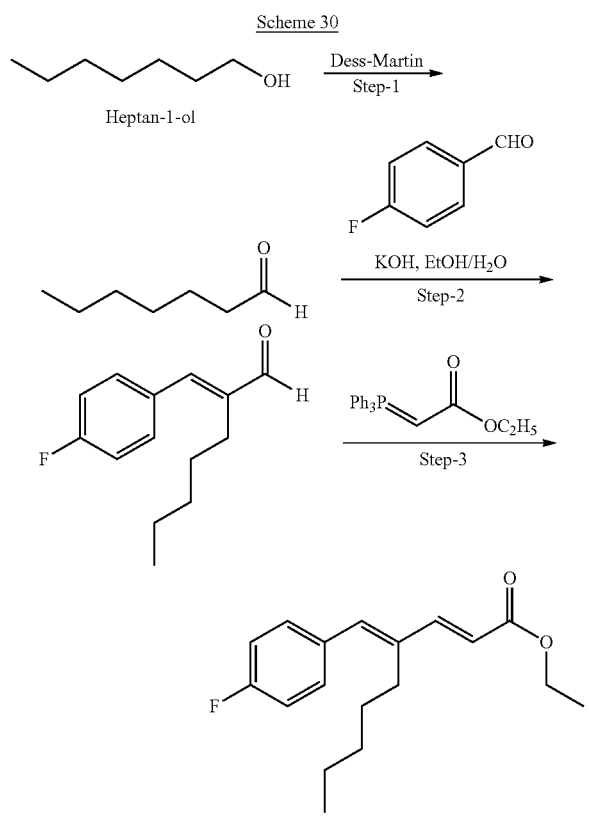

Step 1

Heptan-1-ol (6.2 mL, 43.02 mmol) was dissolved in DCM (50 mL) and Dess-Martin Periodinane (21.9 g, 51.63 mmol) was added portion wise at 0° C., under nitrogen atmosphere. The resultant reaction mixture was stirred at room temperature for 4 h. The reaction was monitored by TLC. After completion of the reaction, the mixture was quenched with water (50 mL) and filtered through a pad of celite. Obtained filtrate was washed with saturated NaHCO₃ solution, dried over sodium sulfate and concentrated under reduced pressure. Obtained crude material was purified through silica gel column chromatography using 5% EtOAc/hexanes to afford heptanal (3.8 g, 77%) as syrup.

$^1$H NMR (400 MHz, CDCl$_3$): δ 9.86 (s, 1H), 2.47-2.39 (m, 2H), 1.68-1.54 (m, 2H), 1.36-1.24 (m, 6H), 0.90 (t, J=7.4 Hz, 3H).

Step 2

Heptanal (3.8 g, 33.2 mmol) was dissolved in EtOH:H₂O (60 mL, 2:1). KOH (279 mg, 48.2 mmol) followed by the addition of 4-fluorobenzaldehyde (4.9 g, 39.5 mmol) at 0° C. The resultant reaction mixture was stirred at room temperature for 16 h. The reaction was monitored by TLC. After completion of the reaction, volatiles were removed under reduced pressure. Crude material was diluted with water (30 mL) and extracted with DCM (2×50 mL). Organic layer was dried over sodium sulfate and concentrated under reduced pressure. Obtained crude material was purified through silica gel column chromatography using 5-7% EtOAc/hexanes to afford 2-(4-fluorobenzylidene)heptanal (4 g) as yellow syrup. This material was used in the next step without any further purification.

Step 3: Synthesis of ethyl (E)-4-((E)-4-fluorobenzylidene)non-2-enoate (Compound 45)

Crude 2-(4-fluorobenzylidene)heptanal (1.5 g, 6.81 mmol) was dissolved in PhCH₃ (15 mL) and ethyl 2-(triphenyl-λ5-phosphanylidene)acetate (4.7 g, 13.5 mmol) was added in a sealed tube under nitrogen atmosphere. The resultant reaction mixture was heated to 100° C. and stirred for 16 h. The reaction was monitored by TLC. After completion of the reaction, the reaction mixture was cooled to room temperature and volatiles were evaporated under reduced pressure. Obtained crude material was purified through silica gel column chromatography using 5% EtOAc/hexanes followed by preparative HPLC to afford title compound 45 (1.05 g, 76%) as light yellow syrup.

Compound 45: $^1$H NMR (500 MHz, CDCl$_3$): δ 7.40 (d, J=15.6 Hz, 1H), 7.31 (dd, J=5.5, 8.4 Hz, 2H), 7.08 (t, J=8.7 Hz, 2H), 6.76 (s, 1H), 5.99 (d, J=15.6 Hz, 1H), 4.26 (q, J=7.0 Hz, 2H), 2.47-2.41 (m, 2H), 1.59-1.53 (m, 2H), 1.39-1.32 (m, 7H), 0.92 (t, J=7.0 Hz, 3H). LC-MS (ESI): 98.74%; m/z 291.2 [M+H]⁺ at RT 5.54 min; (column; Kinetex EVO C-18 (50×3.0 mm, 2.6 µm); 2.5 mM aq. NH₄OAc:ACN; 0.8 mL/min). HPLC (purity): 93.55%; (column: X SELECT CSH C-18 (150×4.6 mm, 3.5µ); RT 16.27 min; 5 mM NH₄OAc:ACN; 1.0 mL/min).

Compound 46

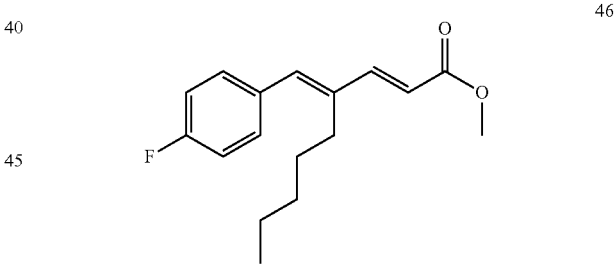

Compound 46 can be prepared as described in Horie Hiroaki, et al., "Nickel-catalyzed intermolecular codimerization of acrylates and alkynes", Chemical Communications (Cambridge, United Kingdom), Volume: 47, Issue: 9, Pages: 2658-2660, Journal, 2011.

In general the reaction can be performed in a 5 mL sealed vessel equipped with a teflon-coated magnetic stirrer tip. An acrylate (0.60 or 1.0 mmol) and an alkyne (0.50 mmol) are added to a solution of bis(1,5-dicyclooctadiene)nickel (14 mg, 0.050 mmol), tricyclohexylphosphine (14 mg, 0.050 mmol) and N-aryl-2-aminopyridine (0.10 mmol) in toluene (5 mL) in a dry box. The VIAL is taken outside the dry box and heated at 100° C. for 24 h. The reaction mixture is poured into 0.5N HCL aq. (30 mL) and the mixture is extracted with ethyl acetate (3×10 mL). The combined organic layers are washed with brine, dried over sodium sulfate and concentrated in vacuo. The residue is purified by flash silica gel column chromatography (hexane/AcOEt=40/1) to give the corresponding conjugated diene as a colourless oil.

Compound 46: $^1$H NMR (500 MHz, CDCl$_3$): δ=7.39 (d, J=16.0 Hz, 1H), 7.29 (dd, J$_{HH}$=9.0, J$_{HF}$=5.0 Hz, 2H), 7.07 (dd, J$_{HH}$=9.0, J$_{HF}$=9.0 Hz, 2H), 6.75 (s, 1H), 5.98 (d, J=16.0 Hz, 1H), 3.79 (s, 3H), 2.43 (t, J=8.0 Hz, 2H), 1.53 (m, 2H), 1.34 (m, 4H), 0.90 (j, J=7.0 Hz, 3H). MS (EI): m/z (%) 276 ([M]$^+$, 56), 219 ([M-Bu]$^+$, 85), 159 (100), 109 ([F—C$_6$H$_4$—CH$_2$]$^+$, 60).

BIOLOGICAL EXAMPLES

Cell Culture and Cell Line Generation

Cells were maintained in minimal essential medium (EMEM, Lonza) containing 10% fetal bovine serum (M10). HEK293T stably expressing olfactory chaperone proteins from the RTP family as described in WO 2006/002161 (introduced here as a reference) were generated by transfecting HEK293T cells with expression vector containing the chaperone gene sequences and a resistance gene to puromycin, using Lipofectamine 2000. A recombinant cell population was selected by adding 10 µg/ml of puromycin into the culture medium. Monoclonal populations were further obtained by limit dilution procedure. Briefly, a cell suspension was diluted to contain 1 cell per ml and this dilution was dispatched in poly-D-lysine-coated 96 well plates (200 µl of dilution per well). After 5 days of culture, the presence and number of cell colonies per well was checked under a phase contrast microscope. After 5 additional days of culture, wells containing a single colony were harvested and each collected population was amplified independently.

Agonist and Tested Molecule Dilution

The 5-alpha-androst-16-ene-3-one, used as an agonist of the human olfactory receptor OR7D4 and the tested molecules were diluted at a concentration of 1 mole/litre (M) into dimethyl sulfoxide (DMSO) to generate stock solutions.

For concentration-response analysis, serial dilutions of the tested molecules were prepared from stock solutions in EMEM plated into 96-well plates.

OR7D4 Expression and Luciferase Assay.

To demonstrate the activation of OR7D4 by its agonist androstenone and the inhibition of this activation by antagonist compounds, a Luciferase-based gene reporter assay (Promega, Leiden, The Netherlands) was used as described in Saito et al. (Saito et al., 2004 *Cell* Vol. 119, 679-691). Briefly, cells were plated on poly-D-lysine-coated 96-well plates (BD Bioscience, Erembodegem-Dorp, Belgium) and transfected with a plasmid containing CRE-luciferase and a plasmid containing OR7D4. Sixteen hours after transfection, the culture medium was replaced by serum-free EMEM containing the tested ligands at a determined concentration. After four hours of incubation at 37° C. degree, cells were lysed and processed for luminescence measurement according to the manufacturer's protocols. Luminescence emission was recorded on a Spectra Max M5 reader (Molecular Devices, Sunnyvale, Calif.). Results were expressed as percentage of the response induced by 10 µM of the adenylate cyclase activator Forskolin.

Identification of Antagonists for OR7D4

The ability of the compounds of the invention to inhibit the activity of androstenone on OR7D4 receptor was assessed by the luciferase assay described above.

To determine whether a molecule antagonizes OR7D4, this compound was introduced in the incubation medium of the Luciferase assay described above at a concentration of either 316 µM, 100 µM or 31.6 µM, along with the known activator of the receptor 5α-androst-16-en-3-one at a concentration of 31.6 µM. Molecules were considered as "hits" i.e., as having an antagonist effect on the receptor, if they induced a decrease of at least 50% of the luciferase production elicited upon activation of OR7D4 by 5α-androst-16-en-3-one.

Putative antagonist molecule libraries containing compound 1 and other types of molecules were used to identify antagonist of the receptor OR7D4. The screening campaign was performed on the OR7D4 with a series of 112 putative antagonist molecules. In this screening campaign, compound 1 was identified as a hit.

The compound 1 was further confirmed as antagonist of OR7D4 by performing dose-response analysis using the luciferase assay. Different concentrations of compound 1, ranging from 31.6 nM to 1 mM were tested on HEK293 cell expressing OR7D4 and stimulated with 31.6 µM of 5α-androst-16-en-3-one. The results presented on FIG. 1 show a decrease of Luciferase activity elicited 5α-androst-16-en-3-one proportional to the concentration of compound 1.

As a control, cell that did not expressed the receptor were stimulated by forskolin, a pharmacological agent that induces a receptor-independent production of cAMP and induces therefore a production of Luciferase. This production is not affected by compound 1, indicating that its action as antagonist depends well on the OR7D4 receptor.

The antagonistic property of compound 1 on OR7D4 was further confirmed by measuring the response of the OR7D4 to 5α-androsta-4,16-dien-3-one in presence of compound 1, using the luciferase assay as describe hereinabove. The observed inhibition was in the same range as the one observed when stimulating the receptor with 5α-androst-16-en-3-one. Typically, the IC50 recorded reached a value of 2.5 micromolar.

Structure-Activity Relationship Study on OR7D4 Antagonist

To further explore the antagonism on OR7D4, a series of compounds structurally related to compound 1 were synthesized and assessed as antagonists of OR7D4 by dose-response analysis using the luciferase assay. Table 4 summarizes the results of the structure-activity study by giving the IC50 (inhibitory concentration 50, i.e. the concentration of antagonist that induces a half decrease of the luciferase production obtained without antagonist) of the different tested analogues.

TABLE 4

| Compound | Name or Structure | IC50 (micromolar) |
|---|---|---|
| 1 | ![structure] | 2 |
| 2 | ![structure] | 25 |

TABLE 4-continued

| Compound | Name or Structure | IC50 (micromolar) |
|---|---|---|
| 3 | (structure) | 50 |
| 4 | (structure) | 16 |
| 5 | (structure) | 14 |
| 6 | (structure) | 25 |
| 7 | (structure) | 13 |
| 8 | (structure) | 1 |
| 9 | (structure) | 1 |
| 10 | (structure) | 2 |
| 11 | (structure) | 8 |
| 12 | (structure) | 8 |
| 13 | (structure) | 7 |
| 14 | (structure) | 14 |
| 15 | (structure) | 85 |

TABLE 4-continued
| Compound | Name or Structure | IC50 (micromolar) |
|---|---|---|
| 16 | 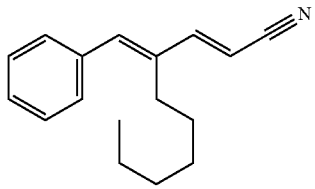 [SMILES: CCCCCCC(/C=C/C#N)=C\c1ccccc1] | 8 |
| 17 | 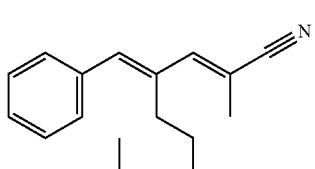 | 12 |
| 18 | 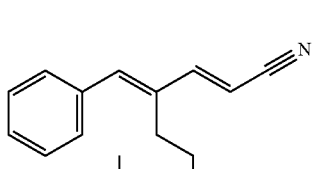 | 13 |
| 19 | 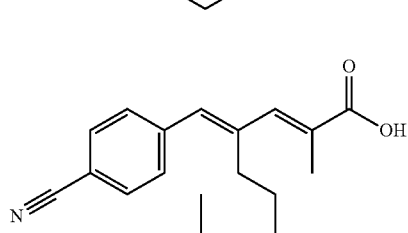 | 45 |
| 20 | 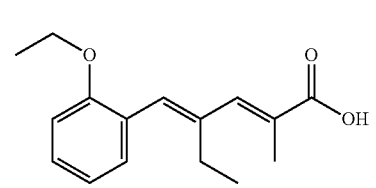 [SMILES: CCOc1ccccc1/C=C(/C=C(\C)C(=O)O)CC] | 32 |
| 21 | 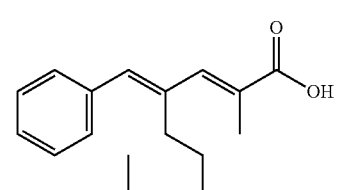 | 62 |
| 22 | 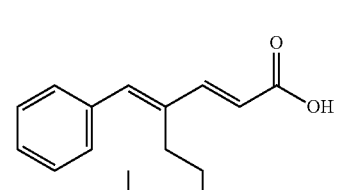 | 75 |
| 23 | 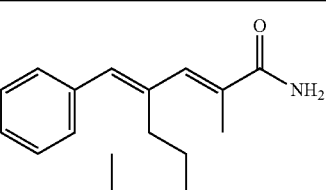 | 1 |
| 24 | 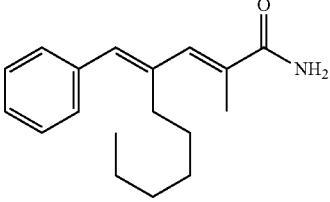 | 2 |
| 25 | 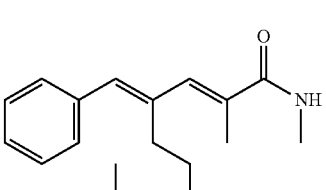 | 126 |
| 26 | 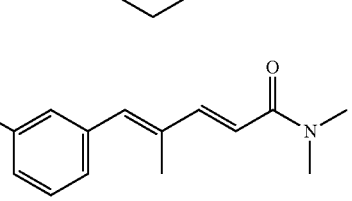 | 11 |
| 27 | 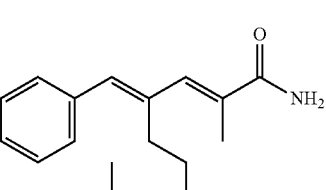 | 14 |
| 28 | 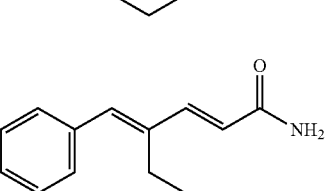 | 2 |
| 29 | 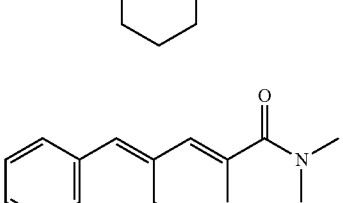 | 1 |

TABLE 4-continued
| Compound | Name or Structure | IC50 (micromolar) |
|---|---|---|
| 30 | 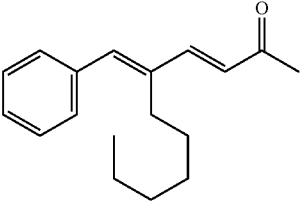 [SMILES: CCCCCCC(/C=C/C(C)=O)=C\c1ccccc1] | 6 |
| 31 | 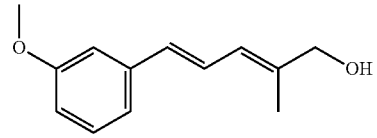 | 63 |
| 32 | 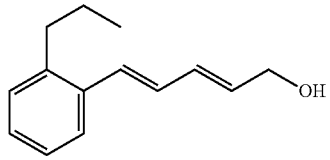 | 126 |
| 33 | 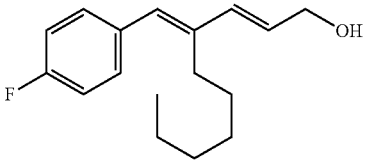 [SMILES: CCCCCCC(/C=C/CO)=C\c1ccc(F)cc1] | 18 |
| 34 | 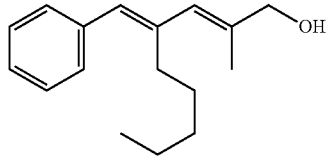 | 19 |
| 35 | 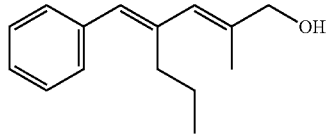 [SMILES: CCCC(/C=C(\C)CO)=C\c1ccccc1] | 53 |
| 36 | 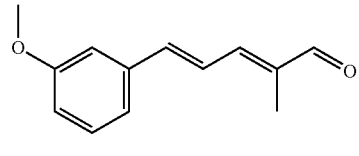 | 79 |
| 37 | 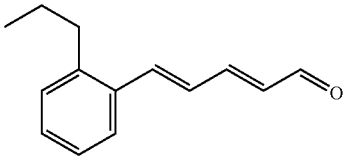 | 126 |
| 38 | 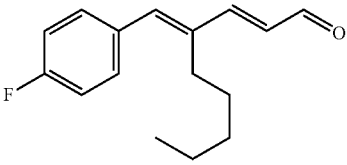 [SMILES: CCCCCC(/C=C/C=O)=C\c1ccc(F)cc1] | 25 |
| 39 | 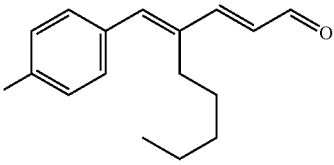 | 6 |
| 40 | 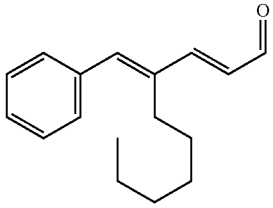 | 29 |
| 41 | 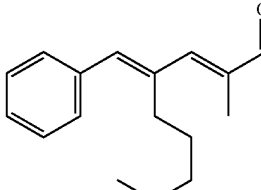 | 187 |
| 42 | 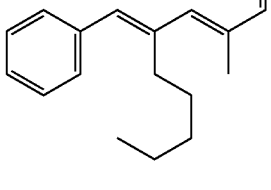 | 25 |
| 43 | 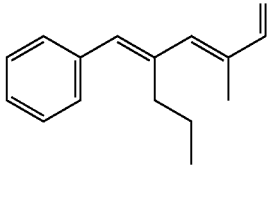 | 126 |
| 44 | 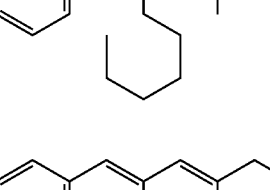 | 22 |

TABLE 4-continued

| Compound | Name or Structure | IC50 (micromolar) |
|---|---|---|
| 45 | (4-fluorophenyl substituted diene ester, ethyl ester with pentyl chain) | 4 |
| 46 | (4-fluorophenyl substituted diene ester, methyl ester with pentyl chain) | 25 |

When tested in the above described assay, preferred compounds of the invention showed an $IC_{50}$ comprised between 0.5 μM and 200 μM, indicating that such compounds are able to antagonize the activity of androstenone on OR7D4 receptor.

Sensory Evaluation of Compounds of the Invention Versus Androstenone

This example demonstrates the effect of the compound 1 in reducing 16-(5-alpha)-androstenone ("Androstenone") odour in a sensory evaluation test, as predicted by the antagonistic effects observed in the bioassay described above. Androstenone is a key element of body malodour, particularly underarm, and generally has a strong unpleasant odour to those who can perceive it.

Since it is not possible to assess androstenone in isolation in vivo, as other body malodour components will always be present, we have utilised an in vitro sensory tests, using the isolated material in jars. The sensory test consists of a standard "Triangle Test" where assessors have to identify the "odd jar out", the one which contains just androstenone. They are also requested to identify whether the odd jar has a weaker or stronger androstenone smell than the other two.

Each set also contains two blank jars to avoid potential 'carry over' effect of either the androstenone and/or compound 1.

A set of five jars is prepared for each assessor to smell. Each set includes three test jars and the two blank jars, prepared as follows:

Five 120 ml "Beatson" jars are used with a 4.5 cm diameter de-sized 100% cotton cloth placed into each jar. Five small round pieces of the same cotton are placed on top of a small vial lid in the jar on top of larger cotton cloth.

One test jar contains just 50 μl of androstenone (1% in diethyl phthalate) at 6.2% in ethanol, dropped onto the 4.5 cm cloth and allowed to dry for 12 minutes to remove the ethanol. Two test jars contain androstenone (same level and procedure as above) and compound 1 (200 μl neat pipetted onto the small cloth piece resting on the vial lid, with no drying step). The two ingredients are kept separate to avoid direct contact and reduce other possible chemical effects which may affect the sensory perception of the ingredients when combined. The two blank jars contain cotton cloths only, without androstenone or compound 1. The jars are sealed and left at room temperature for 5 days prior to assessment to allow full equilibration of the poorly volatile materials.

The jars are then coded and randomised for each assessor following the Williams Latin Square method which minimises the sample order effect and ensures sufficient assessments per sample in each test. The blank jars are always placed at positions two and four, for example:

| Position 1 | Test jar Androstenone (A) |
| Position 2 | Blank jar |
| Position 3 | Test Jar Androstenone + Compound 1 (A + C1) |
| Position 4 | Blank jar |
| Position 5 | Test Jar Androstenone + Compound 1 (A + C1) |

Each respondent is asked to smell each jar following the order as set out by the test coordinator. Each jar is be opened and resealed before moving onto the next jar. An interval of twenty seconds is required between smelling each sample. The assessors record the presence of androstenone in each jar and add any comments on an assessment sheet as supplied for the test. Due to the possibility of adaptation, respondents are not allowed to repeatedly smell the samples within each test assessment.

However, the test can be repeated after a suitable time interval (e.g. two hours) to confirm the results.

The following results illustrate the utility of the invention. In the following table 5, the results for six assessors are shown. For all six assessors, the jar containing the androstenone alone was correctly identified as the "odd jar out" and had a significantly higher androstenone odour than the other two jars containing androstenone and compound 1. This clearly demonstrates the effectiveness of compound 1 in reducing androstenone odour (Table 5).

TABLE 5

| Assessor | Jar Position 1 | 2 | 3 | 4 | 5 | Odd one Out and Comment |
|---|---|---|---|---|---|---|
| 1 | A + C1 | Blank | A + C1 | Blank | A | Jar 5 strong androstenone<br>No androstenone in jars 1 and 3 |
| 2 | A | Blank | A + C1 | Blank | A + C1 | Jar 1 strong androstenone<br>No androstenone in jars 3 and 5 |
| 3 | A | Blank | A + C1 | Blank | A + C1 | Jar 1 strong androstenone<br>Weak androstenone in jars 3 and 5 |
| 4 | A + C1 | Blank | A | Blank | A + C1 | Jar 3 strong androstenone<br>Weak androstenone in jars 1 and 5 |
| 5 | A + C1 | Blank | A + C1 | Blank | A | Jar 5 strong androstenone<br>Weak androstenone in jars 1 and 3 |

TABLE 5-continued

| | Jar Position | | | | | |
|---|---|---|---|---|---|---|
| Assessor | 1 | 2 | 3 | 4 | 5 | Odd one Out and Comment |
| 6 | A + C1 | Blank | A + C1 | Blank | A | Jar 5 strong androstenone Weak androstenone in jars 1 and 3 |

The test was repeated with a second compound of the invention—compound 16 (C16), referred to hereinabove (Table 6)—and similar results were achieved, again illustrating the utility of the invention. The testing protocol was identical; however, as compound 16 is a solid ingredient, 400 µl of a 50% dilution in diethyl phthalate was added to the test jars.

TABLE 6

| | Jar Position | | | | | |
|---|---|---|---|---|---|---|
| Assessor | 1 | 2 | 3 | 4 | 5 | Odd one Out and Comment |
| 1 | A + C16 | Blank | A + C16 | Blank | A | Jar 5 strong androstenone No androstenone in jars 1 and 3 |
| 2 | A + C16 | Blank | A | Blank | A + C16 | Jar 3 strong androstenone No androstenone in jars 1 and 5 |
| 3 | A | Blank | A + C16 | Blank | A + C16 | Jar 1 strong androstenone No androstenone in jars 3 and 5 |
| 4 | A + C16 | Blank | A | Blank | A + C16 | Jar 3 strong androstenone Weak androstenone in jars 1 and 5 |

An alternative sensory test was also used to demonstrate the effect of compound 1 on the perception of androstenone. The test consists, in a first step, in microinjecting androstenone (at 0.6% in ethanol), compound 1 (pure) or androstenone+compound 1 in 10 L Tedlar™ bags specially conceived for gas sampling, previously loaded with a known volume of pure air (from oil free compressor with additional charcoal filters). Than the compound of interest (EtOH solution) is injected with a high accuracy micro-syringe through a septum placed on the tap-valve.

The odour presentation device consists of a cylinder to be filled with clean air. The bag is inserted in the cylinder and connected to a sampling installation in the cylinder by means of a valve. By controlled injection of clean air into the cylinder, the interior pressure is raised and the sampling air is pressed in a controlled manner out of the sample container through the opened valve. This sampling air is transferred to the nose of the corresponding sensory odour panel member by means of a funnel. By this means, each sensory odour panel member receives an identical sample with a standardized volume flow and a constant provision time. The outlet flow rate is between 10-20 L/min (in order to avoid any mixing with ambient air before reaching the nose).

The expert panel is entering the room 15 minutes before starting the test. The basic standard test is a rating in intensity and the use of the closest chemical descriptors according to the following order of presentation:
Androstenone
Compound 1
Mix: androstenone+compound 1 (at same concentrations as for 1 and 2).

Each assessor can smell for few seconds. A pause of min. 1 minute is considered between presentations.

The individual rating is done with a resolution of 0.5 on a scale ranging from 0 (no odour) to 5 (saturating odour).

The following results (Table 7) show that the typical odour of sweat of Androstenone completely disappears when androstenone is smelled in the presence of the compound 1 of the invention. The remaining odour of mushroom corresponds to the intrinsic smell of compound 1. Since the odour intensity of the compound 1 is lower than the one of androstenone alone, it cannot overpower the odour androstenone. Therefore, the suppression of androstenone perception cannot be accounted to a masking or covering effect of compound 1 but well to a true suppression of the perception of androstenone by antagonizing its cognate olfactory receptor namely OR7D4.

TABLE 7

| | Androstenone | | Androstenone + compound 1 | |
|---|---|---|---|---|
| Assessor | Intensity | Odour description | Intensity | Odour description |
| 1 | 4.5 | Sweat | 2.5 | mushroom |
| 2 | 4 | Sweat | 2 | mushroom |
| 3 | 3 | Sweat | 2 | mushroom |
| 4 | 3.5 | Sweat | 2 | mushroom |

The invention claimed is:
1. An OR7D4 antagonist, wherein the antagonist comprising a compound of formula (I) or a stereoisomer thereof,

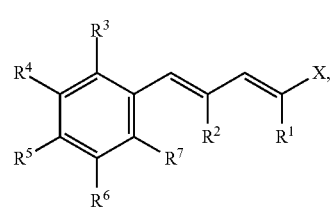

(I)

wherein the compound or stereoisomer thereof is an antagonist of the OR7D4 receptor, and wherein
X is selected from the group consisting of —CN, —C(=O)OR$^8$, —C(=O)—C$_{1-6}$alkyl, —C(=O)—NR$^9$R$^{10}$, —CH$_2$—OH, —CH$_2$—CH$_2$—OH, —C(=O)H, and C$_{1-6}$alkoxyC$_{1-6}$alkyl;

$R^1$ is hydrogen or $C_{1-6}$ alkyl;

$R^2$ is a group selected from $C_{5-6}$ alkyl, $C_{5-6}$ alkenyl, 3-tert-butyl-1-methylpropyl, or $C_1$alkyl substituted with a $C_5$cycloalkyl;

$R^3$ is selected from the group consisting of hydrogen, halo, $C_{1-6}$alkyl, $C_{1-6}$alkoxy, $C_{1-6}$alkoxy$C_{1-6}$alkyl, and cyano;

$R^4$ is selected from the group consisting of hydrogen, halo, $C_{1-6}$alkyl, $C_{1-6}$alkoxy, $C_{1-6}$alkoxy$C_{1-6}$alkyl, and cyano;

$R^5$ is selected from the group consisting of hydrogen, halo, $C_{1-6}$alkyl, $C_{1-6}$alkoxy, $C_{1-6}$alkoxy$C_{1-6}$alkyl, and cyano;

$R^6$ is selected from the group consisting of hydrogen, halo, $C_{1-6}$alkyl, $C_{1-6}$alkoxy, $C_{1-6}$alkoxy$C_{1-6}$alkyl, and cyano;

$R^7$ is selected from the group consisting of hydrogen, halo, $C_{1-6}$alkyl, $C_{1-6}$alkoxy, $C_{1-6}$alkoxy$C_{1-6}$alkyl, and cyano;

$R^8$ is hydrogen or $C_{1-6}$alkyl; $R^9$ is hydrogen or $C_{1-6}$alkyl; $R^{10}$ is hydrogen or $C_{1-6}$alkyl;

with the following provisos:

when X is —C(=O)—NR$^9$R$^{10}$ then $R^1$ is —CH$_3$;

when X is —C(=O)H or —C(=O)OR$^8$, then $R^4$ is not $C_{1-6}$alkoxy;

and the compound of formula (I) is none of:

methyl (2E,4E)-4-(4-fluorobenzylidene)-2-nonenoate;

(2E,4Z)-4-benzylidene-2-methyldec-2-en-1-ol, methyl (2E,4E)-4[(4-methoxyphenyl)methylene]non-2-enoate; and (2E,4E)-4-benzylidenedec-2-enenitrile.

2. The OR7D4 antagonist according to claim 1, wherein X is selected from the group consisting of —CN, —C(=O)OC$_{1-4}$alkyl, —C(=O)—OH, —C(=O)—C$_{1-4}$alkyl, —C(=O)—NH$_2$, —C(=O)—NHC$_{1-4}$alkyl, —C(=O)—N(C$_{1-4}$alkyl)$_2$, —CH$_2$—OH, —CH$_2$—CH$_2$—OH, —C(=O)H, and C$_{1-4}$alkoxyC$_{1-4}$alkyl;

$R^1$ is hydrogen or $C_{1-4}$alkyl;

$R^2$ is a group selected from $C_{5-6}$alkyl, $C_{5-6}$alkenyl, 3-tert-butyl-1-methylpropyl, or $C_1$alkyl substituted with a $C_5$cycloalkyl;

$R^3$ is selected from the group consisting of hydrogen, halo, $C_{1-6}$alkyl, $C_{1-4}$alkoxy, $C_{1-4}$alkoxyC$_{1-4}$alkyl, and cyano;

$R^4$ is selected from the group consisting of hydrogen, halo, $C_{1-6}$alkyl, $C_{1-4}$alkoxy, $C_{1-4}$alkoxyC$_{1-4}$alkyl, and cyano;

$R^5$ is selected from the group consisting of hydrogen, halo, $C_{1-6}$alkyl, $C_{1-4}$alkoxy, $C_{1-4}$alkoxyC$_{1-4}$alkyl, and cyano;

$R^6$ is selected from the group consisting of hydrogen, halo, $C_{1-6}$alkyl, $C_{1-4}$alkoxy, $C_{1-4}$alkoxyC$_{1-4}$alkyl, and cyano; and $R^7$ is selected from the group consisting of hydrogen, halo, $C_{1-6}$alkyl, $C_{1-4}$alkoxy, $C_{1-4}$alkoxyC$_{1-4}$alkyl, and cyano.

3. The OR7D4 antagonist according to claim 1, wherein X is selected from the group consisting of —CN, —C(=O)OC$_{1-2}$alkyl, —C(=O)OH, C(=O)—C$_{1-2}$alkyl, —C(=O)—NH$_2$, —C(=O)—NHC$_{1-2}$alkyl, —C(=O)—N(CH$_3$)$_2$), —CH$_2$—OH, —CH$_2$—CH$_2$—OH, —C(=O)H, and C$_{1-2}$alkoxyC$_{1-2}$alkyl, $R^1$ is hydrogen or $C_{1-2}$alkyl;

$R^2$ is a group selected from $C_{5-6}$alkyl, $C_{5-6}$alkenyl, 3-tert-butyl-1-methylpropyl, or $C_1$alkyl substituted with a $C_5$cycloalkyl;

$R^3$ is selected from the group consisting of hydrogen, fluoro, chloro, $C_{1-6}$alkyl, $C_{1-2}$alkoxy, $C_{1-2}$alkoxyC$_{1-2}$alkyl, and cyano;

$R^4$ is selected from the group consisting of hydrogen, fluoro, chloro, $C_{1-6}$alkyl, $C_{1-2}$alkoxy, $C_{1-2}$alkoxyC$_{1-2}$alkyl, and cyano;

$R^5$ is selected from the group consisting of hydrogen, fluoro, chloro, $C_{1-6}$alkyl, $C_{1-2}$alkoxy, $C_{1-2}$alkoxyC$_{1-2}$alkyl, and cyano;

$R^6$ is selected from the group consisting of hydrogen, fluoro, chloro, $C_{1-6}$alkyl, $C_{1-2}$alkoxy, $C_{1-2}$alkoxyC$_{1-2}$alkyl, and cyano; and $R^7$ is selected from the group consisting of hydrogen, fluoro, chloro, $C_{1-6}$alkyl, $C_{1-2}$alkoxy, $C_{1-2}$alkoxyC$_{1-2}$alkyl, and cyano.

4. The OR7D4 antagonist according to claim 1, wherein X is selected from the group consisting of —CN, —C(=O)—O—CH$_3$, —C(=O)—O—CH$_2$—CH$_3$, —C(=O)OH, —C(=O)—CH$_3$, —C(=O)—CH$_2$—CH$_3$, —C(=O)—NH$_2$, —C(=O)—NH—CH$_3$, —C(=O)—N(CH$_3$)$_2$, —CH$_2$—OH, —CH$_2$—CH$_2$—OH, —C(=O)H, and —CH$_2$—O—CH$_3$, —CH$_2$—O—CH$_2$—CH$_3$;

$R^1$ is hydrogen or —CH$_3$;

$R^2$ is a group selected from $C_{5-6}$alkyl, $C_{5-6}$alkenyl, 3-tert-butyl-1-methylpropyl, or $C_1$alkyl substituted with a $C_5$cycloalkyl;

$R^3$ is selected from the group consisting of hydrogen, fluoro, chloro, $C_{1-6}$alkyl, $C_{1-2}$alkoxy, $C_{1-2}$alkoxyC$_{1-2}$alkyl, and cyano;

$R^4$ is selected from the group consisting of hydrogen, fluoro, chloro, $C_{1-6}$alkyl, $C_{1-2}$alkoxy, $C_{1-2}$alkoxyC$_{1-2}$alkyl, and cyano;

$R^5$ is selected from the group consisting of hydrogen, fluoro, chloro, $C_{1-6}$alkyl, $C_{1-2}$alkoxy, $C_{1-2}$alkoxyC$_{1-2}$alkyl, and cyano;

$R^6$ is selected from the group consisting of hydrogen, fluoro, chloro, $C_{1-6}$alkyl, $C_{1-2}$alkoxy, $C_{1-2}$alkoxyC$_{1-2}$alkyl, and cyano; and $R^7$ is selected from the group consisting of hydrogen, fluoro, chloro, $C_{1-6}$alkyl, $C_{1-2}$alkoxy, $C_{1-2}$alkoxyC$_{1-2}$alkyl, and cyano.

5. The OR7D4 antagonist according to claim 1, wherein X is selected from the group consisting of —CN, —C(=O)—O—CH$_3$, —C(=O)—O—CH$_2$—CH$_3$, —C(=O)—CH$_3$, —C(=O)—NH$_2$, —C(=O)—NH—CH$_3$, —C(=O)—N(CH$_3$)$_2$;

$R^1$ is hydrogen or —CH$_3$;

$R^2$ is a group selected from $C_{5-6}$alkyl, $C_{5-6}$alkenyl, 3-tert-butyl-1-methylpropyl, or $C_1$alkyl substituted with a $C_5$cycloalkyl;

$R^3$ is hydrogen; $R^4$ is hydrogen; $R^5$ is hydrogen; $R^6$ is hydrogen; and $R^7$ is hydrogen.

6. The OR7D4 antagonist according to claim 1, selected from the group consisting of:

| Compound | Structure |
|---|---|
| 1 | 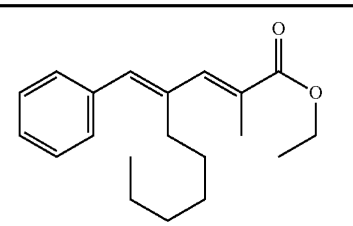 |

-continued

| Compound | Structure |
|---|---|
| 5 | (4-fluorophenyl-substituted diene ethyl ester with pentyl chain) |
| 7 | (4-cyanophenyl-substituted diene methyl-branched ethyl ester with pentyl chain) |
| 8 | (phenyl diene methyl ethyl ester with pentenyl chain) |
| 9 | (phenyl diene methyl ethyl ester with butyl chain) |
| 10 | (phenyl diene methyl ester with pentyl chain) |
| 11 | (phenyl diene methyl ethyl ester with branched alkyl chain) |

-continued

| Compound | Structure |
|---|---|
| 12 | (phenyl diene methyl ethyl ester with cyclopentylmethyl chain) |
| 13 | (phenyl diene ethyl ester with pentyl chain) |
| 14 | (phenyl diene ethyl ester with pentyl chain) |
| 17 | (phenyl diene methyl nitrile with pentyl chain) |
| 18 | (phenyl diene nitrile with pentyl chain) |
| 19 | (4-cyanophenyl diene methyl carboxylic acid with pentyl chain) |
| 21 | (phenyl diene methyl carboxylic acid with pentyl chain) |

| Compound | Structure |
|---|---|
| 22 | 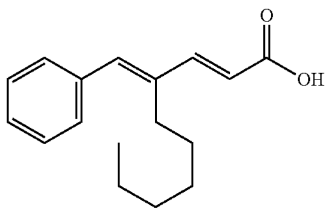 [SMILES: CCCCCCC(/C=C/C(=O)O)=C\c1ccccc1] |
| 23 | 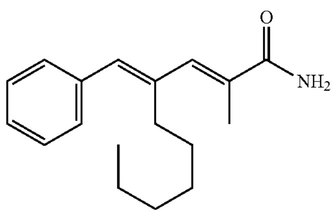 [SMILES: CCCCCCC(=C\c1ccccc1)/C=C(\C)C(N)=O] |
| 24 | 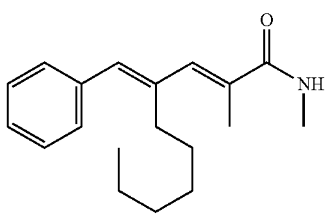 [SMILES: CCCCCCC(=C\c1ccccc1)/C=C(\C)C(=O)NC] |
| 26 | 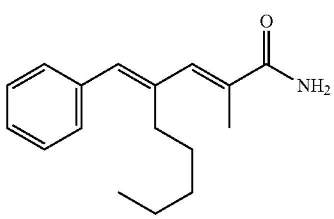 |
| 28 | 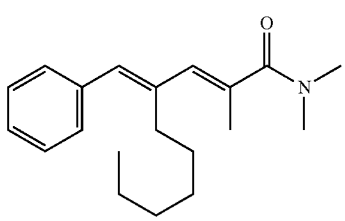 [SMILES: CCCCCCC(=C\c1ccccc1)/C=C(\C)C(=O)N(C)C] |
| 29 | 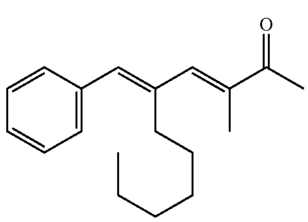 [SMILES: CCCCCCC(=C\c1ccccc1)/C=C(\C)C(C)=O] |
| 30 | 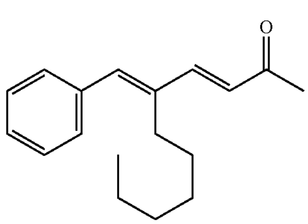 [SMILES: CCCCCCC(/C=C/C(C)=O)=C\c1ccccc1] |

| Compound | Structure |
|---|---|
| 33 | 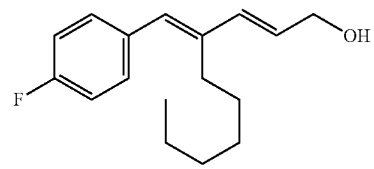 [SMILES: CCCCCCC(/C=C/CO)=C\c1ccc(F)cc1] |
| 34 | 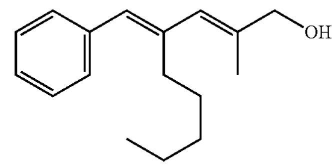 [SMILES: CCCCCC(/C=C(\C)CO)=C\c1ccccc1] |
| 38 | 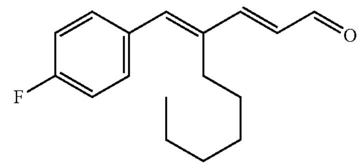 [SMILES: CCCCCCC(/C=C/C=O)=C\c1ccc(F)cc1] |
| 39 | 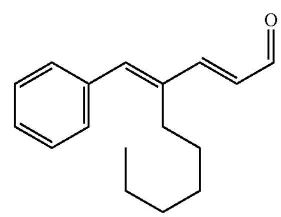 [SMILES: CCCCCCC(/C=C/C=O)=C\c1ccccc1] |
| 40 | 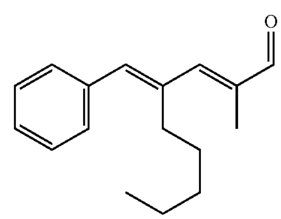 [SMILES: CCCCCC(/C=C(\C)C=O)=C\c1ccccc1] |
| 42 | 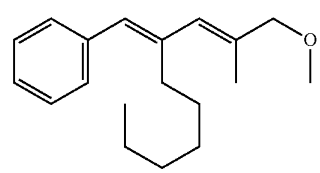 |
| 43 | 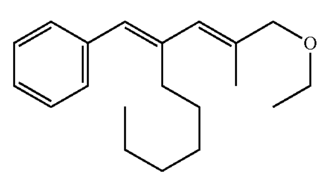 [SMILES: CCCCCCC(/C=C(\C)COCC)=C\c1ccccc1] |
| 44 | | and

| Compound | Structure |
|---|---|
| 45 | (4-fluorophenyl)-substituted diene ethyl ester with pentyl chain |

7. A consumer product comprising a OR7D4 antagonist according to claim 1.

8. The consumer product according to claim 7, which is an antiperspirant or deodorant product, further comprising a cosmetically acceptable carrier.

9. The OR7D4 antagonist according to claim 1, selected from the group consisting of:

| Compound | Structure |
|---|---|
| 1 | phenyl diene methyl-substituted ethyl ester with pentyl chain |
| 5 | (4-fluorophenyl) diene ethyl ester with pentyl chain |
| 7 | (4-cyanophenyl) diene methyl-substituted ethyl ester with pentyl chain |
| 8 | phenyl diene methyl-substituted ethyl ester with terminal alkene chain |
| 9 | phenyl diene methyl-substituted ethyl ester with butyl chain |
| 10 | phenyl diene methyl ester with hexyl chain |
| 11 | phenyl diene methyl-substituted ethyl ester with methyl-branched neopentyl chain |
| 12 | phenyl diene methyl-substituted ethyl ester with cyclopentylmethyl chain |
| 13 | phenyl diene ethyl ester with pentyl chain |
| 14 | phenyl diene ethyl ester with hexyl chain |
| 17 | phenyl diene methyl-substituted nitrile with pentyl chain |

-continued
| Compound | Structure |
|---|---|
| 18 | 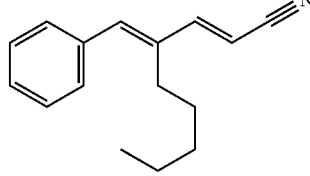 |
| 19 | 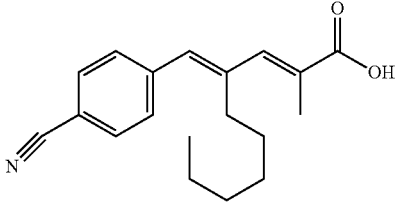 [SMILES: CCCCCCC(=C\c1ccc(C#N)cc1)/C=C(\C)C(=O)O] |
| 21 | 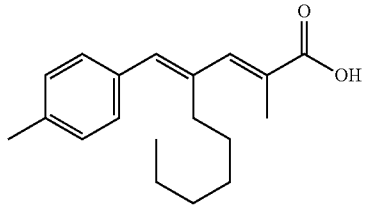 [SMILES: CCCCCCC(=C\c1ccc(C)cc1)/C=C(\C)C(=O)O] |
| 22 | 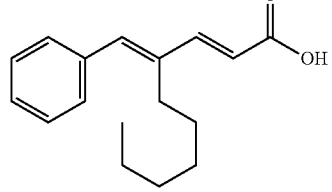 |
| 23 | 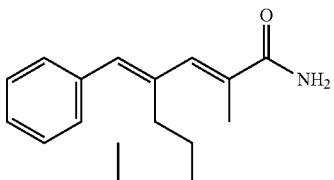 |
| 24 | 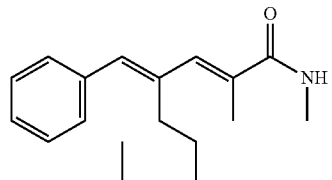 |
| 26 | 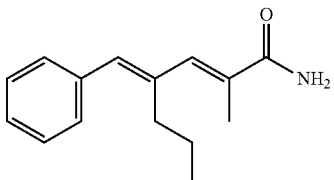 |
-continued
| Compound | Structure |
|---|---|
| 28 | 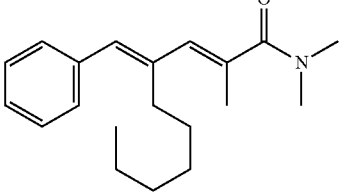 |
| 29 | 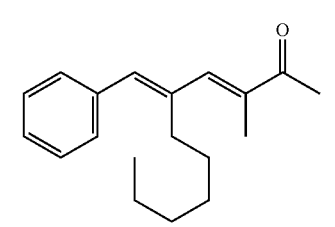 [SMILES: CCCCCCC(=C\c1ccccc1)/C=C(\C)C(C)=O] |
| 30 | 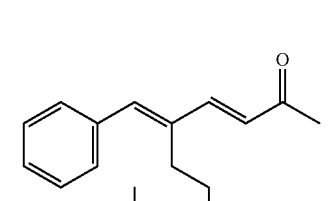 |
| 33 | 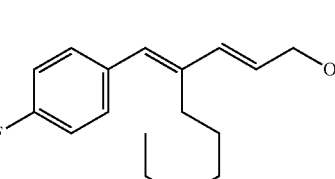 |
| 38 | 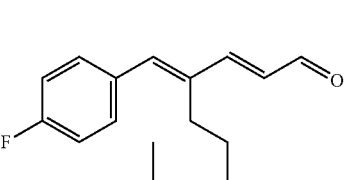 |
| 39 | 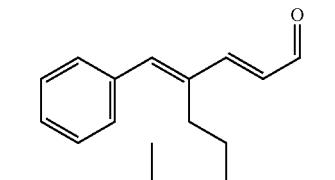 |
| 40 | 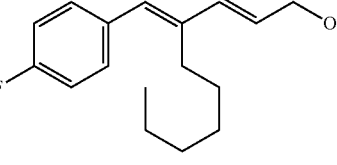 |

-continued
| Compound | Structure |
|---|---|
| 42 | 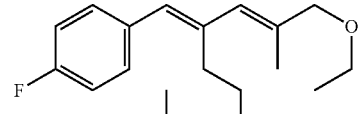 |
| 43 | 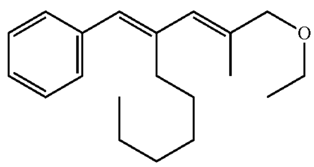 [SMILES: CCCCCCC(/C=C(\C)COCC)=C\c1ccccc1] |
-continued
| Compound | Structure |
|---|---|
| 44 | 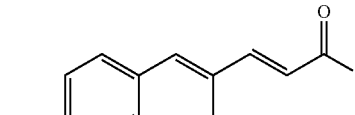 and |
| 45 | |
* * * * *